US008551484B2

(12) United States Patent
Ambrosino et al.

(10) Patent No.: US 8,551,484 B2
(45) Date of Patent: Oct. 8, 2013

(54) HUMAN ANTIBODIES AGAINST HEPATITIS C VIRUS (HCV) AND USES THEREOF

(75) Inventors: Donna M. Ambrosino, Jamaica Plain, MA (US); William D. Thomas, Jr., Dedham, MA (US); Gregory J. Babcock, Marlborough, MA (US); Teresa Broering, Brookline, MA (US); Susan Sloan, Watertown, MA (US)

(73) Assignee: University of Massachusetts, Boston, MA (US)

(*) Notice: Subject to any disclaimer, the term of this patent is extended or adjusted under 35 U.S.C. 154(b) by 722 days.

(21) Appl. No.: 12/527,663

(22) PCT Filed: Feb. 13, 2008

(86) PCT No.: PCT/US2008/001922

§ 371 (c)(1),
(2), (4) Date: Mar. 4, 2010

(87) PCT Pub. No.: WO2008/108918

PCT Pub. Date: Sep. 12, 2008

(65) Prior Publication Data

US 2012/0288510 A1 Nov. 15, 2012

Related U.S. Application Data

(60) Provisional application No. 60/902,432, filed on Feb. 21, 2007.

(51) Int. Cl.

| | |
|---|---|
| ***A61K 39/00*** | (2006.01) |
| ***A61K 39/42*** | (2006.01) |
| ***A61K 39/395*** | (2006.01) |
| ***C07K 16/00*** | (2006.01) |
| ***C07K 16/08*** | (2006.01) |
| ***C07K 16/10*** | (2006.01) |
| ***C12P 21/08*** | (2006.01) |

(52) U.S. Cl.

USPC .................. 424/149.1; 424/139.1; 424/141.1; 424/142.1; 424/147.1; 424/159.1; 424/161.1; 530/387.1; 530/387.9; 530/388.1; 530/388.15; 530/388.3; 530/391.1; 530/391.3; 530/391.7

(58) Field of Classification Search

None

See application file for complete search history.

(56) References Cited

U.S. PATENT DOCUMENTS

| | | | |
|---|---|---|---|
| 5,308,750 | A | 5/1994 | Mehta et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,595,868 | A | 1/1997 | Habets et al. |
| 5,625,126 | A | 4/1997 | Lonberg et al. |
| 5,633,425 | A | 5/1997 | Lonberg et al. |
| 5,645,983 | A | 7/1997 | Liao et al. |
| 5,661,016 | A | 8/1997 | Lonberg et al. |
| 5,753,460 | A | 5/1998 | Bisgard-Frantzen et al. |
| 5,770,429 | A | 6/1998 | Lonberg et al. |
| 5,789,650 | A | 8/1998 | Lonberg et al. |
| 5,814,318 | A | 9/1998 | Lonberg et al. |
| 5,874,299 | A | 2/1999 | Lonberg et al. |
| 5,877,397 | A | 3/1999 | Lonberg et al. |
| 5,919,454 | A | 7/1999 | Brechot et al. |
| 6,171,782 | B1 | 1/2001 | Houghton et al. |
| 2002/0016445 | A1 | 2/2002 | Persson et al. |

FOREIGN PATENT DOCUMENTS

| | | | |
|---|---|---|---|
| EP | 0569537 | B1 | 11/1993 |
| EP | 0599913 | B1 | 6/1994 |
| EP | 0947525 | A1 | 10/1999 |
| JP | 2002-521391 | A | 7/2002 |
| JP | 2002-528140 | A | 9/2002 |
| JP | 2004-524829 | A | 8/2004 |
| JP | 2006-504645 | A | 2/2006 |
| WO | WO 92/03918 | | 3/1992 |
| WO | WO-92/07001 | A1 | 4/1992 |
| WO | WO 92/22645 | | 12/1992 |
| WO | WO 93/01227 | | 1/1993 |
| WO | WO 94/25585 | | 11/1994 |
| WO | WO 96/33735 | | 10/1996 |
| WO | WO-96/33735 | A1 | 10/1996 |
| WO | WO-98/21338 | A1 | 5/1998 |
| WO | WO 98/24884 | | 6/1998 |
| WO | WO-98/24884 | A1 | 6/1998 |
| WO | WO-99/24466 | A2 | 5/1999 |
| WO | WO 00/05266 | | 2/2000 |
| WO | WO-00/05266 | A1 | 2/2000 |
| WO | WO-00/26418 | A1 | 5/2000 |
| WO | WO-02/08292 | A2 | 1/2002 |
| WO | WO-02/055560 | A2 | 7/2002 |

(Continued)

OTHER PUBLICATIONS

Lesniewski et al. Antibody to Hepatitis C Virus Second Envelope (HCV-E2) Glycoprotein. Journal of Medical Virology 1995, vol. 45, No. 4, pp. 415-422.*

International Preliminary Report on Patentability for Application No. PCT/US2008/001922, dated Aug. 26, 2009.

Office Action for Chinese Patent Application No. 200880010301.5, dated Nov. 2, 2011 (4 pages).

English Translation of Office Action for Chinese Patent Application No. 200880010301.5, dated Nov. 2, 2011 (5 pages).

Office Action issued in Canadian Patent Application No. 2,678,888, dated Dec. 19, 2012 (5 pages).

(Continued)

*Primary Examiner* — Louise Humphrey

(74) *Attorney, Agent, or Firm* — Clark & Elbing LLP

(57) ABSTRACT

Isolated human monoclonal antibodies which bind to hepatitis C virus (HCV), and related antibody-based compositions and molecules, are disclosed. The human antibodies can be produced in a transfectoma or in a non-human transgenic animal, e.g., a transgenic mouse, capable of producing multiple isotypes of human monoclonal antibodies by undergoing V-D-J recombination and isotype switching. Also disclosed are pharmaceutical compositions comprising the human antibodies, non-human transgenic animals, and hybridomas which produce the human antibodies, and therapeutic and diagnostic methods for using the human antibodies.

18 Claims, 18 Drawing Sheets

(56) References Cited

FOREIGN PATENT DOCUMENTS

| | | | |
|---|---|---|---|
| WO | WO-02/060954 | A1 | 8/2002 |
| WO | WO-02/100900 | A2 | 12/2002 |
| WO | WO-2004005890 | A2 | 1/2004 |
| WO | WO-2006/041866 | A2 | 4/2006 |

OTHER PUBLICATIONS

Official Action issued in Japanese Patent Application No. 2009-550888, dated Dec. 21, 2012 (4 pages).
Office Action for Canadian Patent Application No. 2,678,888, dated Oct. 17, 2011 (6 pages).
English Translation of Office Action for Israel Patent Application No. 200432, dated Aug. 18, 2011 (2 pages).
Patent Examination Report No. 1 issued in Australian Patent Application No. 2008223561 on Jul. 31, 2012 (3 pages).
Bartosch, Birke et al., "*In vitro* assay for neutralizing antibody to hepatitis C virus: Evidence for broadly conserved neutralization epitopes," *PNAS*, vol. 100(24):14199-14204 (2003).
Flint, Mike et al., "Characterization of Hepatitis C Virus E2 Glycoprotein Interaction with a Putative Cellular Receptor, CD81," *Journal of Virology*, vol. 73(8):6235-6244 (1999).
Grollo, L. et al., "Exploiting information inherent in binding sites of virus-specific antibodies: design of an HCV vaccine candidate cross-reactive with multiple genotypes," *Antivir. Ther.*, vol. 11(8):1005-1014 (2006).
Habersetzer, François et al., "Characterization of Human Monoclonal Antibodies Specific to the Hepatitis C Virus Glycoprotein E2 with *in Vitro* Binding Neutralization Properties," *Virology*, vol. 249:32-41 (1998).
Hadlock, Kenneth G. et al., "Human Monoclonal Antibodies That Inhibit Binding of Hepatitis C Virus E2 Protein to CD81 and Recognize Conserved Conformational Epitopes," *Journal of Virology*, vol. 74(22):10407-10416 (2000).
Owsianka, Ania et al., "Monoclonal Antibody AP33 Defines a Broadly Neutralizing Epitope on the Hepatitis C Virus E2 Envelope Glycoprotein," *Journal of Virology*, vol. 79(17):11095-11104 (2005).
Schofield, Darren J. et al., "Human Monoclonal Antibodies That React With the E2 Glycoprotein of Hepatitis C Virus and Possess Neutralizing Activity," *Hepatology*, vol. 42:1055-1062 (2005).
Tarr, Alexander W. et al., "Characterization of the Hepatitis C Virus E2 Epitope Defined by the Broadly Neutralizing Monoclonal Antibody AP33," *Hepatology*, vol. 43:592-601 (2006).
Triyatni, Miriam et al., "Structural Features of Envelope Proteins on Hepatitis C Virus-like Particles as Determined by Anti-envelope Monoclonal Antibodies and CD81 Binding," *Virology*, vol. 298:124-132 (2002).
Zhou, Yi-Hua et al., "Monoclonal Antibodies to the Hypervariable Region 1 of Hepatitis C Virus Capture Virus and Inhibit Virus Adsorption to Susceptible Cells in Vitro," *Virology*, vol. 269:276-283 (2000).
Zucchelli, Silvia et al., "Mimotopes of the Hepatitis C Virus Hypervariable Region 1, but Not the Natural Sequences, Induce Cross-Reactive Antibody Response by Genetic Immunization," *Hepatology*, vol. 33:692-703 (2001).
International Search Report and Written Opinion for Application No. PCT/US2008/001922, dated Jul. 30, 2008.
Reply to Office Action submitted in Chinese Patent Application No. 200880010301.5, filed May 17, 2012 (English Language Translation Provided) (30 pages).
Second Office Action issued in Chinese Patent Application No. 200880010301.5, dated Aug. 15, 2012 (English Language Translation Provided) (12 pages).
Allander et al., "Recombinant Human Monoclonal Antibodies Against Different Conformational Epitopes of the E2 Envelope Glycoprotein of Hepatitis C Virus that Inhibit Its Interaction with CD81," *Journal of General Virology* 81:2451-2459 (2000).
Bartosch et al., "In Vitro Assay for Neutralizing Antibody to Hepatitis C Virus: Evidence for Broadly Conserved Neutralization Epitopes," *Proc. Natl. Acad. Sci. USA* 100:14199-14204 (2003).
Blair et al., "A Novel Human Monoclonal Antibody Directed Against the E2 Glycoprotein of Hepatitis C Virus (HCV) Prevents Infection in Chimpanzees," 44th Annual Meeting of the European Association for the Study of the Liver (EASL), Copenhagen, Denmark (2009) Poster #1048.
Broering et al., "Identification and Characterization of Broadly Neutralizing Human Monoclonal Antibodies Directed Against the E2 Envelope Glycoprotein of Hepatitis C Virus," *Journal of Virology* 83:12473-12482 (2009).
Bugli et al., "Mapping B-Cell Epitopes of Hepatitis C Virus E2 Glycoprotein Using Human Monoclonal Antibodies from Phage Display Libraries," *Journal of Virology* 75: 9986-9990 (2001).
Burioni et al., "Diverging Effects of Human Recombinant Anti-Hepatitis C Virus (HCV) Antibody Fragments Derived from a Single Patient on the Infectivity of a Vesicular Stomatitis Virus/HCV Pseudotype," *J. Virol.* 76:11775-11779 (2002).
Burioni et al., "Dissection of Human Humoral Immune Response Against Hepatitis C Virus E2 Glycoprotein by Repertoire Cloning and Generation of Recombinant Fab Fragments," *Hepatology* 28:810-814 (1998).
Choo et al., "Isolation of a cDNA Clone Derived from a Blood-Borne Non-A, Non-B Viral Hepatitis Genome," *Science* 244:359-362 (1989).
Davis et al., "A Randomized, Open-Label Study to Evaluate the Safety and Pharmacokinetics of Human Hepatitis C Immune Globulin (Civacir) in Liver Transplant Recipients," *Liver Transplantation* 11:941-949 (2005).
Farci et al., "Prevention of Hepatitis C Virus Infection in Chimpanzees by Hyperimmune Serum Against the Hypervariable Region 1 of the Envelope 2 Protein," *Proc. Natl. Acad. Sci. USA* 93:15394-15399 (1996).
Farci et al., "Prevention of Hepatitis C Virus Infection in Chimpanzees After Antibody-Mediated In Vitro Neutralization," *Proc. Natl. Acad. Sci. USA* 91:7792-7796 (1994).
Fishwild et al., "High-Avidity Human IgG kappa Monoclonal Antibodies from a Novel Strain of Minilocus Transgenic Mice," *Nature Biotechnology* 14:845-851 (1996).
Flint et al., "Characterization of Hepatitis C Virus E2 Glycoprotein Interaction with a Putative Cellular Receptor, CD81," *Journal of Virology* 73:6235-6244 (1999).
Gal-Tanamy et al., "In Vitro Selection of a Neutralization-Resistant Hepatitis C Virus Escape Mutant," *PNAS* 105:19450-19455 (2008).
Grollo et al., "Exploiting Information Inherent in Binding Sites of Virus-Specific Antibodies: Design of an HCV Vaccine Candidate Cross-Reactive with Multiple Genotypes," *Antiviral Therapy* 11:1005-1014 (2006).
Guha et al., "Cell Culture Models and Animal Models of Viral Hepatitis. Part II: Hepatitis C," *Lab Animal* 34:39-47 (2005).
Habersetzer et al., "Characterization of Human Monoclonal Antibodies Specific to the Hepatitis C Virus Glycoprotein E2 With In Vitro Binding Neutralization Properties," *Virology* 249:32-41 (1998).
Hadlock et al., "Human Monoclonal Antibodies that Inhibit Binding of Hepatitis C Virus E2 Protein to CD81 and Recognize Conserved Conformational Epitopes," *Journal of Virology* 74:10407-10416 (2000).
Johansson et al., "Human Combinatorial Libraries Yield Rare Antibodies that Broadly Neutralize Hepatitis C Virus," *PNAS* 104:16269-16274 (2007).
Krawczynski et al., "Effect of Immune Globulin on the Prevention of Experimental Hepatitis C Virus Infection," *The Journal of Infectious Diseases* 173:822-828 (1996).
Krawczynski et al., "Experimental Immune Treatment of HCV Infection—Passive Transfer of Anti-HCV in Chimpanzees," XI International Congress of Virology Meeting in Sydney, Australia, Aug. 9-13, 1999 (Abstract).
Lanford et al., "The Chimpanzee Model of Hepatitis C Virus Infections," *ILAR J.* 42:117-126 (2001).
Law et al., "Broadly Neutralizing Antibodies Protect Against Hepatitis C Virus Quasispecies Challenge," *Nature* 1-3 (Supplementary Figures) (2007).
Owsianka et al., "Monoclonal Antibody AP33 Defines a Broadly Neutralizing Epitope on the Hepatitis C Virus E2 Envelope Glycoprotein," *Journal of Virology* 79:11095-11104 (2005).

(56) References Cited

OTHER PUBLICATIONS

Owsianka et al., "Broadly Neutralizing Human Monoclonal Antibodies to the Hepatitis C Virus E2 Glycoprotein," *Journal of General Virology* 89:653-659 (2008).
Perotti et al., "Identification of a Broadly Cross-Reacting and Neutralizing Human Monoclonal Antibody Directed Against the Hepatitis C Virus E2 Protein," *Journal of Virology* 82:1047-1052 (2008).
Schiano et al., "Monoclonal Antibody HCV-$AB^{XTL}$68 in Patients Undergoing Liver Transplantation for HCV: Results of a Phase 2 Randomized Study," *Liver Transplantation* 12:1381-1389 (2006).
Schofield et al., "Human Monoclonal Antibodies that React with the E2 Glycoprotein of Hepatitis C Virus and Possess Neutralizing Activity," *Hepatology* 42:1055-1062 (2005).
Simmonds, "Variability of Hepatitis C Virus," *Hepatology* 21:570-583 (1995).
Tarr et al., "Determination of the Human Antibody Response to the Epitope Defined by the Hepatitis C Virus-Neutralizing Monoclonal Antibody AP33," *J. Gen. Virol.* 88:2991-3001 (2007).
Tarr et al., "Characterization of the Hepatitis C Virus E2 Epitope Defined by the Broadly Neutralizing Monoclonal Antibody AP33," *Hepatology* 43:592-601 (2006).
Triyatni et al., "Structural Features of Envelope Proteins on Hepatitis C Virus-Like Particles as Determined by Anti-Envelope Monoclonal Antibodies and CD81 Binding," *Virology* 298:124-132 (2002).
Willems et al., "Anti-HCV Human Immunoglobulins for the Prevention of Graft Infection in HCV-Related Liver Transplantation, A Pilot Study," Abstract #96 (2002).
Yu et al., "Neutralizing Antibodies to Hepatitis C Virus (HCV) in Immune Globulins Derived from Anti-HCV-Positive Plasma," *PNAS* 101:7705-7710 (2004).
Zhou et al., "Monoclonal Antibodies to the Hypervariable Region 1 of Hepatitis C Virus Capture Virus and Inhibit Virus Adsorption to Susceptible Cells In Vitro," *Virology* 269:276-283 (2000).
Zucchelli et al., "Mimotopes of the Hepatitis C Virus Hypervariable Region 1, but Not the Natural Sequences, Induce Cross-Reactive Antibody Response by Genetic Immunization," *Hepatology* 33:692-703 (2001).
International Preliminary Report on Patentability (PCT/US2008/001922) issued Aug. 26, 2009.
International Search Report (PCT/US2008/001922) mailed Jul. 30, 2008.
Written Opinion of the International Searching Authority (PCT/US2008/001922) dated Aug. 21, 2009.
First European Examination Report (Application No. 08725537.8) dated Nov. 24, 2009.
Second European Examination Report (Application No. 08725537.8) dated Nov. 25, 2010.
English Language Translation of Notice of Reasons for Rejection issued in Japanese Patent Application No. 2009-550888, dated Dec. 17, 2012, mailed Dec. 21, 2012 (5 pages).
Decision of Final Rejection of the Application issued in Chinese Patent Application No. 200880010301.5, dated Mar. 8, 2013 (English Language Translation Provided) (12 pages).

* cited by examiner

Genotype 1 soluble E2 ELISA. ELISA plates were coated with 2 µg/ml of 1a E2-660 (triangles) or 1b E2-661 (squares) and probed with HuMabs 95-2 and 83-128 in two-fold dilutions. Bound antibody was detected with goat-anti-human secondary antibody conjugated to alkaline phosphatase and PNPP substrate.

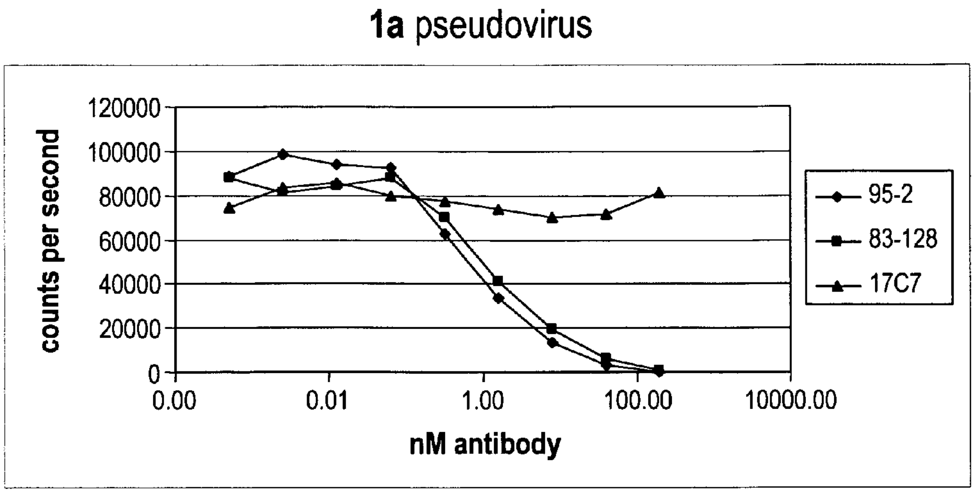

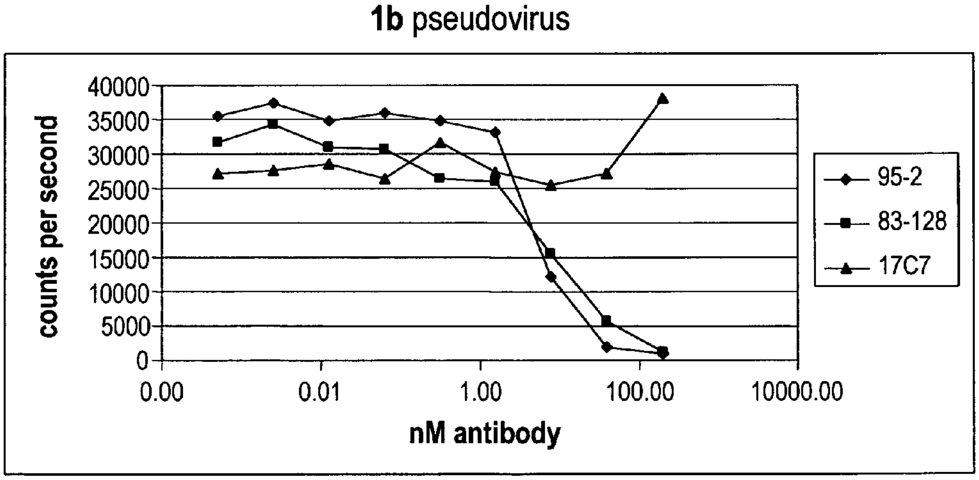

HCV genotype 1a and 1b pseudovirus neutralization. Five-fold dilutions of HuMabs 95-2, 83-128, and 17C7 (rabies HuMab, negative control) were incubated with HCV pseudovirus for 1 hr at room temperature. The virus-antibody mixture was added to Hep3B cells followed by incubation at 37°C for 72 hrs. Infection was quantitated with Brightglo luciferase assay and read in a Victor3 plate reader for light output.

*Fig. 2A*

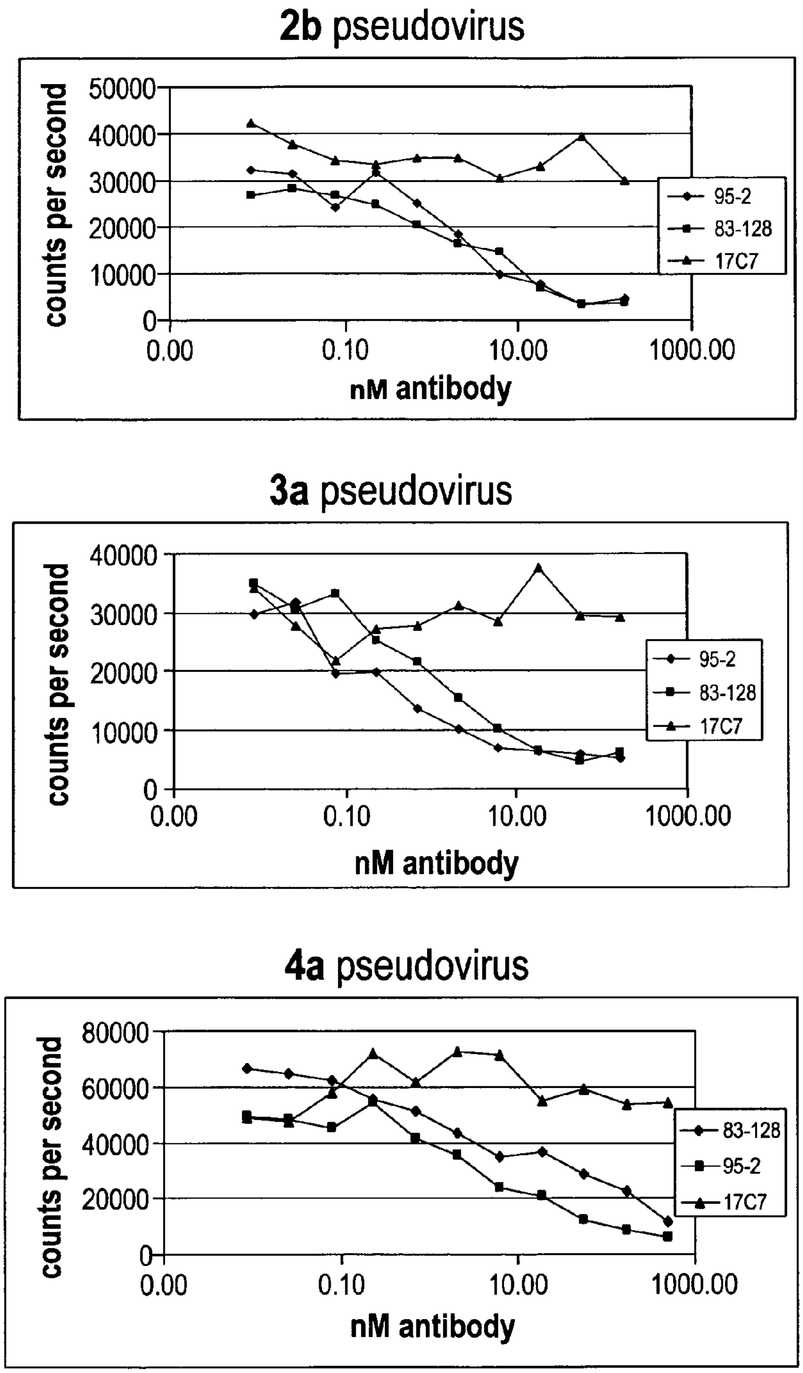

HCV genotype 2b, 3a and 4a pseudovirus neutralization. Five-fold dilutions of HuMabs 95-2, 83-128, and 17C7 (rabies HuMab, negative control) were incubated with HCV pseudovirus for 1 hr at room temperature. The virus-antibody mixture was added to Hep3B cells followed by incubation at 37°C for 72 hrs. Infection was quantitated with Brightglo luciferase assay and read in a Victor3 plate reader for light output.

*Fig. 2B*

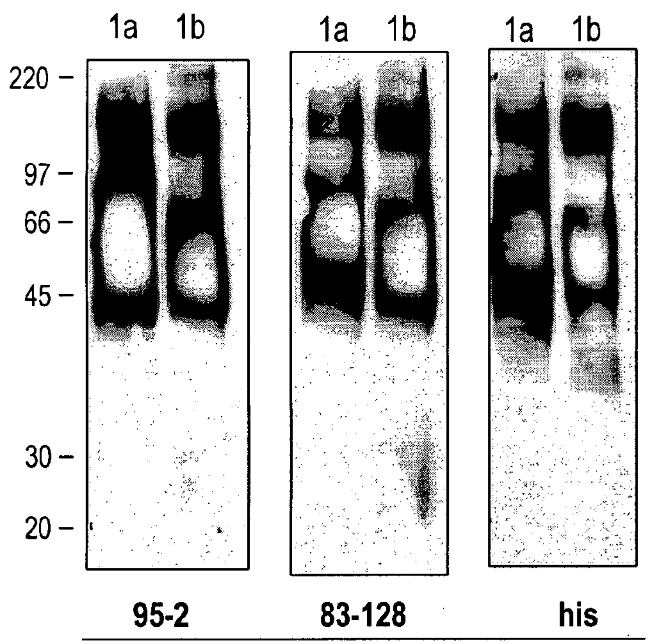

Figure 3A: Reduced

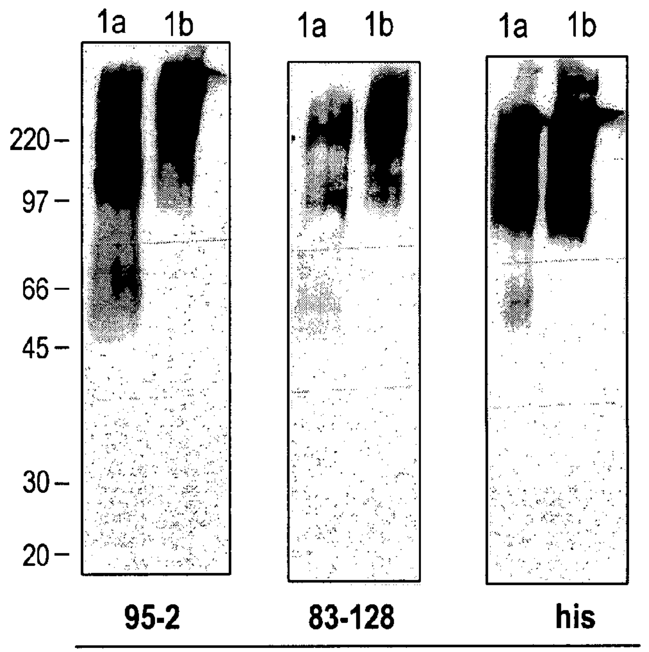

Figure 3B: Non-Reduced

Reducing and non-reducing Western blots of genotype 1a and 1b E2 soluble protein. Purified soluble mammalian expressed E2 protein (E2-661) from genotype 1a and 1b was subjected to reducing or non-reducing SDS-PAGE followed by transfer to PVDF membrane. Westerns blots were performed with anti-his tag monoclonal (his), 83-128 and 95-2 using anti-mouse IgG (his) or anti-human IgG (95-2 and 83-128) conjugated to HRP with enhanced chemiluminescent detection reagent. The genotype of the soluble E2 is indicated above the blots. The primary antibody used for detection is listed below the blots. The molecular weight markers in kilodaltons is listed to the left of each set of blots.

*Fig. 3*

| | ka (1/Ms) | kd (1/s) | KD (M) |
|---|---|---|---|
| 95-2 | 1.6e5 | 3.0e-4 | 1.9e-9 |
| 83-128 | 1.9e5 | 7.3e-4 | 3.8e-9 |

95-2 and 83-128 affinity determination for E2 412-423 epitope expressed as a bacterial fusion protein. Goat anti-human IgG Fc was amide coupled to the Biacore chip. 95-2 and 83-128 were separately captured on the chip and E2-G bacterially expressed protein containing E2 412-423 amino acids was flowed over at varying concentrations. The BIAevaluation software was used to fit the curves and calculate the affinity constants.

*Fig. 4*

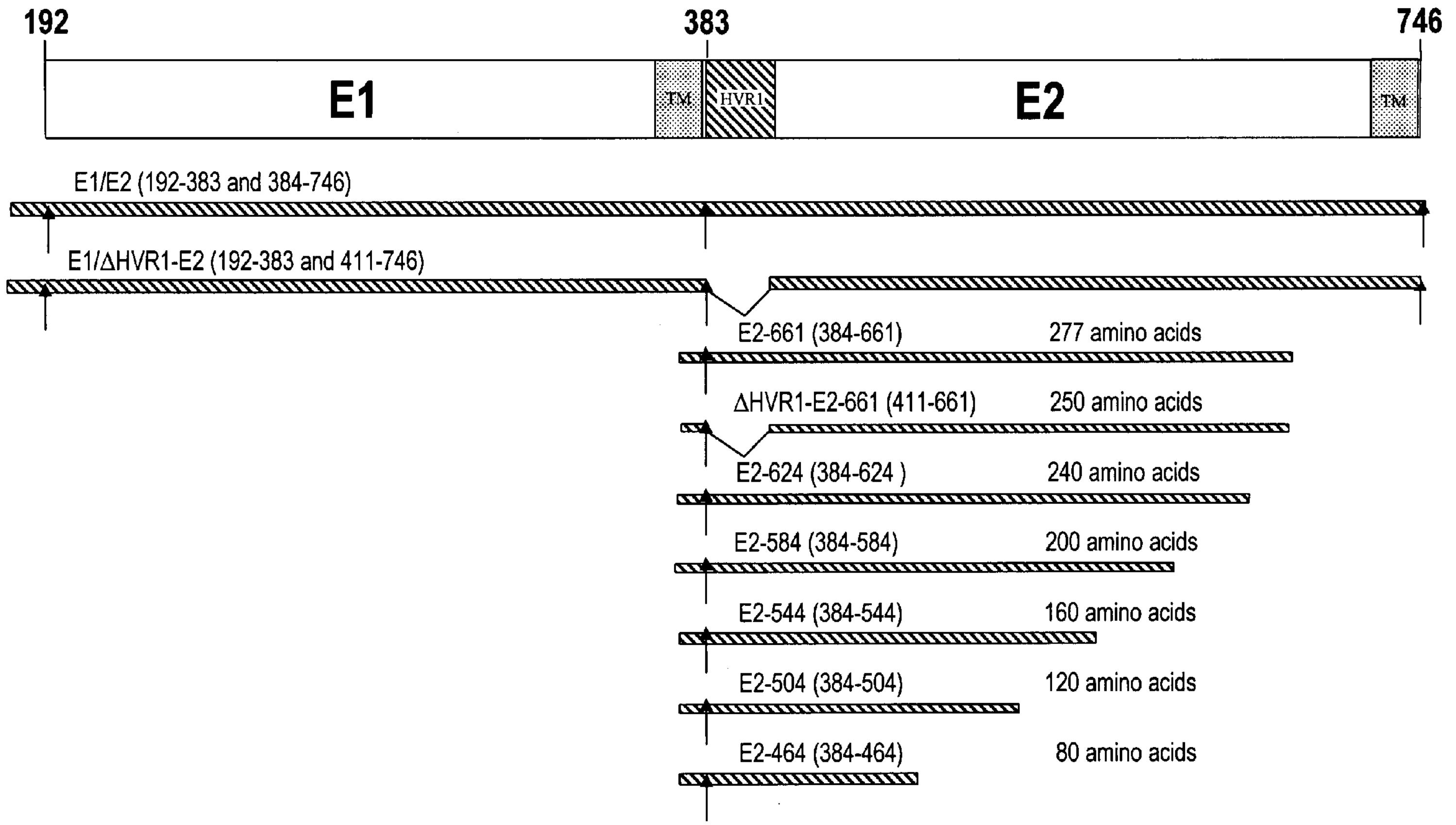

E1 and E2 mammalian expressed proteins. The E1 and E2 polyprotein is indicated at top by a long white box with amino acid numbers noted above. The transmembrane domains (TM) are indicated by light grey boxes and the hypervariable domain 1 (HVR1) of E2 is indicated by a dark grey box. The mammalian proteins expressed from engineered constructs are listed below as dark grey bars. Sites of signal peptidase cleavage are indicated by arrows. The name of each protein is followed by the encoded amino acids in parenthesis and total amino acids in the expressed protein

*Fig. 5*

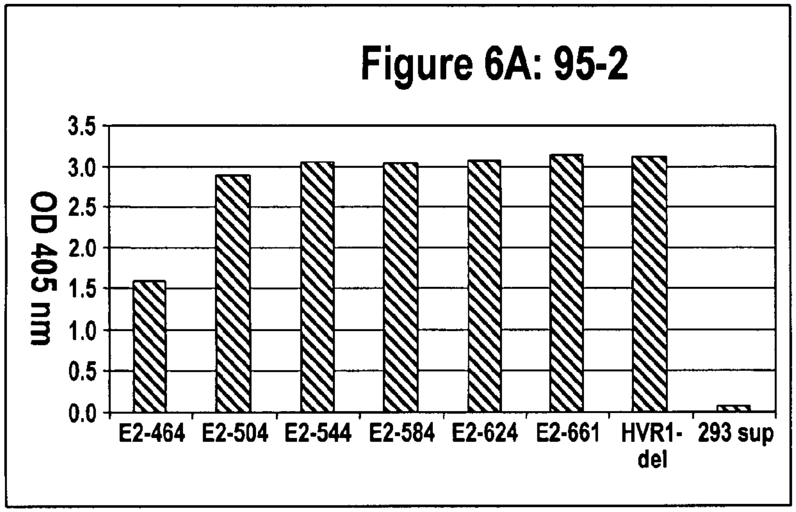

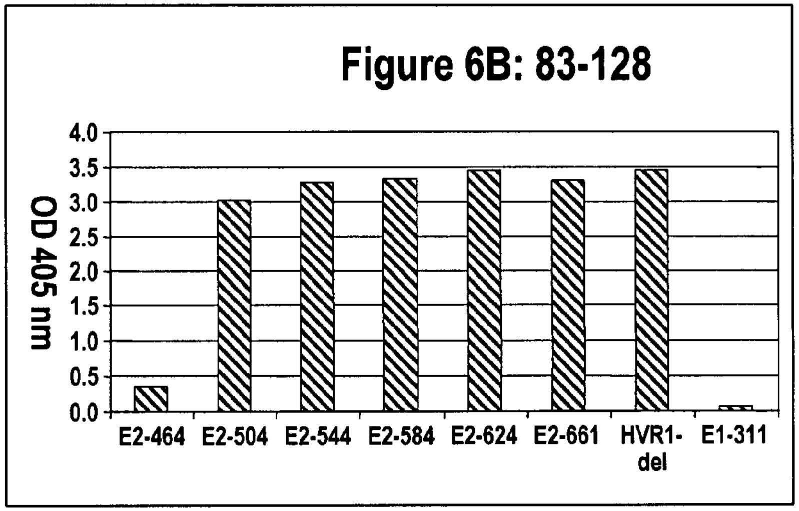

Lectin capture ELISA of mammalian expressed C-terminal truncations of E2. Cell culture supernatants containing mammalian expressed C-terminal truncations of E2, fusion proteins containing E2 amino acids indicated in figure 7 were coated on an ELISA plate and probed with two-fold dilutions of HuMabs 95-2 and 83-128 and mouse six histidine tag antibody (his tag). Bound antibodies were detected with goat-anti-human (95-2 and 83-128) or goat-anti-mouse (his tag) conjugated to alkaline phosphatase and PNPP substrate.

*Fig. 6*

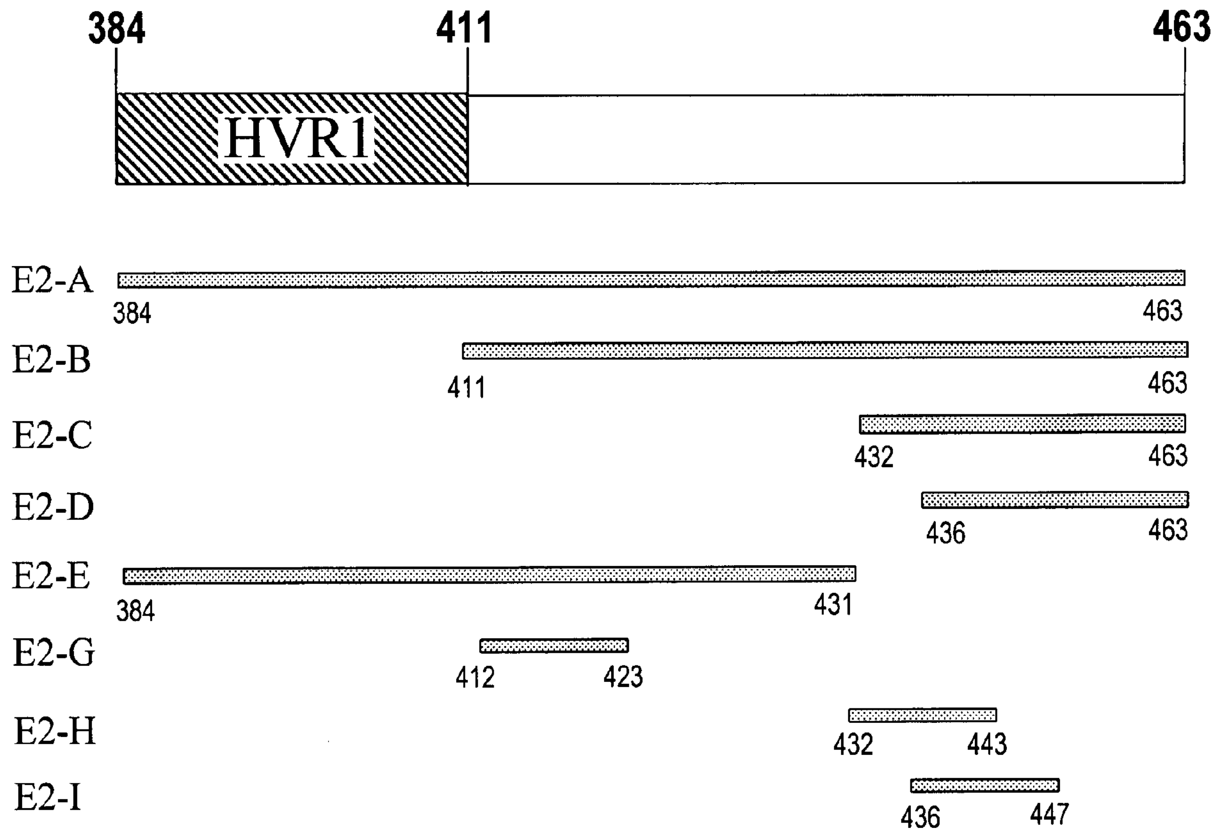

Bacterially expressed proteins spanning the amino-terminal 80 amino acids of E2. The first 80 amino acids of the E2 protein are represented at top by a white box with the amino acids numbers above. The 27 amino acid hypervariable region 1 (HVR1) at the amino-terminus is indicated by a dark grey box. The proteins expressed from engineered constructs are indicated by light grey bars with names to the left of the bar and amino acid numbers for the start and end of the protein listed below the bar.

*Fig. 7*

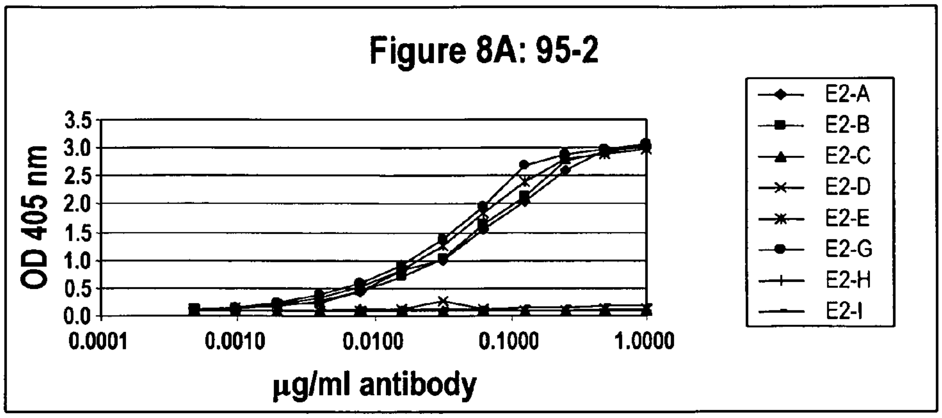

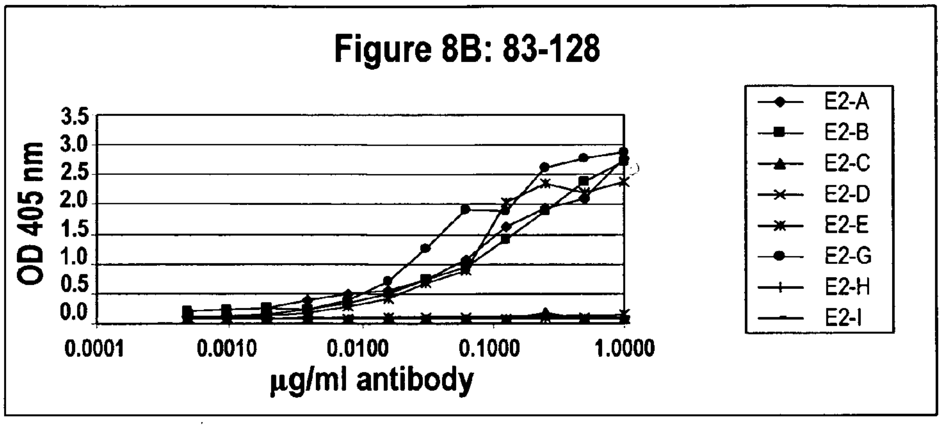

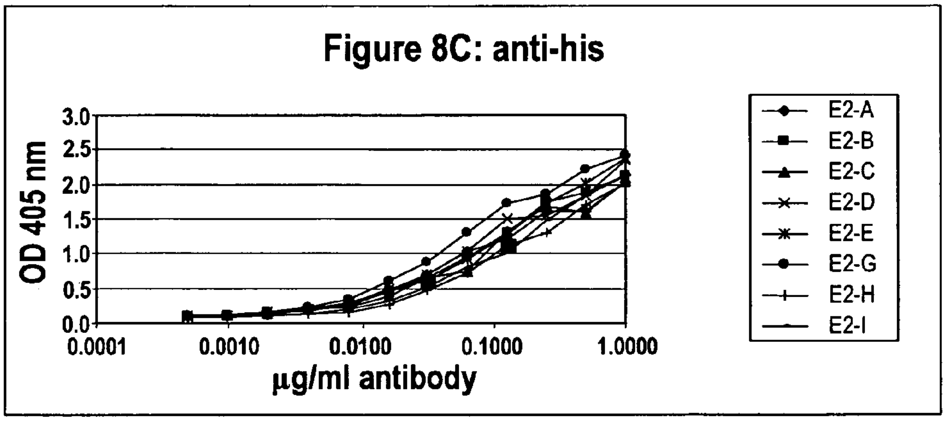

ELISA of bacterially expressed pieces of E2 first 80 amino acids. Bacterially expressed fusion proteins containing E2 amino acids indicated in figure 7 were coated on an ELISA plate and probed with two-fold dilutions of HuMabs 95-2 and 83-128 and mouse six histidine tag antibody (his tag). Bound antibodies were detected with goat-anti-human (95-2 and 83-128) or goat-anti-mouse (his tag) conjugated to alkaline phosphatase and PNPP substrate.

*Fig. 8*

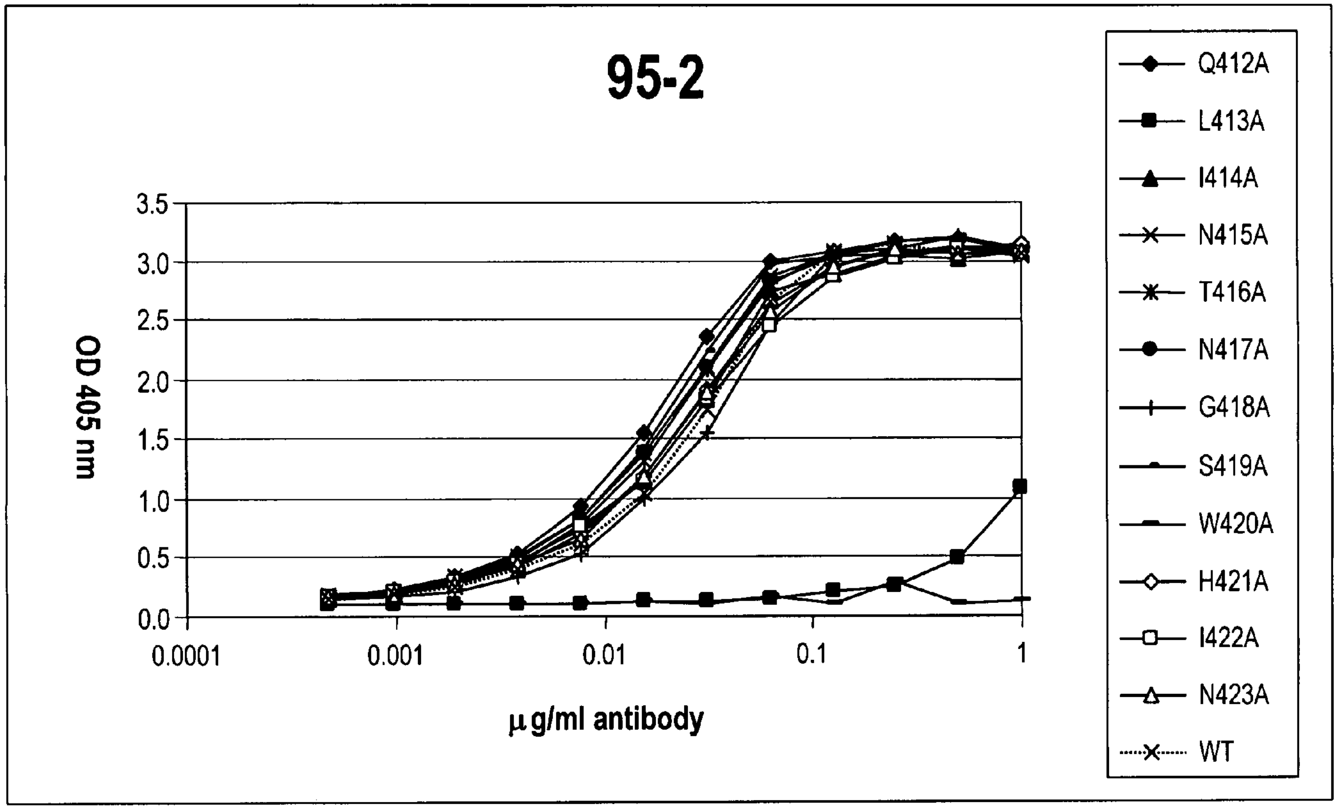

ELISA of E2-412-423 alanine scanning mutants. Bacterially expressed fusion proteins containing E2 amino acids 412-423 with the indicated amino acids mutated to an alanine or containing no mutantions (WT) were coated on an ELISA plate and probed with two-fold dilutions of HuMabs 95-2 and 83-128 and mouse six histidine tag antibody (his tag). Bound antibodies were detected with goat-anti-human (95-2 and 83-128) or goat-anti-mouse (his tag) conjugated to alkaline phosphatase and PNPP substrate.

*Fig. 9A*

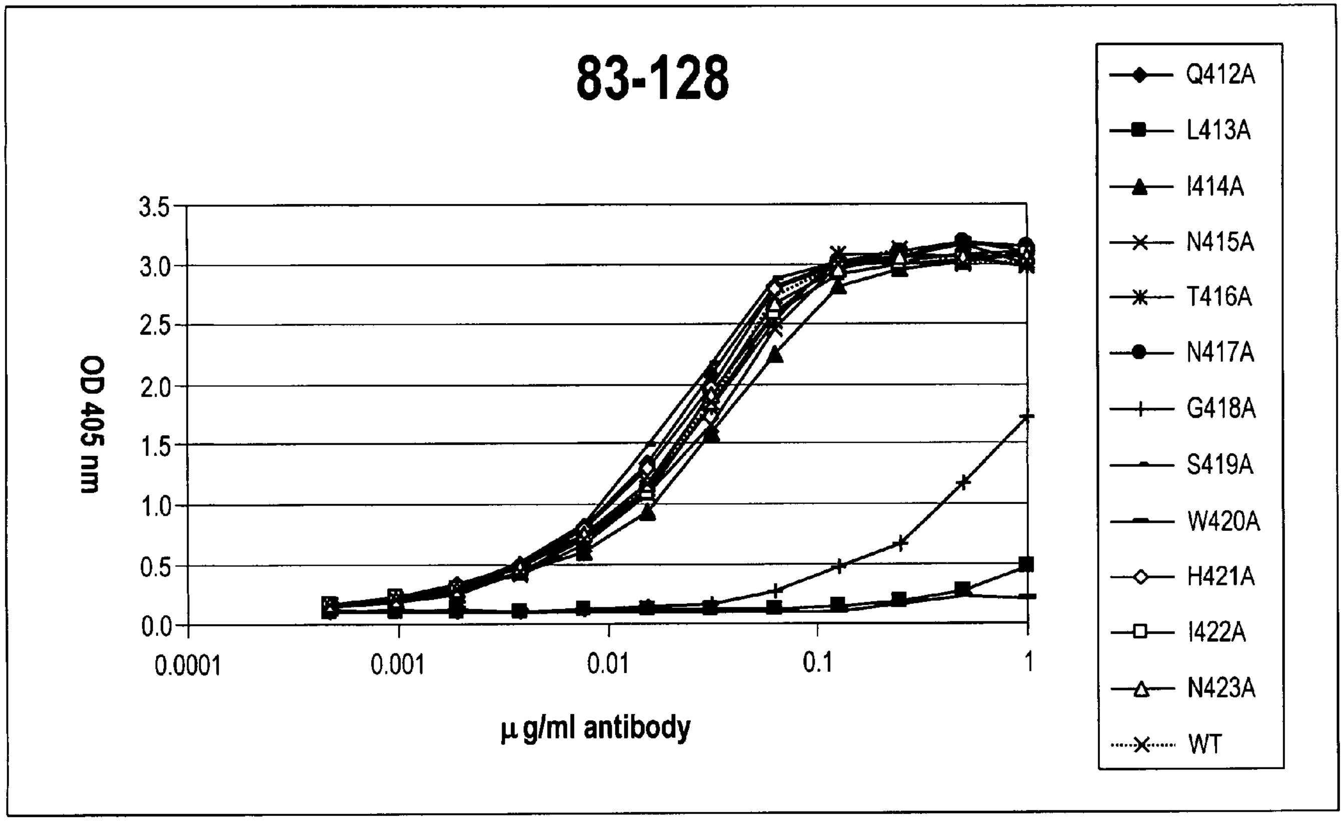

ELISA of E2-412-423 alanine scanning mutants. Bacterially expressed fusion proteins containing E2 amino acids 412-423 with the indicated amino acids mutated to an alanine or containing no mutantions (WT) were coated on an ELISA plate and probed with two-fold dilutions of HuMabs 95-2 and 83-128 and mouse six histidine tag antibody (his tag). Bound antibodies were detected with goat-anti-human (95-2 and 83-128) or goat-anti-mouse (his tag) conjugated to alkaline phosphatase and PNPP substrate.

*Fig. 9B*

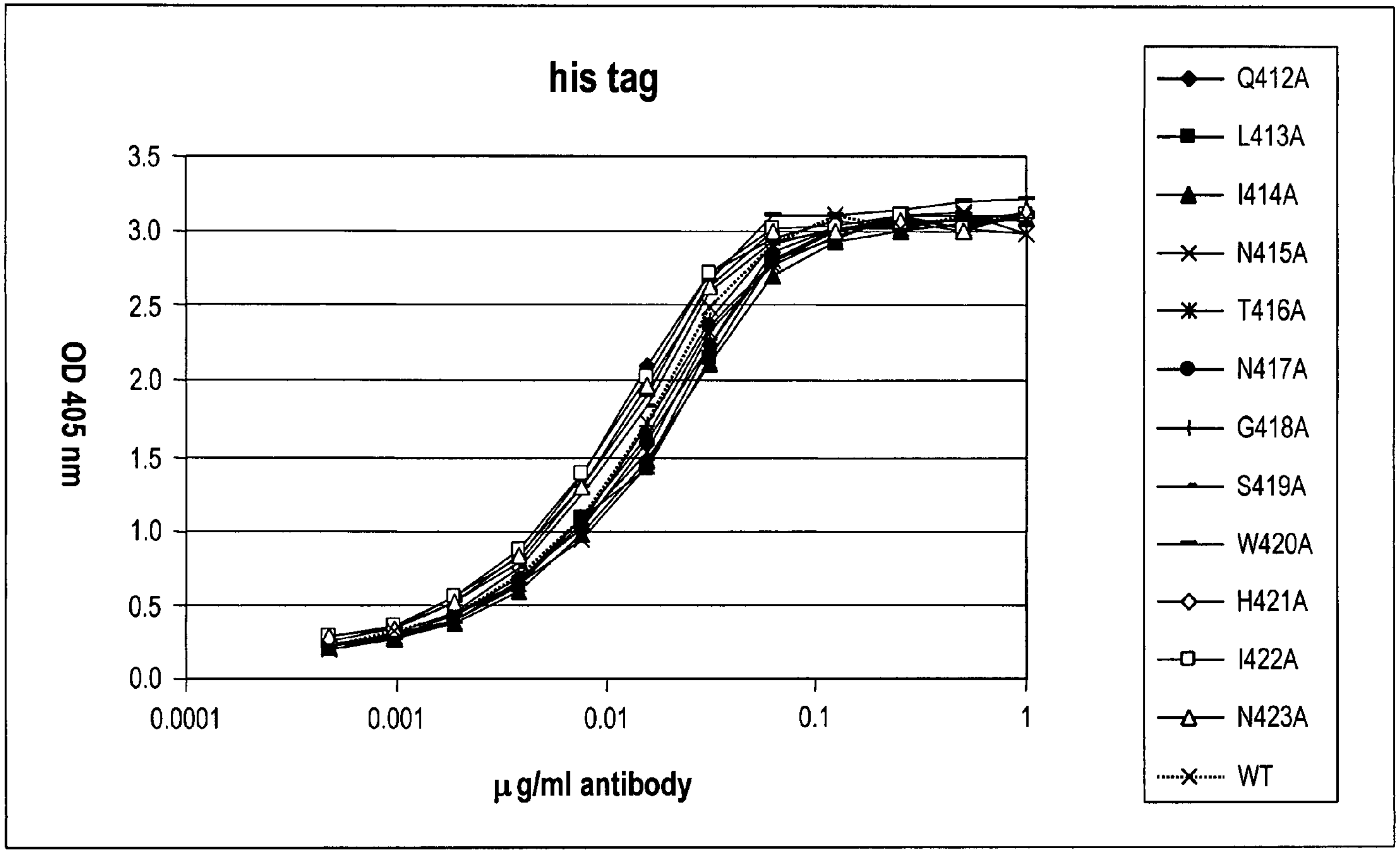

ELISA of E2-412-423 alanine scanning mutants. Bacterially expressed fusion proteins containing E2 amino acids 412-423 with the indicated amino acids mutated to an alanine or containing no mutantions (WT) were coated on an ELISA plate and probed with two-fold dilutions of HuMabs 95-2 and 83-128 and mouse six histidine tag antibody (his tag). Bound antibodies were detected with goat-anti-human (95-2 and 83-128) or goat-anti-mouse (his tag) conjugated to alkaline phosphatase and PNPP substrate.

| Sequence | | | Count | Percent |
|---|---|---|---|---|
| QLINTNGSWHIN | (1a) | (SEQ ID NO:59) | 78 | 48.1 |
| --V--------- | (1b) | (SEQ ID NO:60) | 48 | 29.6 |
| --V-S------- | | (SEQ ID NO:61) | 8 | 4.9 |
| ----S------- | | (SEQ ID NO:62) | 5 | 3.1 |
| H----------- | | (SEQ ID NO:63) | 4 | 2.5 |
| ---K-------- | | (SEQ ID NO:64) | 3 | 1.9 |
| --V-------V- | | (SEQ ID NO:65) | 1 | 0.6 |
| -FV--------- | | (SEQ ID NO:66) | 1 | 0.6 |
| ---KNGS----- | | (SEQ ID NO:67) | 1 | 0.6 |
| --VK-------- | | (SEQ ID NO:68) | 1 | 0.6 |
| H-V--------- | | (SEQ ID NO:69) | 1 | 0.6 |
| H-V-S------- | | (SEQ ID NO:70) | 1 | 0.6 |
| ---H-------- | | (SEQ ID NO:71) | 1 | 0.6 |
| --VK-E-N---- | | (SEQ ID NO:72) | 1 | 0.6 |
| N--K-------- | | (SEQ ID NO:73) | 1 | 0.6 |
| ---Y-------- | | (SEQ ID NO:74) | 1 | 0.6 |
| ----------L- | | (SEQ ID NO:75) | 1 | 0.6 |
| Y----------- | | (SEQ ID NO:76) | 1 | 0.6 |
| S----------- | | (SEQ ID NO:77) | 1 | 0.6 |
| N----------- | | (SEQ ID NO:78) | 1 | 0.6 |

Total sequences = 160

Number of variants = 20

E2 amino acids 412-423 alignments from the Los Alamos HCV Sequence Database supported by NIH. The one letter amino acid code for the prototype genotype 1a sequence for amino acids 412-423 are listed at the top of chart in red (1a). Any amino acids that are identical to the 1a sequence are indicated with a dash and the amino acid listed for any position that is different from the prototype genotype 1a sequence. The number of times that this 12 amino acid sequence is found in the condensed database is listed under count and the percent of the total is listed under percent. The sequences of our 1a and 1b soluble E2 proteins are in red.

E2 amino acids 412-423 from other genotypes. The one-letter amino acid code for amino acids 412-423 are listed for isolates that contained changes (red underline) from the prototype genotype 1a sequence. The genotype name is listed to the right followed by the genbank accession number in parenthesis.

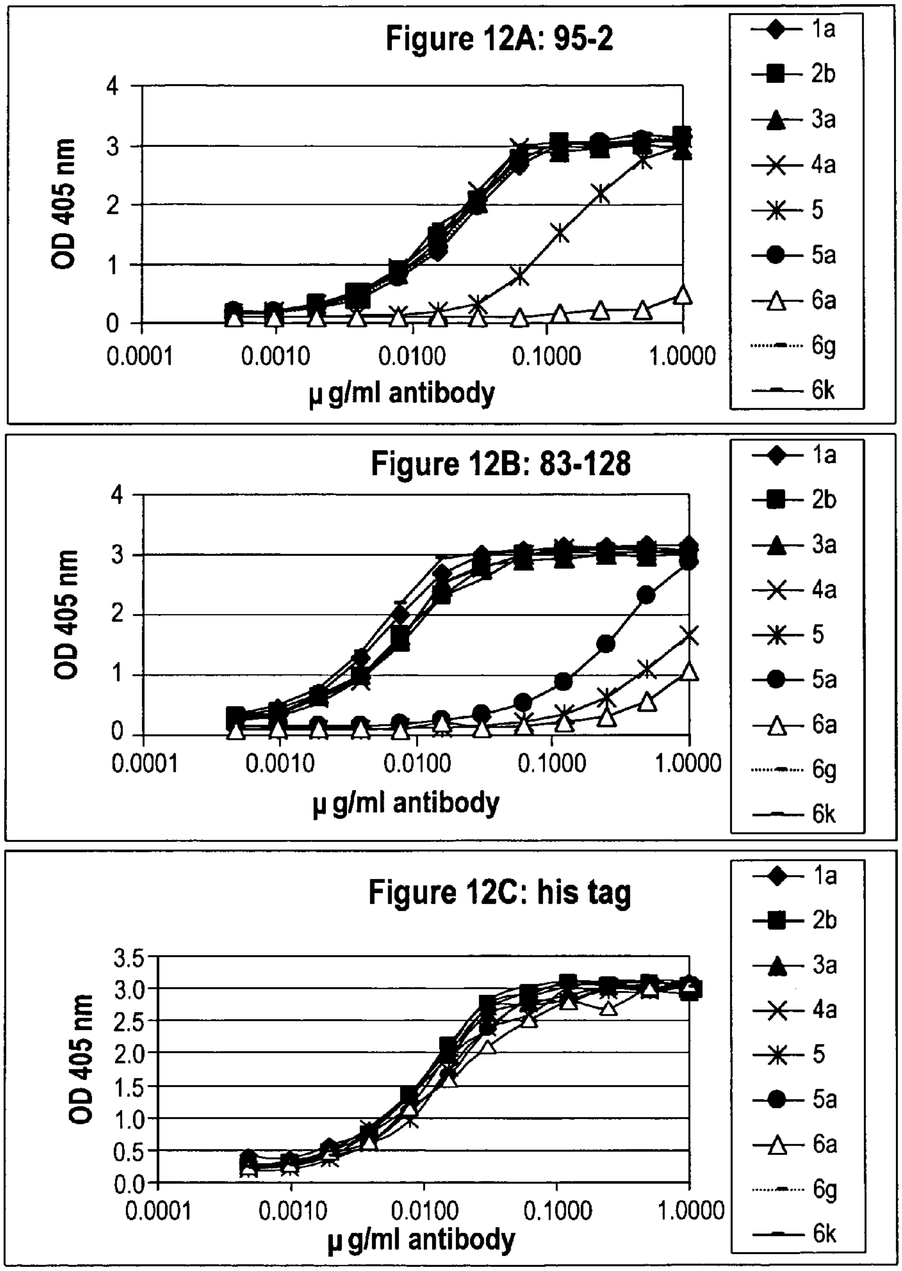

ELISA of E2 amino acids 412-423 from other genotypes. Bacterially expressed fusion proteins containing E2 amino acids 412-423 with the sequence from the indicated genotype were coated on an ELISA plate and probed with two-fold dilutions of HuMabs 95-2 and 83-128 and mouse six histidine tag antibody (his tag). Bound antibodies were detected with goat-anti-human (95-2 and 83-128) or goat-anti-mouse (his tag) conjugated to alkaline phosphatase and PNPP substrate.

*Fig. 12*

E1/E2 codon optimized 1a H77 sequence with added ends containing restrictions sites (bold lowercase), additional overhangs to insure restriction enzyme cutting (underlined lowercase), and consensus Kozak sequence (bold underlined lowercase) with ATG initiation codon (bold underlined uppercase) (SEQ ID NO:31)

cgctatagaagcttgccgccaccATGGCCACCGGCAACCTGCCCGGCTGCTCCTTC
TCCATCTTCCTGCTGGCCCTGCTGTCCTGCCTGACCGTGCCCGCCTCCGCCTACCAGGTGC
GCAACTCCTCCGGCCTGTACCACGTGACCAACGACTGCCCTAACTCCTCCATCGTGTACGA
GGCCGCCGACGCCATCCTGCACACTCCTGGCTGCGTGCCCTGCGTGCGCGAGGGCAACGCC
TCCCGCTGCTGGGTGGCCGTGACTCCTACCGTGGCCACCCGCGACGGCAAGCTGCCCACCA
CCCAGCTGCGCCGCCACATCGACCTGCTGGTGGGCTCCGCCACCCTGTGCTCCGCCCTGTA
CGTGGGCGACCTGTGCGGCTCCGTGTTCCTGGTGGGCCAGCTGTTCACCTTCTCTCCTCGC
CGCCACTGGACCACCCAGGACTGCAACTGCTCCATCTACCCTGGCCACATCACCGGCCACC
GCATGGCCTGGGACATGATGATGAACTGGTCTCCCACCGCCGCCCTGGTGGTGGCCCAGCT
GCTGCGCATCCCTCAGGCCATCATGGACATGATCGCCGGCGCCCACTGGGGCGTCCTGGCC
GGCATCGCCTACTTCTCCATGGTGGGCAACTGGGCCAAGGTGCTGGTGGTGCTGCTGCTGT
TCGCCGGCGTGGACGCCGAGACCCACGTGACGGGCGGCTCCGCCGGCCGCACCACCGCCGG
CCTGGTGGGCCTGCTGACACCCGGCGCCAAGCAGAACATCCAGCTGATCAACACCAACGGC
TCCTGGCACATCAACTCCACCGCCCTGAACTGCAACGAGTCCCTGAACACCGGCTGGCTGG
CCGGCCTGTTCTACCAGCACAAGTTCAACTCCTCCGGCTGTCCCGAGCGCCTGGCCTCCTG
CCGCCGCCTGACCGACTTCGCCCAGGGCTGGGGCCCTATCTCCTACGCCAACGGCTCCGGC
CTGGACGAGCGGCCCTACTGCTGGCACTACCCTCCTCGCCCTTGCGGCATCGTGCCCGCCA
AGTCCGTGTGCGGCCCTGTGTACTGCTTCACTCCCTCTCCCGTGGTGGTGGGCACCACCGA
CCGCTCCGGCGCTCCCACCTACTCCTGGGGCGCCAACGACACCGACGTGTTCGTGCTGAAC
AACACCCGCCCTCCTCTGGGCAACTGGTTCGGCTGCACCTGGATGAACTCCACCGGCTTCA
CCAAGGTGTGCGGCGCGCCTCCCTGCGTGATCGGCGGCGTGGGCAACAACACCCTGCTGTG
CCCTACCGACTGCTTCCGCAAGCATCCCGAGGCCACCTACTCCCGCTGCGGCTCCGGCCC
TGGATCACTCCTCGCTGCATGGTGGACTATCCCTACCGCCTGTGGCACTATCCCTGCACCA
TCAACTACACCATCTTCAAGGTGCGCATGTACGTGGGCGGCGTGGAGCACCGCCTGGAGGC
GGCGTGCAACTGGACCCGCGGCGAGCGCTGCGACCTGGAGGACCGCGACCGCTCCGAGCTG
TCTCCTCTGCTGCTGTCCACCACCCAGTGGCAGGTGCTGCCCTGCTCCTTCACCACCCTGC
CCGCGCTGTCCACCGGCCTGATCCACCTGCACCAGAACATCGTGGACGTGCAGTACCTGTA
CGGCGTGGGCTCCTCCATCGCGTCCTGGGCGATCAAGTGGGAGTACGTGGTGCTGCTGTTC
CTGCTGCTGGCGGACGCGCGCGTGTGCTCCTGCCTGTGGATGATGCTGCTGATCTCCCAGG
CGGAGGCGtctagaggagtca

*Fig. 13*

ALIGNMENT AND CONSENSUS SEQUENCE FOR MONOCLONAL ANTIBODIES REACTIVE AGAINST EPITOPE 412-423 OF E2-660 HCV GLYCOPROTEIN Germ line: VH3-33, D3-10, JH4; Vk-L6, Jk5

Heavy Chain Amino Acid Alignment

```
95-43  (SEQ ID NO:36)    QVQLVESGGGVVQPGRSLRLSCAASGFTFSSYGMHWVRQAPGKGLEWVAVIWFDGNNKYY
95-54   (38)             QVQLVESGGGVVQPGRSLRLSCAASGFTFSSYGMHWVRQAPGKGLEWVAVIWFDGNNKYY
95-25   (34)             QVQLVESGGGVVQPGRSLRLSCAASGFTFSNYGMHWVRQAPGKGLEWVAVIWFDGNNKYY
95-14   (32)             QVQLVESGGGVVQPGRSLRLSCAASGFILSSYGMHWVRQAPGKGLEWVAVIWYDGNNKYY
95-49   (37)             QVQLVESGGGVVQPGRSLRLSCAASGFTLSSYGMHWVRQAPGKGLEWVAVIWYDGNNKYY
95-62   (40)             QVQLVESGGGVVQPGRSLRLSCAASGFTLSSYGMHWVRQAPGKGLEWMAVIWYDGNNKYY
95-42   (35)             QVQLVESGGGVVQPGRSLRLSCAASGFTFSSYGMHWVRQAPGKGLEWVAVIWYDESNKYY
95-58   (39)             QVQLVESGGGVVQPGRSLRLSCAASGFTFSSYGMHWVRQAPGKGLEWVAVIWYDENNKYY
95-2    (3)              QVQLVESGGGVVQPGRSLRLSCAASGFTFSSYGMHWVRQAPGKGLEWVAVIWFDGNNQYY
95-38   (33)             QVQLVESGGGVVQPGRSLRLSCAASGFTFSSYGMHWVRQAPGKGLEWVAVIWLDGSNTYY
83-128  (1)              QVQLVESGGGVVQPGRSLRLSCTASGFTFNNYGMHWVRQTPGKGLEWLAVIWFDENNKYY
                         **********************:*****:..********:*******:**** * .* **

95-43                    ADSMKGRFTISRDNSKNTLYLQMNSLRAEDTAVYYCARDIFTMVRGVFIYFDYWGQGT
95-54                    ADSVKGRFTISRDNSKNTLYLQMNSLRAEDTAVYYCARDIFTMVRGVFIYFDYWGQGT
95-25                    ADSVKGRFTISRDNSKNTLYLQMNSLRAEDTAVYYCARDIFTMDRGVFIYFDYWGQGT
95-14                    ADSVKGRFTISRDNSKNTLYLQMNSLRAEDTAVYYCARDIFTMVRGVFIYFDYWGQGT
95-49                    ADSVKGRFTISRDNSKNTLYLQMDSLRAEDTAVYYCARDIFTMVRGVFIYFDYWGQGT
95-62                    ADSVKGRFTISRDNSKNTLYLQMNSLRAEDTAVYYCARDIFTMVRGVFIYFDYWGQGT
95-42                    ADSVKGRFTISRDNSKNTLYLQMNSLRAEDTAVYYCARDIFTMVRGVFIYFDYWGQGT
95-58                    ADSVKGRFTISRDNSNNTLYLQMNSLRAEDTAVYYCARDIFTMVRGVFIYFDYWGQGT
95-2                     ADSVKGRFTISRDNSKNTLYLQMNSLRAEDTAVYYCARDIFTVVRGFFIYFDYWGQGT
95-38                    ADSVKGRFTISRDNSKNTLFLQMNSLRAEDTAVYYCARDIFTVARGVIIYFDYWGQGT
83-128                   ADSVRGRFTISRDNSKNTLFLQMNSLKTEDTAMYYCARDI-SLVRDAFIYFDFWGLGT
                         ***::********************::****:*******  ::.*..:****:** **

95-43                    LVTVSS
95-54                    LVTVSS
95-25                    LVTVSS
95-14                    LVTVSS
95-49                    LVTVSS
95-62                    LVTVSS
95-42                    LVTVSS
95-58                    LVTVSS
95-2                     LVTVSS
95-38                    LVTVSS
83-128                   LVTVSS
                         ******
```

*Fig. 14*

Light Chain Amino Acid Alignments

| | | |
|---|---|---|
| 073-1 | (SEQ ID NO: 6) | EIVLTQSPATLSLSPGERATLSC**RASQSVSSYLA**WYQQKPGQAPRLLIY**DASNRAT**GIPA |
| 95-38 | (53) | EIVLTQSPATLSLSPGERATLSC**RASQSVSSYLA**WYQQKPGQAPRLLIY**DASNRAT**GIPA |
| 95-2 | (4) | EIVLTQSPATLSLSPGERATLSC**RASQSVGSYLA**WYQQKPGQAPRLLIY**DASNRAT**GIPA |
| 95-14 | (44) | EIVLTQSPATLSLSPGERATLSC**RASQSVGSYLA**WYQQKPGQAPRLLIY**DASNRAT**GIPA |
| 83-128 | (2) | EIVLTQSPATLSLSPGERATLSC**RASQSVSSYLA**WYQQKPGQAPRLLIY**DASNRAT**GIPA |
| | | *****************************.****************************** |

| | |
|---|---|
| 073-1 | RFSGSGSGTDFTLTISTLEPEDFAVYYC**QQRSNWVT**FGQGTRLEIK |
| 95-38 | RFSGSGSGTDFTLTISSLEPEDFAVYYC**QQRSNWVT**FGQGTRLEIK |
| 95-2 | RFSGSGSGTDFTLTISSLEPEDFAVYYC**QQRSNWVT**FGQGTRLEIK |
| 95-14 | RFSGSGSGTDFTLTISSLEPEDFAVYYC**QQRSNWVT**FGQGTRLEIK |
| 83-128 | RFSGSGSGTDFTLTISSLEPEDFAVYYC**QQRSNWIT**FGQGTRLEIK |
| | ****************:*****************:*********** |

*Fig. 15*

HUMAN ANTIBODIES AGAINST HEPATITIS C VIRUS (HCV) AND USES THEREOF

RELATED APPLICATIONS

This application claims priority to and the benefit of U.S. Provisional Patent Application No. 60/902,432, filed Feb. 21, 2007, for all subject matter common to said application. The disclosure of the above-mentioned application is hereby incorporated by reference herein in its entirety.

BACKGROUND OF THE INVENTION

Hepatitis C virus (HCV), originally named "non-A non-B hepatitis" (NANBH), is a positive, single-stranded RNA virus of the Flaviviridae family. Its genome contains a single long open reading frame which encodes a polyprotein of about three-thousand amino acid residues. (Choo et al. (1989) Science 244:359-362). The polyprotein is processed by the host cell and viral proteases into three major structural proteins and several non-structural proteins necessary for viral replication. The nucleotide sequence of HCV is highly variable, the most divergent isolates sharing only 60% nucleotide sequence homology. Several different genotypes of HCV with slightly different genomic sequences have been identified.

Isolates from all over the world have now been grouped into 6 main types, each with several subtypes, based on sequence data (Simmonds et al. (1995) Hepatology 21: 570-83). Types 1-3 account for almost all infections in Europe, type 4 is prevalent in Egypt and Zaire, type 5 in South Africa and type 6 in Hong Kong.

The virus is transmitted primarily by blood and blood products. The majority of infected individuals have either received blood transfusions prior to 1990 (when screening of the blood supply for HCV was implemented) or have used intravenous drugs. Approximately 200 to 400 million people worldwide are chronically infected with HCV, about 2 to 5 million of these are in the United States. The chronic infection of HCV, which effects about 80% of those infected, lasts lifelong and often leads to the development of cirrhosis and liver cancer.

The development of vaccines against HCV has been slowed by the extreme antigenic variability of the virus. Even when available, vaccines will not alleviate the problems faced by millions of chronic HCV carriers worldwide.

Most antibodies to HCV do not play a major role in clearance of infection, although neutralizing antibodies do exist. However, these tend to be strain-specific and are ineffective against emerging strains.

Presently, the only therapy with any demonstrated efficacy against HCV-induced liver disease involves the use of alpha-IFN, but this approach has achieved only limited success. Even the best clinical trials with alpha-IFN treatment report only 40-50% of chronic sufferers respond and 50% of these individuals relapse when treatment is stopped. There is also evidence that alpha-IFN treatment is much less effective against some HCV genotypes than others.

Currently, no conventional drugs against HCV infection (other than alpha-IFN) have yet been developed. Accordingly, improved immunotherapies for treating and preventing HCV infection are needed.

SUMMARY OF THE INVENTION

The present invention solves the foregoing problems by providing a recombinant fully human anti-HCV monoclonal antibody that specifically binds a broad variety of HCV isolates and inhibits the ability of the virus to infect cells.

In one embodiment, this is demonstrated by the antibodies ability to neutralize (i.e., inhibit or block) HCV in vitro (e.g., in a HCV pseudovirus neutralization assay). In another embodiment, this is demonstrated by the antibodies ability to inhibit HCV infectivity in vivo in a subject, such as an animal or a human.

Human monoclonal antibodies of the invention can be made efficiently, in virtually unlimited amounts, in highly purified form. Accordingly, the antibodies are suitable for prognosing, diagnosing, and/or treating an individual exposed or suspected of having been exposed to HCV. The antibodies can be produced using a variety of techniques for making human antibodies known in the art. For example, as exemplified herein, the antibodies can be generated in transgenic animals expressing human immunoglobulin gene segments, e.g., transgenic mice comprising a human Ig locus. Moreover, the antibodies can be administered alone or in combination, e.g., with an anti-HCV vaccine or other antibodies, to increase survival rates of subjects (e.g., animals and humans) infected with HCV.

Accordingly, the invention provides several advantages that include, but are not limited to, the following:

- a fully human recombinant anti-HCV antibody for prognosing, diagnosing, and/or treating HCV in a subject, e.g., protect from or inhibit HCV-mediated morbidity or mortality in a subject;
- a composition (e.g., pharmaceutical) and/or a kit comprising one or more fully human recombinant anti-HCV antibodies that can be used alone or in combination with commercially available vaccines to treat HCV infection and;
- an improved method of passive immunotherapy for treating a subject infected with HCV which can be used alone or in combination with active immunotherapy (HCV vaccine).

In one embodiment, the human monoclonal antibodies or antigen binding portions thereof of the invention specifically bind to a non-conformational epitope of the HCV E2 protein. Particular antibodies or antigen binding portions thereof specifically bind to an epitope within the HCV E2 protein. Such epitopes can reside, for example, within amino acids 1-50, 50-100, 100-150, 150-200, 200-250, 250-300, 300-350, 350-400, 400-450, 450-500, 500-550, 550-600, 600-650, 650-700, 700-746 of the HCV E2 protein, or any interval, portion or range thereof. In one embodiment, the antibodies or antigen binding portions thereof specifically bind to an epitope between about amino acid residues 412-464, 412-423, or 413-420. In another embodiment, the epitope of the HCV E2 protein comprises amino acid residues 412-423. In another embodiment, the epitope of the HCV E2 protein consists of amino acid residues 412-423. In one embodiment, the HCV E2 protein comprises amino acid residues 413, 418, and/or 420.

In other embodiments, the human monoclonal antibodies or antigen binding portions thereof can be characterized as specifically binding to an HCV E2 protein with a $K_D$ of less than about $10\times10^{-6}$ M. In a particular embodiment, the antibody or antigen binding portion thereof specifically binds to an HCV E2 protein (or fragment thereof) with a $K_D$ of at least about $10\times10^{-7}$ M, at least about $10\times10^{-8}$ M, at least about $10\times10^{-9}$ M, at least about $10\times10^{-10}$ M, at least about $10\times10^{-11}$ M, or at least about $10\times10^{-12}$ M or a $K_D$ even more favorable.

In various other embodiments, the antibodies or antigen binding portions thereof include a variable heavy chain region comprising an amino acid sequence at least 80%, 85%, 90%, 95%, 98%, 99% or more identical to a variable heavy chain region amino acid sequence of the antibody produced by clone 83-128 (SEQ ID NO: 1), 95-2 (SEQ ID NO: 3) or 073-1 (SEQ ID NO: 5).

In other embodiments, the antibodies or antigen binding portions thereof include a variable light chain region comprising an amino acid sequence at least 80%, 85%, 90%, 95%, 98%, 99% or more identical to a variable light chain region amino acid sequence of the antibody produced by clone 83-128 (SEQ ID NO: 2), 95-2 (SEQ ID NO: 4) or 073-1 (SEQ ID NO: 6).

In still other embodiments, the antibodies or antigen binding portions thereof include both a variable heavy chain region comprising an amino acid sequence at least 80%, 85%, 90%, 95%, 98%, 99% or more identical to a variable heavy chain region amino acid sequence of the antibody produced by clone 83-128 (SEQ ID NO: 1), 95-2 (SEQ ID NO: 3) or 073-1 (SEQ ID NO: 5) and a variable light chain region comprising an amino acid sequence at least 80%, 85%, 90%, 95%, 98%, 99%, or more identical to a variable light chain amino acid sequence of clone 83-128 (SEQ ID NO: 2), 95-2 (SEQ ID NO: 4) or 073-1 (SEQ ID NO: 5).

In certain other embodiments, the antibodies or antigen binding portions thereof specifically bind to an epitope that overlaps with an epitope bound by an antibody produced by clone 83-128, 95-2 or 073-1 and/or competes for binding to a HCV, or portion thereof with an antibody produced by clone 83-128, 95-2 or 073-1.

The variable heavy and light chain regions of the antibodies or antigen binding portions thereof typically include one or more complementarity determining regions (CDRs). These include the CDR1, CDR2, and CDR3 regions. In particular embodiments, the variable heavy chain CDRs are at least 80%, 85%, 90%, 95%, or 99%, or more identical to a CDR of the antibody produced by clone 83-128 (SEQ ID NOs: 7-9), 95-2 (SEQ ID NOs: 10-12) or 073-1 (SEQ ID NO: 13-15). In other particular embodiments, variable light chain CDRs are at least 80%, 85%, 90%, 95%, or 99%, or more identical to a CDR of a variable light chain region of the antibody produced by clone 83-128 (SEQ ID NOs: 16-18), 95-2 (SEQ ID NOs: 19-21) or 073-1 (SEQ ID NO: 22-24).

Accordingly, particular antibodies or fragments of the invention comprise a variable heavy chain region that includes one or more complementarity determining regions (CDRs) that are at least 80%, 85%, 90%, 95%, or 99%, or more identical to a CDR of a variable heavy chain region of the antibody produced by clone 83-128 (SEQ ID NOs: 7-9), 95-2 (SEQ ID NOs: 10-12) or 073-1 (SEQ ID NO: 13-15) and a variable light chain region that includes one or more CDRs that are at least 80%, 85%, 90%, 95%, 99%, or more identical to a CDR of a variable light chain region of the antibody produced by clone 83-128 (SEQ ID NOs: 16-18), 95-2 (SEQ ID NOs: 19-21) or 073-1 (SEQ ID NO: 22-24).

The variable heavy chain region of the antibodies or antigen binding portions thereof can also include all three CDRs that are at least 80%, 85%, 90%, 95%, or 99%, or more identical to the CDRs of the variable heavy chain region of the antibody produced by clone 83-128 (SEQ ID NOs: 7-9), 95-2 (SEQ ID NOs: 10-12) or 073-1 (SEQ ID NO: 13-15) and/or all three CDRs that are at least 80%, 85%, 90%, 95%, 99%, or more identical to the CDRs of the variable light chain region of the antibody produced by clone 83-128 (SEQ ID NOs: 16-18), 95-2 (SEQ ID NOs: 19-21) or 073-1 (SEQ ID NO: 22-24).

In another embodiment, the variable heavy chain region of the antibodies or antigen binding portions thereof can also include one or more heavy chain consensus sequence CDRs as set forth in SEQ ID NOs: 87-89 and/or one or more light chain consensus CDRs asset forth in SEQ ID NOs: 90-92.

In another embodiment of the invention, the human antibodies or antigen binding portions thereof (a) include a heavy chain variable region that is encoded by or derived from (i.e., is the product of) a human VH 3-33 gene; and/or (b) include a light chain variable region that is encoded by or derived from a human Vκ L6 gene.

Human monoclonal antibodies of the present invention include full-length antibodies, for example, that include an effector domain, (e.g., an Fc domain), as well as antibody portions or fragments, such as single-chain antibodies and Fab fragments. The antibodies can also be linked to a variety of therapeutic agents (e.g., antiviral agents or toxins) and/or a label.

In another aspect, the invention features isolated polypeptides that include an antigen binding portion of an antibody produced by hybridoma clone of 83-128, 073-1, 95-2, 95-14, 95-15, 95-18, 95-20, 95-21, 95-25, 95-26, 95-30, 95-38, 95-39, 95-42, 95-43, 95-48, 95-49, 95-52, 95-54, 95-58, 95-62, and combinations thereof.

In another aspect, the invention features isolated nucleic acids including a sequence encoding a antibody heavy chain variable region which is at least 75%, 80%, 85%, 90%, 95%, 99%, or more identical to SEQ ID NO: 25, 27 or 29. The invention also features isolated nucleic acids that include a sequence encoding an antibody light chain variable region which is at least 75%, 80%, 85%, 90%, 95%, 99%, or more identical to SEQ ID NO: 26, 28 or 30. The invention also features expression vectors including any of the foregoing nucleic acids either alone or in combination (e.g., expressed from one or more vectors), as well as host cells comprising such expression vectors.

Suitable host cells for expressing antibodies of the invention include a variety of eukaryotic cells, e.g., yeast cells, mammalian cells, e.g., Chinese hamster ovary (CHO) cells, NS0 cells, myeloma cells, or plant cells.

In another aspect, the invention features compositions and kits that include one or more isolated human monoclonal antibodies or antigen binding portions thereof as described herein that specifically bind to HCV and inhibit the ability of the virus to infect mammalian cells. The composition or kit can further include one or more antibodies (e.g., human monoclonal or polyclonal antibodies) or antigen-binding portions thereof that specifically bind to HCV. In one embodiment, the polyclonal antibody or antigen binding portion thereof specifically binds to HCV E2 protein. In a particular embodiment, the composition or kit includes both (a) an isolated human monoclonal antibody that specifically binds to a first HCV isolate; and (b) an isolated human monoclonal antibody that specifically binds to a second HCV isolate.

The invention also features methods of treating HCV disease in a subject by administering to the subject an isolated human monoclonal antibody or antigen binding portion thereof as described herein (i.e., that specifically binds to HCV) in an amount effective to inhibit HCV disease, e.g., HCV-mediated symptoms or morbidity.

Human monoclonal antibodies or portions thereof (and compositions comprising the antibodies or portions thereof) of the invention can be administered in a variety of suitable fashions, e.g., intravenously (IV), subcutaneously (SC), or, intramuscularly (IM) to the subject. The antibody or antigen-binding portion thereof can be administered alone or in combination with another therapeutic agent, e.g., a second human monoclonal antibody or antigen binding portion thereof. In one example, the second human monoclonal antibody or antigen binding portion thereof specifically binds to a second HCV isolate that differs from the isolate bound to the first antibody. In another example, the antibody is administered together with another agent, for example, an antiviral agent. In another example, the antibody is administered together with a polyclonal gamma-globulin (e.g., human gamma-globulin). In another example, the antibody is administered before, after, or contemporaneously with a HCV vaccine.

In another aspect, the invention features methods for making an antibody or antigen binding portion thereof that specifically binds to a HCV. In one embodiment, the method involves immunizing a transgenic non-human animal having a genome comprising a human heavy chain transgene and a human light chain transgene with a composition that includes a HCV, e.g., live or inactivated virus and isolating an antibody, antibody producing cell, or antibody encoding nucleic acid from the animal. The HCV can be inactivated, for example, by chemical treatment and/or lyophilization. The method can further include evaluating binding of the antibody to the HCV or HCV E2 protein.

The invention also features methods for making the antibodies or antigen binding portions thereof by expressing nucleic acids encoding human antibodies in a host cell (e.g., nucleic acids encoding the antigen binding region portion of an antibody). In yet another aspect, the invention features a hybridoma or transfectoma including the aforementioned nucleic acids.

The invention also features a method for making a hybridoma that expresses an antibody that specifically binds to a HCV by immunizing a transgenic non-human animal having a genome that includes a human heavy chain transgene and a human light chain transgene, with a composition that includes the HCV or HCV E2 protein; isolating splenocytes from the animal; generating hybridomas from the splenocytes; and selecting a hybridoma that produces an antibody that specifically binds to HCV or HCV E2 protein thereof.

In another embodiment, the invention provides an antigen comprising a non-conformational epitope of the HCV E2 protein, amino acids 412-464, 412-423, or 413-420. The antigen can be used for raising, screening, or detecting the presence of an anti-HCV E2 antibody or can be used as an agent in active immunotherapy, i.e. as a vaccine. As a vaccine, the antigen can be used alone or in combination with an appropriate adjuvant or hapten, e.g., mixed or conjugated either chemically or genetically. Conjugates include but are not limited to toxoids, virus-like particles (VLPs), and protein carriers all of which are designed to enhance the immune response to the vaccine antigen. The antigen when used for active immunotherapy can be also used in combination with passive immunotherapy, for example, with any of the anti-HCV E2 antibodies disclosed herein.

Treatment of humans with human monoclonal antibodies offers several advantages. For example, the antibodies are likely to be less immunogenic in humans than non-human antibodies. The therapy is also rapid because HCV inactivation can occur as soon as the antibody reaches sites of infection and directly neutralizes the disease-causing HCV. Human antibodies also localize to appropriate sites in humans more efficiently than non-human antibodies. Furthermore, the treatment is specific for HCV, and is recombinant and highly purified and, unlike traditional therapies, avoids the potential of being contaminated with adventitious agents.

Other features and advantages of the invention will be apparent from the following detailed description, and from the claims.

BRIEF DESCRIPTION OF THE DRAWINGS

FIGS. 2A and 2B are graphs showing neutralization of infection of Hep3b cells with various HCV genotype pseudovirus in the presence of human antibodies 95-2, 83-128, and 17C7 (irrelevant human mAb). Five-fold dilutions of antibody were incubated with each HCV pseudovirus for one hour at room temperature. The virus-antibody mixture was added to Hep3b cells followed by incubation at 37° C. for 72 hours. Infection was quantitated with Brightglo luciferase assay and read in a Victor3 plate reader for light output. Human antibody against rabies (17C7) was used as a negative control.

FIGS. 3A and 3B are Western blots showing antibody binding to purified soluble mammalian expressed E2 protein (E2-661) from HCV genotype 1a and 1b subjected to reducing (FIG. 3A) or non-reducing (FIG. 3B) SDS-PAGE followed by transfer to PVDF membrane. Westerns blots were performed with anti-his tag monoclonal (his), 83-128 and 95-2 using anti-mouse IgG (his) or anti-human IgG (95-2 and 83-128) conjugated to HRP with enhanced chemiluminescent detection reagent. The genotype of the soluble E2 is indicated above the blots. The primary antibody used for detection is listed below the blots. The molecular weight markers in kilodaltons is listed to the left of each set of blots.

FIG. 4 is a table showing the affinity of human antibodies 95-2 and 83-128 to HCV E2 412-423 epitope expressed as a bacterial fusion protein. Goat anti-human IgG Fc was amide coupled to the Biacore chip. Human antibodies 95-2 and 83-128 were separately captured on the chip and E2-G bacterially expressed protein containing E2 412-423 amino acids was flowed over at varying concentrations. The BIAevaluation™ software was used to fit the curves and calculate the affinity constants.

FIG. 5 is a map of the HCV polyprotein showing the location of E1 and E2 mammalian expressed proteins. The E1 and E2 polyprotein is indicated at top by a long white box with amino acid numbers noted above. The transmembrane domains (TM) are indicated by light grey boxes and the hypervariable domain 1 (HVR1) of E2 is indicated by a dark grey box. The mammalian proteins expressed from engineered constructs are listed below as dark grey bars. Sites of signal peptidase cleavage are indicated by arrows. The name of each protein is followed by the encoded amino acids in parenthesis and total amino acids in the expressed protein.

FIGS. 6A and 6B are graphs showing the results of lectin capture ELISA of mammalian expressed C-terminal truncations of E2. Cell culture supernatants containing mammalian expressed C-terminal truncations of E2 fusion proteins containing E2 amino acids (indicated in FIG. 7) were coated on an ELISA plate and probed with two-fold dilutions of human antibodies 95-2 (FIG. 6A) and 83-128 (FIG. 6B) and mouse six histidine tag antibody (his tag). Bound antibodies were detected with goat-anti-human (95-2 and 83-128) or goat-anti-mouse (his tag) conjugated to alkaline phosphatase and PNPP substrate.

FIG. 7 is a map showing bacterially expressed proteins spanning the amino-terminal 80 amino acids of E2. The first 80 amino acids of the E2 protein are represented at top by a white box with the amino acids numbers above. The 27 amino acid hypervariable region 1 (HVR1) at the amino-terminus is indicated by a dark grey box. The proteins expressed from engineered constructs are indicated by light grey bars with names to the left of the bar and amino acid numbers for the start and end of the protein listed below the bar.

FIGS. 8A, 8B, and 8C are graphs showing binding of human antibodies 95-2 (FIG. 8A) and 83-128 (FIG. 8B) and mouse six histidine tag antibody (his tag) (FIG. 8C) to bacterially expressed pieces of E2 first 80 amino acids. Bacterially expressed fusion proteins containing E2 amino acids (indicated in FIG. 7) were coated on an ELISA plate and probed with two-fold dilutions of antibody. Bound antibodies were detected with goat-anti-human (95-2 and 83-128) or goat-anti-mouse (his tag) conjugated to alkaline phosphatase and PNPP substrate.

FIGS. 9A, 9B, and 9C are graphs showing binding of human antibodies 95-2 (FIG. 9A) and 83-128 (FIG. 9B) and mouse six histidine tag antibody (his tag) (FIG. 9C) to bacterially expressed fusion proteins containing E2 amino acids 412-423 with mutations. Bacterially expressed fusion proteins containing E2 amino acids 412-423 with the indicated amino acids mutated to an alanine or containing no mutations (WT) were coated on an ELISA plate and probed with two-fold dilutions of antibody. Bound antibodies were detected with goat-anti-human (95-2 and 83-128) or goat-anti-mouse (his tag) conjugated to alkaline phosphatase and PNPP substrate.

FIG. 10 is a table showing E2 amino acids 412-423 alignments from the Los Alamos HCV Sequence Database supported by NIH. The one letter amino acid code for the prototype genotype 1a sequence for amino acids 412-423 is listed at the top left of the chart (1a). Any amino acids that are identical to the 1a sequence are indicated with a dash and the amino acid listed for any position that is different from the prototype genotype 1a sequence. The number of times that this twelve amino acid sequence is found in the condensed database is listed under count and the percent of the total is listed under percent. The sequences of genotypes 1a and 1b soluble E2 proteins of the present invention are listed in the top two lines.

FIGS. 12A, 12B, and 12C are graphs showing binding of human antibodies 95-2 (FIG. 12A) and 83-128 (FIG. 12B) and mouse six histidine tag antibody (his tag) (FIG. 12C) to E2 amino acids 412-423 from other genotypes. Bacterially expressed fusion proteins containing E2 amino acids 412-423 with the sequence from the indicated genotype were coated on an ELISA plate and probed with two-fold dilutions of antibody. Bound antibodies were detected with goat-anti-human (95-2 and 83-128) or goat-anti-mouse (his tag) conjugated to alkaline phosphatase and PNPP substrate.

FIG. 13 depicts the E1/E2 codon optimized 1a H77 sequence (SEQ ID NO:27) including added ends containing restrictions (represented as bold lowercase), additional overhangs to optimize restriction enzyme cutting (represented as underlined lowerase), consensus Kozak sequence (represented as bold underlined lowercase) and MG initiation codon (represented as bold underlined uppercase).

FIG. 14 depicts the alignment of the heavy chain variable region of antibodies derived from clones 83-128 (SEQ ID NO:1), 95-2 (SEQ ID NO:3), 95-14 (SEQ ID NO:32), 95-38 (SEQ ID NO:33), 95-25 (SEQ ID NO:34), 95-42 (SEQ ID NO:35), 95-43 (SEQ ID NO:36), 95-49 (SEQ ID NO:37), 95-54 (SEQ ID NO:38), 95-58 (SEQ ID NO:39) and 95-62 (SEQ ID NO:40) and which are reactive against epitope 412-423 of E2-660 HCV glycoprotein.

FIG. 15 depicts the alignment of light chain variable region of antibodies derived from clones 83-128 (SEQ ID NO:2), 073-1 (SEQ ID NO:6), 95-2 (SEQ ID NO:4), 95-14 (SEQ ID NO:44) and 95-38 (SEQ ID NO:53).

DETAILED DESCRIPTION OF THE INVENTION

Figure 1:
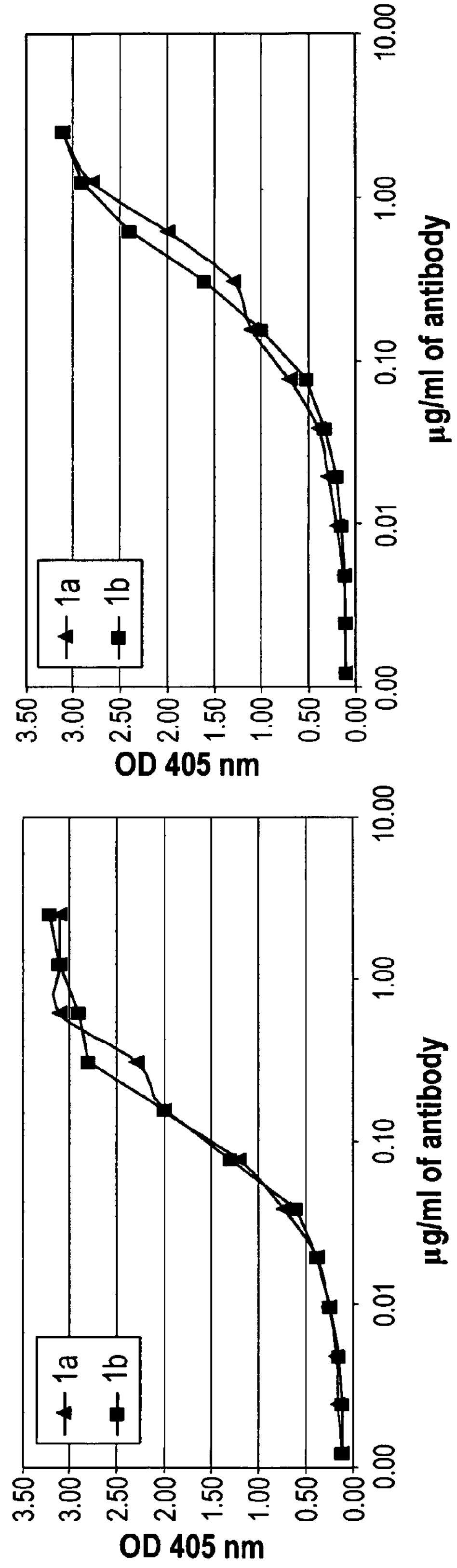
FIGS. 1A and 1B are graphs showing binding of human antibody 95-2 (FIG. 1A) and human antibody 83-128 (FIG. 1B) to soluble HCV genotype 1a E2-660 (triangles) and soluble HCV genotype 1b E2-661 (squares). ELISA plates were coated with 2 μg/ml of antigen and probed with antibody in two-fold dilutions. Bound antibody was detected with goat-anti-human secondary antibody conjugated to alkaline phosphatase and PNPP substrate.

In order that the present invention may be more readily understood, certain terms are first defined. Additional definitions are set forth throughout the detailed description.

Definitions

The terms "hepatitis C virus," "HCV," "non-A non-B hepatitis," or "NANBH" are used interchangeably herein, and include any "genotype" or "subgenotype" (also termed "subtype") of the virion, or portion thereof (e.g., a portion of the E2 protein of genotype 1a of HCV), that is encoded by the RNA of hepatitis C virus or that occurs by natural allelic variation.

HCV is organized by a 5'-untranslated region that is followed by an open reading frame (ORF) that codes for about 3,010 amino acids. The ORF runs from nucleotide base pair 342 to 8,955 followed by another untranslated region at the 3' end. The amino acids are subdivided into ten proteins in the order from 5' to 3' as follows: C; E1; E2; NS1; NS2; NS3; NS4 (a and b); and NS5 (a and b). These proteins are formed from the cleavage of the larger polyprotein by both host and viral proteases. The C, E1, and E2 proteins are structural and the NS1-NS5 proteins are nonstructural proteins. The C region codes for the core nucleocapsid protein. E1 and E2 are glycosylated envelope proteins that coat the virus. NS2 may be a zinc metalloproteinase. NS3 is a helicase. NS4a functions as a serine protease cofactor involved in cleavage between NS4b and NS5a. NS5a is a serine phosphoprotein whose function is unknown. The NS5b region has both RNA-dependent RNA polymerase and terminal transferase activity.

There are about six (6) distinct genotypes (e.g., genotypes 1, 2, 3, 4, 5, and 6) that are categorized by variations in the core protein and over 80 subgenotypes which exhibit further variation within each genotype, some of which include: 1a; 1b; 1c; 2a; 2b; 2c; 3a; 3b; 4a; 4b; 4c; 4d; 4e; 5a; and 6a.

The term "antibody" as referred to herein includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., HCV). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a $F(ab')_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al, (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody which displays a single binding specificity and affinity for a particular epitope. Accordingly, the term "human monoclonal antibody" refers to an antibody which displays a single binding specificity and which has variable and constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$, regions of the recombinant antibodies are sequences that, while derived from and related to human germline $V_H$ and $V_L$, sequences, may not naturally exist within the human antibody germline repertoire in vivo.

The term "human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) *Nature* 368(6474): 856-859); Lonberg, N. (1994) *Handbook of Experimental Pharmacology* 113:49-101; Lonberg, N. and Huszar, D. (1995) *Intern. Rev. Immunol. Vol.* 13: 65-93, and Harding, F. and Lonberg, N. (1995) *Ann. N.Y. Acad. Sci* 764:536-546). However, the term "human antibody" does not include antibodies in which CDR sequences derived from the germline of another mammalian species, such as a mouse, have been grafted onto human framework sequences (i.e., humanized antibodies).

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

An "isolated antibody," as used herein, is intended to refer to an antibody which is substantially free of other antibodies having different antigenic specificities (e.g., an isolated antibody that specifically binds to HCV is substantially free of antibodies that specifically bind antigens other than HCV). In addition, an isolated antibody is typically substantially free of other cellular material and/or chemicals. In one embodiment of the invention, a combination of "isolated" monoclonal antibodies having different HCV specificities are combined in a well defined composition.

The term "epitope" or "antigenic determinant" refers to a site on an antigen to which an immunoglobulin or antibody specifically binds (e.g., E1 or E2 of HCV, for example, amino acids 412-464 of E2). Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance. See, e.g., *Epitope Mapping Protocols in Methods in Molecular Biology*, Vol. 66, G. E. Morris, Ed. (1996). In a preferred embodiment, the epitope (or antigenic determinant) performs as a linear epitope in that, even when in the context of a larger amino acid segment, e.g., protein having 3-dimensional structure, no additional increase in affinity for the epitope/antigenic determinant is observed.

As used herein, the terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument using recombinant HCV as the analyte and the antibody as the ligand, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

Also encompassed by the present invention are antibodies that bind the same epitopes as the human antibodies described herein, i.e., antibodies that compete for binding to HCV. Antibodies that recognize the same epitope can be identified using routine techniques such as an immunoassay, for example, by showing the ability of one antibody to block the binding of another antibody to a target antigen, i.e., a competitive binding assay. Competitive binding is determined in an assay in which the immunoglobulin under test inhibits specific binding of a reference antibody to a common antigen, such as HCV. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

The term "$K_D$," as used herein, is intended to refer to the dissociation equilibrium constant of a particular antibody-antigen interaction. Typically, the human antibodies of the invention bind to HCV with a dissociation equilibrium constant ($K_D$) of less than approximately $10^{-7}$ M, such as less than approximately $10^{-8}$ M, $10^{-9}$ M or $10^{-10}$ M or even lower when determined by surface plasmon resonance (SPR) technology in a BIACORE 3000 instrument using recombinant human HCV as the analyte and the antibody as the ligand.

The term "$K_{off}$," as used herein, is intended to refer to the off rate constant for the dissociation of an antibody from the antibody/antigen complex.

The term "EC50," as used herein, refers to the concentration of an antibody or an antigen-binding portion thereof, which induces a response, either in an in vitro or an in vivo assay, which is 50% of the maximal response, i.e., halfway between the maximal response and the baseline.

As used herein, "isotype" refers to the antibody class (e.g., IgM or IgG1) that is encoded by heavy chain constant region genes. In one embodiment, a human monoclonal antibody of the invention is of the IgG1 isotype. In another embodiment, a human monoclonal antibody of the invention is of the IgG2 isotype.

As used herein, the terms "neutralizes HCV," "inhibits HCV," and "blocks HCV" are used interchangeably to refer to the ability of an antibody of the invention to prevent HCV from infecting a given cell.

As used herein, the term "non-conformational epitope" refers to a linear epitope which is typically comprised of a continuous amino acid sequence which is sufficient for binding with an antibody capable of binding to such an epitope. This is in contrast to a conformational epitope, which requires discontinuous amino acid sequences to form a 3-dimensional structure in order for binding between the epitope and the antibody to occur. A linear epitope can also be distinguished from a conformational epitope in that under denaturing conditions, (e.g., in an immunoblot assay as described herein), the epitope can still be bound by an antibody that recognizes such an epitope. In one embodiment, the invention provides an HCV E2 epitope that is linear, for example, non conformational, for example, comprising residues 412 to 423, or, consisting of residues 412-423. In a related embodiment, the antibodies of the invention specifically bind to such a linear epitope and not a conformational epitope. Still further, the invention provides such a linear epitope as suitable for the use in vaccine development, the raising of antibodies thereto, and/or for the use in active immunotherapy alone or in combination with passive immunotherapy.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the $C_H$ gene encoding the nonswitched isotype is typically the first $C_H$ gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ ($\delta$-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a $\mu$ switch region, will be 5' (i.e., upstream) of the construct region to be deleted during the switch recombination. The "switch acceptor" region will be between the construct region to be deleted and the replacement constant region (e.g., $\gamma$, $\epsilon$, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the $C_H$ genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$, domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., $V_H$, $V_L$, CDR3) that bind to HCV, is intended to refer to a nucleic acid molecule in which the nucleotide sequences encoding the antibody or antibody portion are free of other nucleotide sequences encoding antibodies that bind antigens other than HCV, which other sequences may naturally flank the nucleic acid in human genomic DNA.

The present invention also encompasses "conservative sequence modifications" of the sequences set forth in the SEQ ID NOs of the present invention, i.e., nucleotide and amino acid sequence modifications which do not abrogate the binding of the antibody encoded by the nucleotide sequence or containing the amino acid sequence, to the antigen. Such conservative sequence modifications include nucleotide and amino acid substitutions, additions and deletions. For example, modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-HCV antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997))

Alternatively, in another embodiment, mutations can be introduced randomly along all or part of an anti-HCV antibody coding sequence, such as by saturation mutagenesis, and the resulting modified anti-HCV antibodies can be screened for binding activity.

A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence.

As depicted in FIG. 14, in one embodiment, a consensus sequence for the heavy chain variable region CDRs is derived by optimal alignment of the amino acid sequences of the heavy chain variable region of the antibodies which are reactive against epitope 412-423 of the E2-660 HCV glycoprotein. For example, the antibodies derived from clones 83-128 (SEQ ID NO:1), 95-2 (SEQ ID NO:3), 95-14 (SEQ ID NO:32), 95-38 (SEQ ID NO:33), 95-25 (SEQ ID NO:34), 95-42 (SEQ ID NO:35), 95-43 (SEQ ID NO:36), 95-49 (SEQ ID NO:37), 95-54 (SEQ ID NO:38), 95-58 (SEQ ID NO:39) and 95-62 (SEQ ID NO:40) are optimally aligned to obtain the consensus sequences for CDR1, CDR2 and CDR3. Accordingly, the consensus sequence for CDR1 of the heavy chain variable region is found to be "1YGMH," set forth in SEQ ID NO:87, where "1" represents a small and polar amino acid residue. The consensus sequence for CDR2 of the heavy chain variable region is found to be "VIWXDX7NXYYADS1516G," shown in SEQ ID NO:88, where "X" can be any amino acid residue, "7" represents a small and polar amino acid residue, "15" represents a hydrophobic amino acid residue and "16" represents a polar and positively charged amino acid residue. The consensus sequence for CDR3 of the heavy chain variable region is found to be "ARDI567XR10X121YFD17", shown in SEQ ID NO:89, where "X" represents any amino acid residue, "5" represents phenylalanine or no amino acid, "6" represents Serine or Threonine, "7" and "12" represent a hydrophobic amino acid residue, "10" represents a small amino acid residue and "17" represents an aromatic amino acid residue.

Similarly, the consensus sequence for the CDRs of light chain variable region can be derived by optimal alignment of the amino acid sequences of antibodies reactive against epitope 412-423 of E2-660 HCV glycoprotein, as shown in FIG. 15. For example, amino acid sequences of the light chain variable regions of antibodies derived from clones 83-128 (SEQ ID NO:2), 073-1 (SEQ ID NO:6), 95-2 (SEQ ID NO:4), 95-14 (SEQ ID NO:44) and 95-38 (SEQ ID NO:53) are optimally aligned to obtain the consensus sequences for CDR1, CDR2 and CDR3 of the light chain variable region. The consensus sequence for CDR1 of the light chain variable region is found to be "RASQSVXSYLA," set forth in SEQ ID NO:90, where "X" can be any amino acid residue. The consensus sequence for CDR2 of the light chain variable region is found to be "DASNRAT," set forth in SEQ ID NO:91. The consensus sequence for CDR3 of the light chain variable region is found to be "QQRSNW7T," shown in SEQ ID NO:92, where "7" represents a small and hydrophobic amino acid residue.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48): 444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and)(BLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "treat," "treating," and "treatment," as used herein, refer to therapeutic or preventative measures described herein. The methods of "treatment" employ administration to a subject, in need of such treatment, a human antibody of the present invention, for example, a subject having an HCV-mediated disorder or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "HCV-mediated disorder," as used herein, includes disease states and/or symptoms associated with HCV infection. In general, the term "HCV-mediated disorder" refers to any disorder, the onset, progression or the persistence of the symptoms of which requires the participation of HCV. Exemplary HCV-mediated disorders include, but are not limited to, for example, cirrhosis and liver cancer.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "patient" includes human and other mammalian subjects that receive either prophylactic or therapeutic treatment.

As used herein, the term "subject" includes any human or non-human animal. For example, the methods and compositions of the present invention can be used to treat a subject with an inflammatory disease, such as arthritis, e.g., rheumatoid arthritis. The term "non-human animal" includes all vertebrates, e.g., mammals and non-mammals, such as non-human primates, sheep, dog, cow, chickens, amphibians, reptiles, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Various aspects of the invention are described in further detail in the following subsections.

Overview

HCV causes fatal hepatocyte pathologies in humans. Provided herein are methods and compositions for treatment and prevention of HCV infected animals, in particular, human subjects, more particularly. The compositions include antibodies that recognize the HCV E2 protein, or portion thereof. In particular, recombinant fully human monoclonal antibodies are provided. In certain embodiments, these human monoclonal antibodies are produced in mice expressing human immunoglobulin gene segments (described below). Combinations of anti-HCV antibodies are also provided.

The new methods include administering antibodies (and antigen-binding portions thereof) that bind to HCV in a subject to inhibit HCV-mediated disease in the subject. For example, human monoclonal anti-HCV antibodies described herein can neutralize HCV and inhibit HCV infection and sequelae thereof, for example, cirrhosis of the liver and/or liver cancer. In other examples, combinations of anti-HCV antibodies (e.g., anti-HCV E2 protein monoclonal antibodies) can be administered to inhibit HCV-mediated disease. The human monoclonal antibodies can be administered alone or in combination with other therapies.

I. Production of Human Antibodies to HCV

The present invention encompasses fully human antibodies that bind HCV, e.g., human HCV. Exemplary human monoclonal antibodies that bind HCV include 83-128, 95-2, 95-14, 95-38, and 073-1.

Human monoclonal antibodies of the invention can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

The preferred animal system for generating hybridomas which produce human monoclonal antibodies of the invention is the murine system. Hybridoma production in the mouse is well known in the art, including immunization protocols and techniques for isolating and fusing immunized splenocytes.

In one embodiment, human monoclonal antibodies directed against HCV are generated using transgenic mice carrying parts of the human immune system rather than the mouse system. In one embodiment, the invention employs transgenic mice, referred to herein as "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol. Vol.* 13: 65-93, and Harding, F. and Lonberg, N. (1995) *Ann. N.Y. Acad. Sci* 764:536-546). The preparation of HuMAb mice is described in detail in Section II below and in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Lonberg et al., (1994) *Nature* 368(6474): 856-859; Lonberg, N. (1994) *Handbook of Experimental Pharmacology* 113:49-101; Taylor, L. et al. (1994) *International Immunology* 6: 579-591; Lonberg, N. and Huszar, D. (1995) *Intern. Rev. Immunol.* Vol. 13: 65-93; Harding, F. and Lonberg, N. (1995) *Ann. N.Y. Acad Sci* 764: 536-546; Fishwild, D. et al. (1996) *Nature Biotechnology* 14: 845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992.

Immunizations

To generate fully human monoclonal antibodies to HCV, transgenic mice containing human immunoglobulin genes (e.g., HCo12, HCo7) can be immunized with a purified or enriched preparation of the HCV antigen and/or cells expressing HCV, as described, for example, by Lonberg et al. (1994) *Nature* 368(6474): 856-859; Fishwild et al. (1996) *Nature Biotechnology* 14: 845-851 and WO 98/24884. As described herein, HuMAb mice are immunized either with recombinant HCV proteins or cell lines expressing HCV as immunogens. Alternatively, mice can be immunized with DNA encoding HCV. Preferably, the mice will be 6-16 weeks of age upon the first infusion. For example, a purified or enriched preparation (10-100 μg) of the recombinant HCV antigen can be used to immunize the HuMAb mice intraperitoneally. In the event that immunizations using a purified or enriched preparation of the HCV antigen do not result in antibodies, mice can also be immunized with cells expressing HCV proteins, e.g., a cell line, to promote immune responses. Exemplary cell lines include HCV-overexpressing stable CHO and Raji cell lines.

Cumulative experience with various antigens has shown that the HuMAb transgenic mice respond best when initially immunized intraperitoneally (IP) or subcutaneously (SC) with antigen in complete Freund's adjuvant, followed by every other week IP/SC immunizations (up to a total of 10) with antigen in incomplete Freund's adjuvant. The immune response can be monitored over the course of the immunization protocol with plasma samples being obtained by retro-orbital bleeds. The plasma can be screened by ELISA (as described below), and mice with sufficient titers of anti-HCV human immunoglobulin can be used for fusions. Mice can be boosted intravenously with antigen 3 days before sacrifice and removal of the spleen.

Antigen Based Vaccines and Conjugates Thereof

The present invention also provides a conserved non-conformational epitope of the HCV E2 envelope glycoprotein, for example, amino acids 412-464, 412-423, or 413-420 of the HCV E2 protein, for use in active immunization against HCV infection. This epitope can be used alone or be modified, e.g., to enhance an immune response to the epitope.

Chemically constructed antigen conjugates can be made using a variety of well known and readily available cross-linking reagents. These cross-linking reagents can be homofunctional or heterofunctional compounds, such as, e.g., SPDP, SATA, SMCC, DTNB, that form covalent linkages with different reactive amino acid or carbohydrate side chains on the selected antigen.

The carrier can be selected from the group consisting of OMPC (Outer Membrane Protein Complex of *Neisseria nieningitidis*), BSA (bovine serum albumin), OVA (ovalbumin), THY (bovine thyroglobulin), KLH (keyhole limpet hemocyanin), and TT (tetanus toxoid protein). Other carriers, that have the capability to self assemble into virus-like particles (VLP's), include HbSAg (surface antigen protein) and HBcAg (core antigen protein) of Hepatitis B virus, rotavirus capsid proteins, the L1 protein of the human papilloma virus, hepatitis E virus particles, polyoma virus protein and bovine papilloma virus structural proteins. (see J. of Phar. Sciences 95:70-79 (2005)).

The conjugating can be achieved genetically or chemically, for example, using one or more of maleimide/thiol coupling, bromoacetamide/thiol coupling, and histidine-selective cross-linking. The conjugating can be achieved using a cross-linker selected from the group consisting of one of more of sulfosuccinimidyl 4-(N-maleimidomethyl)cyclohexane-1-carboxylate (sSMCC), N-maleimidobenzoyl-N-hydroxysuccinimide ester (MBS), glutaraldehyde, 1-ethyl-3-(3-dimethylaminopropyl)carbodiimide (EDCI), Bis-diazobenzidine (BDB), N-acetyl homocysteine thiolactone (NAHT), and N-[.epsilon.-maleimidocaproyloxy]sulfosuccinimde ester (sEMCS). In one embodiment, the cross-linker is a N-[.epsilon.-maleimidocaproyloxy]sulfosuccinimde ester (sEMCS).

Generation of Hybridomas Producing Human Monoclonal Antibodies to HCV

To generate hybridomas producing human monoclonal antibodies to HCV, splenocytes and lymph node cells from immunized mice can be isolated and fused to an appropriate immortalized cell line, such as a mouse myeloma cell line. The resulting hybridomas can then be screened for the production of antigen-specific antibodies. For example, single cell suspensions of splenic lymphocytes from immunized mice can be fused to SP2/0-Ag8.653 nonsecreting mouse myeloma cells (ATCC, CRL 1580) with 50% PEG (w/v). Cells can be plated at approximately $1\times10^5$ in flat bottom microtiter plate, followed by a two week incubation in selective medium containing besides usual reagents 10% fetal Clone Serum, and 1×HAT (Sigma). After approximately two weeks, cells can be cultured in medium in which the HAT is replaced with HT. Individual wells can then be screened by ELISA for human anti-HCV monoclonal IgM and IgG antibodies, or for binding to the surface of cells expressing HCV proteins, e.g., a CHO cell line expressing HCV, by FLISA (fluorescence-linked immunosorbent assay). Once extensive hybridoma growth occurs, medium can be observed usually after 10-14 days. The antibody secreting hybridomas can be replated, screened again, and if still positive for human IgG, anti-HCV monoclonal antibodies can be subcloned at least twice by limiting dilution. The stable subclones can then be cultured in vitro to generate antibody in tissue culture medium for characterization.

Generation of Transfectomas Producing Human Monoclonal Antibodies to HCV

Human antibodies of the invention also can be produced in a host cell transfectoma using, for example, a combination of recombinant DNA techniques and gene transfection methods as is well known in the art (Morrison, S. (1985) Science 229:1202).

For example, in one embodiment, the gene(s) of interest, e.g., human antibody genes, can be ligated into an expression vector such as a eukaryotic expression plasmid such as used by GS gene expression system disclosed in WO 87/04462, WO 89/01036 and EP 338 841 or other expression systems well known in the art. The purified plasmid with the cloned antibody genes can be introduced in eukaryotic host cells such as CHO-cells or NSO-cells or alternatively other eukaryotic cells like a plant derived cells, fungi or yeast cells. The method used to introduce these genes can be methods described in the art such as electroporation, lipofectine, lipofectamine or other. After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively these cloned antibody genes can be expressed in other expression systems such as *E. coli* or in complete organisms or can be synthetically expressed.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al, 1998, *Nature* 332:323-327; Jones, P. et al., 1986, *Nature* 321:522-525; and Queen, C. et al., 1989, *Proc. Natl. Acad. See*. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and, HindIII sites are engineered upstream of the translation initiation sites.

For both the heavy and light chain variable regions, the optimized coding, and corresponding non-coding, strand sequences are broken down into 30-50 nucleotide oligonucleotides starting at approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors can be constructed so that PCR amplified V heavy and V kappa light chain cDNA sequences can be used to reconstruct complete heavy and light chain minigenes. These plasmids can be used to express completely human $IgG_1\kappa$ or $IgG_4\kappa$ antibodies. Fully human and chimeric antibodies of the present invention also include IgG2, IgG3, IgE, IgA, IgM, and IgD antibodies. Similar plasmids can be constructed for expression of other heavy chain isotypes, or for expression of antibodies comprising lambda light chains.

Thus, in another aspect of the invention, one or more structural features of a human anti-HCV antibody of the invention are used to create structurally related human anti-HCV antibodies that retain at least one functional property of the antibodies of the invention, such as, for example, binding to HCV or neutralizing HCV. In one embodiment, one or more CDR regions of antibodies of the invention can be combined recombinantly with known human framework regions and CDRs to create additional, recombinantly-engineered, human anti-HCV antibodies of the invention. The heavy and light chain variable framework regions can be derived from the same or different human antibody sequences. The human antibody sequences can be the sequences of naturally occurring human antibodies or can be consensus sequences of several human antibodies. See Kettleborough et al, *Protein Engineering* 4:773 (1991); Kolbinger et al., *Protein Engineering* 6:971 (1993) and Carter et al., WO 92/22653.

Accordingly, in another embodiment, the invention provides a method for preparing a human anti-HCV antibody including: preparing an antibody including (1) human heavy chain framework regions and human heavy chain CDRs, where at least one of the human heavy chain CDRs includes an amino acid sequence selected from the human heavy chain CDR amino acid sequences described herein; and (2) human light chain framework regions and human light chain CDRs, where at least one of the human heavy chain CDRs includes an amino acid sequence selected from the human light chain CDR amino acid sequences described herein, where the antibody retains the ability to bind to HCV. The ability of the antibody to bind HCV can be determined using standard binding assays, such as those set forth in the Examples (e.g., an ELISA or a FLISA).

It is well known in the art that antibody heavy and light chain CDR3 domains play a particularly important role in the binding specificity/affinity of an antibody for an antigen (see, Hall et al., *J. Immunol.,* 149:1605-1612 (1992); Polymenis et al., *J. Immunol.,* 152:5318-5329 (1994); Jahn et al., *Immunobiol.,* 193:400-419 (1995); Klimka et al., *Brit. J. Cancer,* 83:252-260 (2000); Beiboer et al., *J. Mol. Biol,* 296:833-849 (2000); Rader et al., *Proc. Natl. Acad. Sci. USA,* 95:8910-8915 (1998); Barbas et al., *J. Am. Chem. Soc.,* 116:2161-2162 (1994); Ditzel et al., *J. Immunol.,* 157:739-749 (1996)). Accordingly, the recombinant antibodies of the invention prepared as set forth above preferably comprise the heavy and/or light chain CDR3s of antibodies 83-128, 95-2, 95-14, 95-38, and 073-1. The antibodies further can comprise the CDR2s of antibodies 83-128, 95-2, 95-14, 95-38, and 073-1. The antibodies further can comprise the CDR1s of antibodies 83-128, 95-2, 95-14, 95-38, and 073-1. The antibodies can further comprise any combinations of the CDRs.

Accordingly, in another embodiment, the invention further provides anti-HCV antibodies comprising: (1) human heavy chain framework regions, a human heavy chain CDR1 region, a human heavy chain CDR2 region, and a human heavy chain CDR3 region, wherein the human heavy chain CDR3 region is selected from the CDR3s of 83-128, 95-2, 95-14, 95-38, and 073-1, for example, a human heavy chain CDR3 region of 95-2 as shown in the sequence listing described herein; and (2) human light chain framework regions, a human light chain CDR1 region, a human light chain CDR2 region, and a human light chain CDR3 region, wherein the human light chain CDR3 region is selected from the CDR3s of 83-128, 95-2, 95-14, 95-38, and 073-1 for example, a human light chain CDR3 region of 95-2 as shown in the sequence listing described herein wherein the antibody binds HCV. The antibody may further include the heavy chain CDR2 and/or the light chain CDR2 of antibodies 83-128, 95-2, 95-14, 95-38, and 073-1The antibody may further comprise the heavy chain CDR1 and/or the light chain CDR1 of 83-128, 95-2, 95-14, 95-38, and 073-1.

The CDR1, 2, and/or 3 regions of the engineered antibodies described above can comprise the exact amino acid sequence(s) as those of antibodies 83-128, 95-2, 95-14, 95-38, and 073-1 disclosed herein. However, the ordinarily skilled artisan will appreciate that some deviation from the exact CDR sequences of 83-128, 95-2, 95-14, 95-38, and 073-1 may be possible while still retaining the ability of the antibody to bind HCV effectively (e.g., conservative sequence modifications). Accordingly, in another embodiment, the engineered antibody may be composed of one or more CDRs that are, for example, 90%, 95%, 98% or 99.5% identical to one or more CDRs of antibodies 83-128, 95-2, 95-14, 95-38, and 073-1.

In another embodiment, one or more residues of a CDR may be altered to modify binding to achieve a more favored on-rate of binding, a more favored off-rate of binding, or both, such that an idealized binding constant is achieved. Using this strategy, an antibody having ultra high binding affinity of, for example, a $K_D 10^{-10}$ M or lower, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

In addition to, or instead of, modifications within the CDRs, modifications can also be made within one or more of the framework regions, FR1, FR2, FR3 and FR4, of the heavy and/or the light chain variable regions of a human antibody, so long as these modifications do not eliminate the binding affinity of the human antibody. The amino acids at several positions in the framework are known to be important for determining CDR confirmation (e.g., capable of interacting with the CDRs) in many antibodies (Chothia and Lesk, supra, Chothia et al., supra and Tramontano et al., J. Mol. Biol. 215:175 (1990), all of which are incorporated herein by reference). These authors identified conserved framework residues important for CDR conformation by analysis of the structures of several known antibodies. The antibodies analyzed fell into a limited number of structural or "canonical" classes based on the conformation of the CDRs. Conserved framework residues within members of a canonical class are referred to as "canonical" residues. Canonical residues include residues 2, 25, 29, 30, 33, 48, 64, 71, 90, 94 and 95 of the light chain and residues 24, 26, 29, 34, 54, 55, 71 and 94 of the heavy chain. Additional residues (e.g., CDR structure-determining residues) can be identified according to the methodology of Martin and Thorton (1996) *J. Mol. Biol.* 263:800. Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs. Additional residues which may effect conformation of the CDRs can be identified according to the methodology of Foote and Winter (1992) *J. Mol. Biol.* 224:487. Such residues are termed "vernier" residues and are those residues in the framework region closely underlying (i.e., forming a "platform" under) the CDRs.

Residues which "participate in the $V_L$-$V_H$ interface" or "packing residues" include those residues at the interface between $V_L$ and $V_H$ as defined, for example, by Novotny and Haber, *Proc. Natl. Acad. Sci. USA,* 82:4592-66 (1985) or Chothia et al, supra.

Occasionally, there is some ambiguity about whether a particular amino acid falls within one or more of the above-mentioned categories. In such instances, alternative variant antibodies are produced, one of which has that particular substitution, the other of which does not. Alternative variant antibodies so produced can be tested in any of the assays described herein for the desired activity, and the preferred antibody selected.

Additional candidates for substitution within the framework region are amino acids that are unusual or "rare" for a human antibody at that position. These amino acids can be substituted with amino acids from the equivalent position of the human germline sequence or from the equivalent positions of more typical human antibodies. For example, substitution may be desirable when the amino acid in a human framework region of the human antibody is rare for that position and the corresponding amino acid in the germline sequence is common for that position in human immunoglobulin sequences; or when the amino acid in the human antibody is rare for that position and the corresponding amino acid in the germline sequence is also rare, relative to other human sequences. It is contemplated that by replacing an unusual amino acid with an amino acid from the germline sequence that happens to be typical for human antibodies, the human antibody may be made less immunogenic.

The term "rare", as used herein, indicates an amino acid occurring at that position in less than about 20%, preferably less than about 10%, more preferably less than about 5%, even more preferably less than about 3%, even more preferably less than about 2% and even more preferably less than about 1% of sequences in a representative sample of sequences, and the term "common", as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Kabat et al., supra). When deciding whether an amino acid in a human antibody sequence is "rare" or "common" among human sequences, it will often be preferable to consider only those human sequences in the same subgroup as the human antibody sequence.

In general, the framework regions of human antibodies are usually substantially identical, and more usually, identical to the framework regions of the human germline sequences from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting human immunoglobulin. Thus, in one embodiment the variable framework region of the human antibody shares at least 85% sequence identity to a human germline variable framework region sequence or consensus of such sequences. In another embodiment, the variable framework region of the human antibody shares at least 90%, 95%, 96%, 97%, 98% or 99% sequence identity to a human germline variable framework region sequence or consensus of such sequences.

In addition to simply binding a linear epitope of an HCV E2 protein, a monoclonal antibody may be selected for its retention of other functional properties of antibodies of the invention, such as binding to multiple genotypes of HVC E2 and/or binding with an ultra high affinity such as, for example, a $K_D$ of $10^{-9}$M or lower.

Characterization of Human Monoclonal Antibodies to HCV

Human monoclonal antibodies of the invention can be characterized for binding to HCV using a variety of known techniques. Generally, the antibodies are initially characterized by ELISA. Briefly, microtiter plates can be coated with purified HCV in PBS, and then blocked with irrelevant proteins such as bovine serum albumin (BSA) diluted in PBS. Dilutions of plasma from HCV-immunized mice are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

An ELISA assay as described above can be used to screen for antibodies and, thus, hybridomas that produce antibodies that show positive reactivity with the HCV immunogen. Hybridomas that bind, preferably with high affinity, to HCV can then be subcloned and further characterized. One clone from each hybridoma, which retains the reactivity of the parent cell (by ELISA), can then be chosen for making a cell bank, and for antibody purification.

To purify human anti-HCV antibodies, selected hybridomas can be grown in roller bottles, two-liter spinner-flasks or other culture systems. Supernatants can be filtered and concentrated before affinity chromatography with protein A-sepharose (Pharmacia, Piscataway, N.J.) to purify the protein. After buffer exchange to PBS, the concentration can be determined by $OD_{280}$ using 1.43 extinction coefficient or preferably by nephelometric analysis. IgG can be checked by gel electrophoresis and by antigen specific method.

To determine if the selected human anti-HCV monoclonal antibodies bind to unique epitopes, each antibody can be biotinylated using commercially available reagents (Pierce, Rockford, Ill.). Biotinylated MAb binding can be detected with a streptavidin labeled probe. To determine the isotype of purified antibodies, isotype ELISAs can be performed using art recognized techniques. For example, wells of microtiter plates can be coated with 10 μg/ml of anti-human Ig overnight at 4° C. After blocking with 5% BSA, the plates are reacted with 10 μg/ml of monoclonal antibodies or purified isotype controls, at ambient temperature for two hours. The wells can then be reacted with either human IgG1 or other human isotype specific conjugated probes. Plates are developed and analyzed as described above.

Anti-HCV human IgGs can be further tested for reactivity with the HCV antigen by Western blotting. Briefly, cell extracts from cells expressing HCV can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

II. Production of Transgenic Nonhuman Animals which Generate Human Monoclonal Anti-HCV Antibodies In yet another aspect, the invention provides transgenic non-human animals, such as transgenic mice, which are capable of expressing human monoclonal antibodies that specifically bind to HCV. In a particular embodiment, the invention provides a transgenic mouse having a genome comprising a human heavy chain transgene, such that the mouse produces human anti-HCV antibodies when immunized with HCV antigen and/or cells expressing HCV. The human heavy chain transgene can be integrated into the chromosomal DNA of the mouse, as is the case for transgenic, e.g., HuMAb mice, as described in detail herein and exemplified. Such transgenic mice are capable of producing multiple isotypes of human monoclonal antibodies to HCV (e.g., IgG) by undergoing V-D-J recombination and isotype switching. Isotype switching may occur by, e.g., classical or non-classical isotype switching.

The design of a transgenic non-human animal that responds to foreign antigen stimulation with a heterologous antibody repertoire requires that the heterologous immunoglobulin transgenes contained within the transgenic animal function correctly throughout the pathway of B-cell development. This includes, for example, isotype switching of the heterologous heavy chain transgene. Accordingly, transgenes are constructed so as to produce isotype switching and one or more of the following of antibodies: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology,* 2nd edition (1989), Paul William E., ed. Raven Press, N.Y.

In certain embodiments, the transgenic non-human animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B-cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al., *Nucl. Acids Res.* 15:7305-7316 (1991); Sideras et al., *Intl. Immunol.* 1:631-642 (1989)). For each of the foregoing transgenic animals, functionally rearranged heterologous heavy and light chain immunoglobulin transgenes are found in a significant fraction of the B-cells of the transgenic animal (at least 10 percent).

The transgenes used to generate the transgenic animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to the HCV antigen.

In an alternate embodiment, the transgenes comprise an unrearranged "mini-locus". Such transgenes typically comprise a substantial portion of the C, D, and J segments as well as a subset of the V gene segments. In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

In a preferred embodiment of the invention, the transgenic animal used to generate human antibodies to HCV contains at least one, typically 2-10, and sometimes 25-50 or more copies of the transgene described in Example 12 of WO 98/24884 (e.g., pHC1 or pHC2) bred with an animal containing a single copy of a light chain transgene described in Examples 5, 6, 8, or 14 of WO 98/24884, and the offspring bred with the $J_H$ deleted animal described in Example 10 of WO 98/24884. Animals are bred to homozygosity for each of these three traits. Such animals have the following genotype: a single copy (per haploid set of chromosomes) of a human heavy chain unrearranged mini-locus (described in Example 12 of WO 98/24884), a single copy (per haploid set of chromosomes) of a rearranged human K light chain construct (described in Example 14 of WO 98/24884), and a deletion at each endogenous mouse heavy chain locus that removes all of the functional $J_H$ segments (described in Example 10 of WO 98/24884). Such animals are bred with mice that are homozygous for the deletion of the $J_H$ segments (Examples 10 of WO 98/24884) to produce offspring that are homozygous for the $J_H$ deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regards to human or mouse heavy chains because both endogenous mouse heavy chain gene copies are nonfunctional by virtue of the deletion spanning the $J_H$ region introduced as described in Example 9 and 12 of WO 98/24884. Furthermore, a substantial fraction of the B cells will be monospecific with regards to the human or mouse light chains because expression of the single copy of the rearranged human κ light chain gene will allelically and isotypically exclude the rearrangement of the endogenous mouse κ and lambda chain genes in a significant fraction of B-cells.

Transgenic mice employed in the present invention exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10:1. The IgG to IgM ratio will be much lower in the immature mouse. In general, greater than about 10%, preferably 40 to 80% of the spleen and lymph node B cells express exclusively human IgG protein.

The repertoire will ideally approximate that shown in a native mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, e.g., *staphylococcus* protein A. Typically, the immunoglobulins will exhibit an affinity ($K_D$) for preselected antigens of below $10^{-7}$ M, such as of below $10^{-8}$ M, $10^{-9}$ M or $10^{-10}$ M or even lower.

It may be preferable to generate mice with predetermined repertoires to limit the selection of V genes represented in the antibody response to a predetermined antigen type. A heavy chain transgene having a predetermined repertoire may comprise, for example, human $V_H$ genes which are preferentially used in antibody responses to the predetermined antigen type in humans. Alternatively, some $V_H$ genes may be excluded from a defined repertoire for various reasons (e.g., have a low likelihood of encoding high affinity V regions for the predetermined antigen; have a low propensity to undergo somatic mutation and affinity sharpening; or are immunogenic to certain humans). Thus, prior to rearrangement of a transgene containing various heavy or light chain gene segments, such gene segments may be readily identified, e.g. by hybridization or DNA sequencing, as being from a species of organism other than the transgenic animal.

Transgenic mice as described above can be immunized with, for example, a purified or enriched preparation of HCV antigen and/or cells expressing HCV proteins. Alternatively, the transgenic mice can be immunized with DNA encoding HCV proteins. The mice will then produce B cells which undergo class-switching via intratransgene switch recombination (cis-switching) and express immunoglobulins reactive with HCV. The immunoglobulins can be human antibodies (also referred to as "human sequence antibodies"), wherein the heavy and light chain polypeptides are encoded by human transgene sequences, which may include sequences derived by somatic mutation and V region recombinatorial joints, as well as germline-encoded sequences; these human antibodies can be referred to as being substantially identical to a polypeptide sequence encoded by a human $V_L$ or $V_H$ gene segment and a human $J_L$ or $D_H$ and $J_H$ segment, even though other non-germline sequences may be present as a result of somatic mutation and differential V-J and V-D-J recombination joints. The variable regions of each antibody chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

Human antibodies which bind to the predetermined antigen can result from isotype switching, such that human antibodies comprising a human sequence γ chain (such as γ1, γ2a, γ2b, or γ3) and a human sequence light chain (such as kappa) are produced. Such isotype-switched human antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. These high affinity human antibodies may have binding affinities ($K_D$) of below $10^{-7}$M, such as of below $10^{-8}$ M, $10^{-9}$ M or $10^{-10}$ M or even lower.

Another aspect of the invention includes B cells derived from transgenic mice as described herein. The B cells can be used to generate hybridomas expressing human monoclonal antibodies which bind with high affinity (e.g., $K_D$ lower than $10^{-7}$M) to human HCV. Thus, in another embodiment, the invention provides a hybridoma which produces a human antibody having an affinity ($K_D$) of below $10^{-7}$ M, such as of below $10^{-8}$ M, $10^{-9}$ M or $10^{-10}$ M or even lower when determined by surface plasmon resonance (SPR) technology in a BIACORE 3000 instrument using recombinant human HCV as the analyte and the antibody as the ligand for binding human HCV, wherein the antibody comprises:

a human sequence light chain composed of (1) a light chain variable region having a polypeptide sequence which is substantially identical to a polypeptide sequence encoded by a human $V_L$ gene segment and a human $J_L$ segment, and (2) a light chain constant region having a polypeptide sequence which is substantially identical to a polypeptide sequence encoded by a human $C_L$ gene segment; and a human sequence heavy chain composed of a (1) a heavy chain variable region having a polypeptide sequence which is substantially identical to a polypeptide sequence encoded by a human $V_H$ gene segment, optionally a D region, and a human $J_H$ segment, and (2) a constant region having a polypeptide sequence which is substantially identical to a polypeptide sequence encoded by a human $C_H$ gene segment.

The development of high affinity human monoclonal antibodies against HCV can be facilitated by a method for expanding the repertoire of human variable region gene segments in a transgenic mouse having a genome comprising an integrated human immunoglobulin transgene, said method comprising introducing into the genome a V gene transgene comprising V region gene segments which are not present in said integrated human immunoglobulin transgene. Often, the V region transgene is a yeast artificial chromosome comprising a portion of a human $V_H$ or $V_L$ ($V_K$) gene segment array, as may naturally occur in a human genome or as may be spliced together separately by recombinant methods, which may include out-of-order or omitted V gene segments. Often at least five or more functional V gene segments are contained on the YAC. In this variation, it is possible to make a transgenic mouse produced by the V repertoire expansion method, wherein the mouse expresses an immunoglobulin chain comprising a variable region sequence encoded by a V region gene segment present on the V region transgene and a C region encoded on the human Ig transgene. By means of the V repertoire expansion method, transgenic mice having at least 5 distinct V genes can be generated; as can mice containing at least about 24 V genes or more. Some V gene segments may be non-functional (e.g., pseudogenes and the like); these segments may be retained or may be selectively deleted by recombinant methods available to the skilled artisan, if desired.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a mouse germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast is no longer necessary (i.e., prior to introduction into a mouse ES cell or mouse prozygote). Methods of propagating the trait of human sequence immunoglobulin expression, include breeding a transgenic mouse having the human Ig transgene(s), and optionally also having a functional YAC having an expanded V segment repertoire. Both $V_H$ and $V_L$, gene segments may be present on the YAC. The transgenic mouse may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal of the invention, other embodiments are contemplated which have been classified in four categories:

I. Transgenic animals containing an unrearranged heavy and rearranged light immunoglobulin transgene;

II. Transgenic animals containing an unrearranged heavy and unrearranged light immunoglobulin transgene;

III. Transgenic animal containing rearranged heavy and an unrearranged light immunoglobulin transgene; and IV. Transgenic animals containing rearranged heavy and rearranged light immunoglobulin transgenes.

Of these categories of transgenic animal, the preferred order of preference is as follows II>I>III>IV where the endogenous light chain genes (or at least the K gene) have been knocked out by homologous recombination (or other method) and I>II>III>IV where the endogenous light chain genes have not been knocked out and must be dominated by allelic exclusion.

III. Antibody Conjugates/Immunotoxins

In another aspect, the present invention features a human anti-HCV monoclonal antibody conjugated to a therapeutic moiety, such as a cytotoxin, a drug (e.g., an immunosuppressant) or a radioisotope. When conjugated to a cytotoxin, these antibody conjugates are referred to as “immunotoxins.” A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a HCV-related disorder, such as a cancer.

The antibody conjugates of the invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 (“IL-1”), interleukin-2 (“IL-2”), interleukin-6 (“IL-6”), granulocyte macrophage colony stimulating factor (“GM-CSF”), granulocyte colony stimulating factor (“G-CSF”), or other cytokines or growth factors.

Techniques for conjugating such therapeutic moiety to antibodies are well known, see, e.g., Amon et al., “Monoclonal Antibodies For Immunotargeting Of Drugs In Cancer Therapy”, in Monoclonal Antibodies And Cancer Therapy, Reisfeld et al. (eds.), pp. 243-56 (Alan R. Liss, Inc. 1985); Hellstrom et al., “Antibodies For Drug Delivery”, in Controlled Drug Delivery (2nd Ed.), Robinson et al. (eds.), pp. 623-53 (Marcel Dekker, Inc. 1987); Thorpe, “Antibody Carriers Of Cytotoxic Agents In Cancer Therapy: A Review”, in Monoclonal Antibodies ’84: Biological And Clinical Applications, Pinchera et al. (eds.), pp. 475-506 (1985); “Analysis, Results, And Future Prospective Of The Therapeutic Use Of Radiolabeled Antibody In Cancer Therapy”, in Monoclonal Antibodies For Cancer Detection And Therapy, Baldwin et al. (eds.), pp. 303-16 (Academic Press 1985), and Thorpe et al., “The Preparation And Cytotoxic Properties Of Antibody-Toxin Conjugates”, Immunol. Rev., 62:119-58 (1982).

IV. Pharmaceutical Compositions

In another aspect, the present invention provides a composition, e.g., a pharmaceutical composition, containing one or a combination of human monoclonal antibodies, or antigen-binding portion(s) thereof, of the present invention, formulated together with a pharmaceutically acceptable carrier. In a preferred embodiment, the compositions include a combination of multiple (e.g., two or more) isolated human antibodies of the invention. Preferably, each of the antibodies of the composition binds to a distinct, pre-selected epitope of HCV.

Pharmaceutical compositions of the invention also can be administered in combination therapy, i.e., combined with other agents. For example, the combination therapy can include a composition of the present invention with at least one or more additional therapeutic agents, such as anti-inflammatory agents, DMARDs (disease-modifying anti-rheumatic drugs), immunosuppressive agents, chemotherapeutics, and psoriasis agents. The pharmaceutical compositions of the invention can also be administered in conjunction with radiation therapy. Co-administration with other antibodies, such as CD4 specific antibodies and IL-2 specific antibodies, are also encompassed by the invention. Such combinations with CD4 specific antibodies or IL-2 specific antibodies are considered particularly useful for treating autoimmune diseases and transplant rejections.

As used herein, “pharmaceutically acceptable carrier” includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A “pharmaceutically acceptable salt” refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the human antibodies of the invention may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

A "therapeutically effective dosage" for rheumatoid arthritis preferably will result in an ACR20 Preliminary Definition of Improvement in the patients, more preferred in an ACR50

Preliminary Definition of Improvement and even more preferred in an ARCD70 Preliminary Definition of Improvement.

ACR20 Preliminary Definition of Improvement is defined as:

≥20% improvement in: Tender Joint Count (TCJ) and Swollen Joint Count (SWJ)

and ≥20% improvement in 3 of following 5 assessments: Patient Pain Assessment (VAS), Patient Global assessment (VAS), Physician Global Assessment (VAS), Patient Self-Assessed Disability (HAQ), Acute Phase Reactant (CRP or ESR).

ACR50 and ACR70 are defined in the same way with ≥50% and ≥70% improvements, respectively. For further details see Felson et al. in American College of Rheumatology Preliminary Definition of Improvement in Rheumatoid Arthritis; Arthritis Rheumatism (1995) 38: 727-735.

The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The ability of the antibodies to treat or prevent cirrhosis can also be evaluated according to methods well known in the art.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

V. Uses and Methods of the Invention

Human anti-HCV antibodies to HCV of the present invention (including derivatives and conjugates of the antibodies) and compositions containing the antibodies can be used in a variety of in vitro and in vivo diagnostic and therapeutic applications. For example, the human monoclonal antibodies of the invention can be used for treating HCV-mediated disorders, including but not limited to, liver disorders, such as cirrhosis, hepatocellular carcinoma, and hepatocarcinogenesis.

Accordingly, in yet another embodiment, the present invention provides a method for treating or preventing a disorder mediated by HCV (e.g., a liver disorder), by administering to a subject a human antibody of the invention in an amount effective to treat or prevent the disorder. The antibody can be administered alone or along with another therapeutic agent, such as alpha-IFN or a cytotoxin which acts in conjunction with or synergistically with the antibody to treat or prevent the HCV mediated disease. Other disorders suitable for treatment using the antibodies of the invention include HCV-mediated hepatocyte pathologies, HCV-mediated cirrhosis of the liver, and/or HCV-mediated liver cancer.

Additionally, the antibodies of the invention can be used in vitro or in vivo to diagnose a variety of diseases mediated by HCV. Specifically, the antibodies can be used to detect levels of HCV, or levels of cells which contain HCV. Alternatively, the antibodies can be used to inhibit or neutralize HCV function which, in turn, can prevent or ameliorate disease symptoms caused by HCV function.

Also within the scope of the present invention are kits comprising human anti-HCV antibodies of the invention and, optionally, instructions for use. The kit can further contain one or more additional reagents, such as alpha-IFN or one or more additional human antibodies of the invention (e.g., a human antibody having a complementary activity which binds to an epitope of an HCV antigen distinct from the first human antibody).

Accordingly, patients treated with antibodies of the invention can be additionally administered (prior to, simultaneously with, or following administration of a human antibody of the invention) with another therapeutic agent which enhances or augments the therapeutic effect of the human antibodies.

Other embodiments of the present invention are described in the following Examples.

The present invention is further illustrated by the following examples which should not be construed as further limiting. The contents of Sequence Listing, figures and all references, patents and published patent applications cited throughout this application are expressly incorporated herein by reference.

EXAMPLES

The invention is further described in the following examples, which do not limit the scope of the invention described in the claims.

Materials and Methods

Throughout the examples, the following materials and methods were used unless otherwise stated.

In general, the practice of the present invention employs, unless otherwise indicated, conventional techniques of chemistry, molecular biology, recombinant DNA technology, immunology (especially, e.g., antibody technology), and standard techniques in polypeptide preparation. See, e.g., Sambrook, Fritsch and Maniatis, *Molecular Cloning: Cold Spring Harbor Laboratory Press* (1989); *Antibody Engineering Protocols* (*Methods in Molecular Biology*), 510, Paul, S., Humana Pr (1996); *Antibody Engineering: A Practical Approach* (Practical Approach Series, 169), McCafferty, Ed., Irl Pr (1996); *Antibodies: A Laboratory Manual*, Harlow et al., C.S.H.L. Press, Pub. (1999); and *Current Protocols in Molecular Biology*, eds. Ausubel et al., John Wiley & Sons (1992). In vitro and in vivo model systems for assaying HCV biology are described, for example, in *Cell culture models and animal models of viral hepatitis. Part II: hepatitis C, Lab. Anim.* (NY).; 34(2):39-47 (2005) and in *The chimpanzee model of hepatitis C virus infections, ILAR J.;* 42(2):117-26 (2001).

Assembly of Codon Optimized HCV Genotype 1a E1/E2 Expression Construct

Briefly, a nucleic acid sequence encoding an E2 genotype 1a, strain H77 (prototype 1a sequence) protein sequence (Genbank accession number NC004102) was constructed and engineered into pCDNA vector. The nucleotide sequence was altered for optimized codon usage for improved mammalian expression. The sequence was assembled using overlapping PCR with oligonucleotides purchased from IDT and cloned into the pCDNA3.1-myc, his expression vector with HindIII and XbaI in frame with the C-terminal myc and 6 histidine tags. The vector was then sequenced to confirm the construct was correct.

The E1/E2 codon optimized 1a H77 sequence with added ends containing restrictions sites (bold lowercase), additional overhangs to insure restriction enzyme cutting (underlined lowercase), and consensus Kozak sequence (bold underlined lowercase) with ATG initiation codon (bold underlined uppercase) (see SEQ ID NO: 27 and FIG. 13).

Assembly of Codon-Optimized HCV Genotype 1a E2-661 Expression Construct to Express Soluble E2 Protein (pCDNA-1a-CO-E2-661)

The portion of the E2 protein encoding amino acids 364 to 661 was PCR amplified using pCDNA-1a-CO-E1/E2 as template and cloned into pCDNA3.1-his expression vector with HindIII and XbaI in frame with the C-terminal 6 histidine tag. The vector was sequenced to confirm the construct was correct.

Expression and Purification of Codon Optimized HCV Genotype 1a E2-661

293T human tissue culture cells were transiently transfected using Lipofectamine 2000 (Invitrogen). Supernatant from the cells containing secreted proteins was collected and 1a E2-661 was purified from the supernatant using nickel affinity chromatography. The protein concentration was determined based on OD 280 nm and further evaluated by Coomassie stained SDS-PAGE and Western blot with commercially available E2 mouse antibody from Biodesign International Assembly of Wildtype HCV Genotype 1a E1/E2 Expression Vector (pCDNA-1a-E1/E2)

The E1/E2 of HCV1a H77 encoding sequence (amino acids 165-746) was PCR amplified with primers to introduce HindIII and XbaI cloning sites, a consensus Kozak sequence and an initiation codon, and was then cloned into the pCDNA3.1-his expression vector with HindIII and XbaI in frame with the C-terminal 6 histidine tag. The vector was sequenced to confirm the construct was correct.

Assembly of Wildtype HCV Genotype 1a E2-660 Expression Vector (pCDNA-1a-E2-660)

The portion of E2 protein encoding amino acids 364 to 660 was PCR amplified using pCDNA-1a-E1/E2 as template and cloned into pCDNA3.1-his expression vector with HindIII and XbaI in frame with the C-terminal 6 histidine tag. The vector was sequenced to confirm the construct was correct.

Assembly of HCV Genotype 1b, 2b, 3a and 4a E1/E2 Expression Vectors (pCDNA-E1/E2)

High titer genotype 1b, 2b, 3a and 4a HCV positive patient serum was obtained and RNA was isolated from the serum. RT-PCR was performed on the isolated RNA with genotype specific primers complimentary to the end of the core gene and for the p7 gene that flanks the E1/E2 genes. PCR was used to amplify the E1/E2 encoding sequence (amino acids 165-746) using primers to introduce HindIII and XbaI cloning sites, a consensus Kozak sequence and an initiation codon. The sequence was cloned into pCDNA3.1-his expression vector with HindIII and XbaI in frame with the C-terminal 6 histidine tag and then sequenced. A blast search confirmed that the sequences were the expected genotype, but the sequences had no exact match in the database.

Assembly of HCV Genotype1b E2-661 Expression Vector (pCDNA-1b-E2-661)

PCR was used to amplify the portion of E2 protein encoding amino acids 364 to 661 using pCDNA-1b-E1/E2 as template. The sequence was then cloned into pCDNA3.1-his expression vector with HindIII and XbaI in frame with the C-terminal 6 histidine tag. The vector was then sequenced to confirm the construct was correct. Expression and purification was carried out essentially as described above for 1a E2-661.

Assembly of HCV Genotype 1a E2 Hvr1 Deletion Expression Vector

In order to generate an E1/E2 encoding construct with a deletion of the nucleotides encoding the hypervariable region 1 (HVR1) of E2, E1 was PCR amplified using a 3' primer containing an overhang for a region of E2 beginning with amino acids 411 (skipped over amino acids 384 to 410-HVR1) using pCDNA-1a-E1/E2 as template. In a separate reaction, the E2 region encoding amino acids 411-746 was PCR amplified using a 5' primer containing an overhang for the 3' end of E1 using pCDNA-1a-E1/E2 as template. The E1 and E2 PCR products that contained complementary overhangs at the E1-E2 junction without the region encoding the HVR1 for E2 were mixed, and then PCR amplified using a primer specific for the 5' end of E1 with a HindIII site and 3' end of E2 with an XbaI site. The sequence was cloned into pCDNA3.1-his expression vector with HindIII and XbaI in frame with the C-terminal 6 histidine tag. The vector was then sequenced to confirm that the construct was correct.

Assembly of Codon Optimized HCV Genotype 1a E2 Trunction Expression Vectors

Truncations for mammalian expression were engineered in which amino acids from the C-terminus of E2 were removed. The portion of E2 protein encoding desired amino acids was PCR amplified using pCDNA-1a-CO-E1/E2 as template and cloned into pCDNA3.1-his expression vector with HindIII and XbaI in frame with the C-terminal 6 histidine tag. The vector was then sequenced to confirm that the construct was correct. The following constructs were made:

pCDNA-1a-CO-E2-624 (E2 amino acids 384 to 624)
pCDNA-1a-CO-E2-584 (E2 amino acids 384 to 584)
pCDNA-1a-CO-E2-544 (E2 amino acids 384 to 544)
pCDNA-1a-CO-E2-504 (E2 amino acids 384 to 504)
pCDNA-1a-CO-E2-464 (E2 amino acids 384 to 464)

Expression and purification from each construct was carried out essentially as described above for 1a E2-661.

Lectin ELISA

Lectin capture ELISA was carried out with the E2 truncations to determine antibody reactivity. Briefly, 96-well plates were coated with *Galanthus nivalis* (GNA) lectin. E2 truncations from the supernatants of transiently transfected 293 cells were added to the 96-well plates coated with GNA lectin in order to capture the protein. Hybridoma supernatant was then added to the 96 well plates to determine protein reactivity. Bound antibody was detected with anti-human alkaline phosphatase secondary antibody and PNPP substrate.

Assembly of Bacterial Expression Constructs Spanning Amino Acids 384 to 464 of HCV Genotype 1a E2 Glycoprotein Next, fusion proteins were engineered with N-terminal thioredoxin fusion for bacterial expression in order to allow production of small portions of E2.

For the first set of proteins, the portion of E2 protein encoding the desired amino acids was PCR amplified using pCDNA-1a-E1/E2 as template and cloned into pET32 expression vector with EcoRI and HindIII in frame with the C-terminal myc and 6 histidine tags. The vector was then sequenced to confirm that the construct was correct. The following constructs were made:

pET32-E2-A (amino acids 384 to 463)
pET32-E2-B (amino acids 411 to 463)
pET32-E2-C (amino acids 432 to 463)
pET32-E2-D (amino acids 436 to 463)
pET32-E2-E (amino acids 384 to 431)

The vectors were transformed into BL21-DE3 *E. coli* bacteria (Invitrogen) and expression was induced with IPTG. Bacteria were lysed and the proteins of interest were purified with nickel affinity chromatography. Protein concentration was determined based on OD 280 nm and further evaluated by Coomassie stained SDS-PAGE and Western blot using mouse antibody specific for myc and histidine tags.

For the second set of proteins, complementary phosphorylated oligonucleotides were prepared that, when annealed, would have EcoRI and HindIII overhangs and encode the desired amino acids. The DNA was cloned into pET32 expression vector with EcoRI and HindIII in frame with the C-terminal myc and 6 histidine tags. The vector was then sequenced to confirm that the construct was correct. The following constructs were made:

pET32-E2-G (amino acids 412 to 423)
pET32-E2-H (amino acids 432 to 443)
pET32-E2-I (amino acids 436 to 447)

Expression and purification was carried out as described above for the first set of proteins.

Generation of Alanine Scanning Mutants of HCV E2-412-423 Epitope

Each amino acid in the 412-423 epitope was separately mutated to an alanine in the bacterial expression construct to determine the important amino acid contacts for the antibodies. Complementary phosphorylated oligonucleotides were prepared that, when annealed, would have EcoRI and HindIII overhangs and encode the E2 412-423 region with the desired changes. The DNA was cloned into the pET32 expression vector with EcoRI and HindIII in frame with the C-terminal myc and 6 histidine tags. The vector was then sequenced to confirm that the construct was correct.

The following constructs were made:

pET32-E2-G-Q412A (amino acid 412 from a Q to an A)
pET32-E2-G-L413A
pET32-E2-G-1414A
pET32-E2-G-N415A
pET32-E2-G-T416A
pET32-E2-G-N417A
pET32-E2-G-G418A
pET32-E2-G-S419A
pET32-E2-G-W420A
pET32-E2-G-H421A
pET32-E2-G-1422A
pET32-E2-G-N423A Expression and purification was carried out as described above for the other bacterial proteins.

Pseudovirus Generation and Neutralization Assay

A pseudovirus was generated having an HIV backbone that contained a mutation to prevent HIV envelope glycoprotein expression and a luciferase gene to direct luciferase expression in target cells (pNL4-3.Luc.R-E-). HCV E1/E2 glycoproteins were provided in trans by cotransfection of 293 cells with pcDNA E1/E2 derived from the various genotypes (1a, 1b, 2b, 3a and 4a) with pNL4-3.Luc.R-E-. Supernatant containing secreted virus particles was harvested from cells from 48 to 72 hrs post-transfection and concentrated using Centricon 70 concentrators and/or ultracentrifugation. Pseudovirus was then used to infect Hep3b cells (ATCC) in the presence or absence of antibody. Pseudovirus was preincubated with antibody for 1 hr at room temperature before adding to Hep3b cells. After incubation for 72 hrs, infection was quantitated by luciferase detection with BrightGlo luciferase assay (Promega) and read in a Victor3 plate reader (Perkin Elmer)

Biacore Affinity Determination

Goat-anti-human IgG (Fc) was amide coupled to a CM5 sensor chip from Biacore in flow cell 1 and 2. Human antibody (95-2 or 83-128) was captured in flow cell 2 only using HBS-P buffer (Biacore). E2-G was flowed over both flow cell 1 (for background) and flow cell 2 (for specific interaction with human antibody) at 125, 62.5, 31.3, and 15.6 nM in HBS-P buffer at 50 μl/min for 200 sec. After injection was stopped, buffer was flowed over both flow cells to collect dissociation data. Data was evaluated and curves fitted to determine the affinity constant using the BIAevaluation software Mouse Immunizations Mice transgenic for human IgG genes (HuMab mice) from Medarex were immunized with soluble E2 protein to generate an immune response. Mouse 85083 was immunized with 1a E2-661 with Freunds' adjuvant for 1 injection and MPL+TDM adjuvant (Sigma) for 14 injections. Mouse 97895 was immunized with 1a E2-661 with MPL+TDM+CWS adjuvant (Sigma) for 1 injection and MPL+TDM adjuvant for 5 injections Splenic Fusions and Hybridoma Selection Mouse spleens were removed and spleen cells were isolated. Spleen cells were fused to mouse myeloma cells following a standard PEG fusion protocol to generate hybridomas. Hybridoma supernatants were then screened for production of antibody reactive to 1a E2-661 by ELISA and positive cells were moved forward for further characterization.

Isolation and Sequencing of Hybridoma Antibody Genes

RNA was isolated from hybridoma cells using a Qiagen RNeasy kit. RT-PCR was performed for the heavy chain variable region with gene-specific primers containing restrictions sites, the resulting sequence was cloned and the construct was sequenced. RACE was performed for the light chain variable region with gene-specific primers. The sequence was cloned into the TOPO vector and the vector was sequenced. Gene specific primers were designed and used to PCR amplify and add restriction sites.

Example 1

Generation of Anti-HCV Monoclonal Antibodies

Mouse Immunizations, Hybridoma Production and Selection

Transgenic mice comprising human immunoglobulin genes generated as described above in the section entitled "Generation of Human Monoclonal Antibodies in HuMab Mice" and supplied by Medarex, Milpitas, Calif., were immunized with a soluble version of the HCV genotype 1a E2 envelope glycoprotein. The antigen was administered in combination with Freund's complete or RIBI adjuvant. Mouse sera responses were monitored by enzyme linked immunosorbent assay (ELISA) to soluble E2 protein (1a E2-661). Splenic B cells were isolated from the immunized animal and fused to mouse myeloma (P3X-AG8.653) cells using standard spleen cells fusion methods. Clonal hybridomas were generated and screened using ELISA for production of antibody reactive to E2-661. Positive hybridomas were tested for equivalent reactivity to HCV genotype 1a and genotype 1b E2-661 by ELISA with decreasing amounts of hybridoma supernatant. Hybridomas which exhibited equivalent reactivity to genotypes 1a E2-661 and 1b E2-661 were tested for capacity to neutralize HCV pseudovirus infectivity of Hep3b cells. This selection process yielded 20 hybridomas that neutralized HCV pseudovirus and had equivalent reactivity to 1a and 1b E2 soluble protein by ELISA. Specifically, nineteen (19) hybridomas were from mouse #97895 and produced IgG1 antibody as follows: 95-2; 95-14; 95-15; 95-18; 95-20; 95-21; 95-25; 95-26; 95-30; 95-38; 95-39; 95-42; 95-43; 95-48; 95-49; 95-52; 95-54; 95-58; and 95-62. One (1) hybridoma, 83-128, that neutralized HCV pseudovirus and had equivalent reactivity to 1a and 1b E2 soluble protein by ELISA was also identified from mouse #85083 and produced IgG3 antibody. One (1) hybridoma, 073-1, that neutralized HCV pseudovirus and had equivalent reactivity to 1a and 1b E2 soluble protein by ELISA was also identified from mouse #113073 and produced IgG3 antibody. These twentyone (21) hybridomas were further characterized.

Antibody Sequencing and Cloning

The heavy and light chain variable sequences of the human antibodies 83-128 (from the hybridoma from mouse #85083) and 073-1 (from the hybridoma from mouse #113073) were sequenced and cloned into vectors containing the heavy and light chain constant regions for human IgG1/kappa antibody. This changed human antibodies 83-128 and 073-1 from an IgG3 antibody to an IgG1 antibody.

The heavy chain variable sequences of the human antibodies from the nineteen (19) hybridomas from mouse #97895 were sequenced and compared. All nineteen (19) antibodies were found to share substantial sequence identity (i.e., >96% identical). Three (3) hybridomas, 95-2, 95-14, and 95-38, were chosen based on neutralization assay data and their light chain variable region sequences were determined. The heavy and light chain variable region sequences of human antibodies 95-2, 95-14, and 95-38 were cloned into vectors containing the heavy and light chain constant regions for human IgG1/kappa antibody. Antibody was expressed by transient transfection, purified, and directly compared in a HCV pseudovirus neutralization assay. Human antibody 95-2 from mouse #97895 was selected to be further characterized.

The amino acid sequences of the heavy chain variable region of antibodies produced by clones 95-14, 95-49, 95-62, 95-42, 95-58, 95-25, 95-43, 95-54, 95-2, 95-38, 83-128, 073-1 is set forth in SEQ ID NOs:32, 37, 40, 35, 39, 34, 36, 38, 3, 33, 1 and 5 respectively. The amino acid sequences of the light chain variable region of antibodies produced by clones 95-2, 95-14, 95-38, 073-1 and 83-128 is set forth in SEQ ID NOs:4, 44, 53, 6 and 2, respectively.

The nucleotide sequences encoding the heavy chain variable region of antibodies produced by clones 95-2, 95-14, 95-38, 073-1 and 83-128 is set forth in SEQ ID NOs:27, 48, 57, 29 and 25, respectively; and the nucleotide sequences encoding the light chain variable region of antibodies produced by clones 95-2, 95-14, 95-38, 073-1 and 83-128 is set forth in SEQ ID NOs:28, 49, 58, 30 and 26, respectively.

Example 2

Antibody Characterization

HCV Genotype 1a and 1b—Soluble E2 ELISA

The reactivity of human antibody 95-2 (FIG. 1A) and human antibody 83-128 (FIG. 1B) to soluble HCV genotype 1a E2-660 (triangles) and soluble HCV genotype 1b E2-661 (squares) was compared. ELISA plates were coated with 2 μg/ml of antigen and probed with antibody in two-fold dilutions. Bound antibody was detected with goat-anti-human secondary antibody conjugated to alkaline phosphatase and PNPP substrate. Both human antibodies, 95-2 and 83-128 were found to react equivalently to both genotypes (see FIG. 1). These experiments were also performed with the 95-14, 95-38 and 073-1 antibodies and all three recognized genotype 1a and 1b equivalently (data not shown).

Neutralization of HCV Pseudovirus from Multiple Genotypes

The capacity of human antibodies 95-2 and 83-128 to neutralize both multiple genotypes of HCV pseudovirus was determined using Hep3b cells. Five-fold dilutions of antibody were incubated with HCV pseudovirus for one hour at room temperature. The virus-antibody mixture was added to Hep3b cells followed by incubation at 37° C. for 72 hours. Infection was quantitated with Brightglo luciferase assay and read in a Victor3 plate reader for light output. An isotype-matched irrelevant human antibody was used as a negative control. Both human antibodies, 95-2 and 83-128, were found to neutralize HCV genotypes 1a, 1b, 2b, 3a and 4a pseudovirus (see FIGS. 2A, 2B, 2C, 2D and 2E, respectively). Antibody 073-1 was also shown to neutralize all of the above listed pseudovirus (data not shown).

Reducing and Non-Reducing Western Blots of Genotype 1a and 1b E2 Soluble Protein The reactivity of human antibodies 95-2 and 83-128 to soluble E2 protein (E2-661) from HCV genotype 1a and 1b subjected to reducing or non-reducing SDS-PAGE was analyzed. Westerns blots were performed with anti-his tag monoclonal (his), 83-128 and 95-2 using anti-mouse IgG (his) or anti-human IgG (95-2 and 83-128) conjugated to HRP with enhanced chemiluminescent detection reagent. Both human antibodies 95-2 and 83-128 were found to recognize E2-661 subjected to denaturing, reducing gel followed by transfer to PVDF membrane (see FIG. 3).

Binding Affinity of Human Antibodies 95-2 and 83-128 for E2 412-423 Epitope Expressed as a Bacterial Fusion Protein Binding affinity of human antibodies 95-2 and 83-128 for E2 412-423 epitope expressed as a bacterial fusion protein was determined and summarized in FIG. 4. Goat anti-human IgG Fc was amide coupled to the Biacore chip. Human antibodies 95-2 and 83-128 were separately captured on the chip and E2-G bacterially expressed protein containing E2 412-423 amino acids was flowed over at varying concentrations. The BIAevaluation™ software was used to fit the curves and calculate the affinity constants.

Example 3

Epitope Determination

Determination of which Region of the E2 Protein Human Antibodies 83-128 and 95-2 Recognize To determine which region of the E2 protein human antibodies 83-128 and 95-2 recognize, carboxy-terminal truncations of mammalian expressed E2 protein were captured by lectin ELISA and probed with 83-128 and 95-2 (see FIG. 5 for map of constructs and FIG. 6 for ELISA data). Based on the data, the epitope for these antibodies is within amino acids 412-464 of E2. As expected, all antibodies (95-14, 95-49, 95-62, 95-42, 95-58, 95-25, 95-43, 95-54, 95-2, 95-38, and 073-1) also mapped to this region of the E2 protein.

To further define the epitope, bacterially expressed fusion protein was used because the smaller pieces of E2 did not express well in the mammalian system. The purified proteins were coated on an ELISA plate and probed with human antibodies 83-128 and 95-2 (see FIG. 7 for map of constructs and FIG. 8 for ELISA data). Both human antibodies 83-128 and 95-2 recognized all constructs containing E2 amino acids 412-423, thus, identifying amino acids 412-423 as the epitope. This experiment was also performed using the 073-1 antibody and it also recognized the 412-423 epitope (data not shown).

To determine the important contacts within the 412-423 epitope, alanine scanning mutagenesis was used to individually change each amino acid in the 412-423 epitope to an alanine in the E2-G bacterial fusion protein. The purified proteins were coated on an ELISA plate and probed with both human antibodies (83-128 and 95-2). An anti-his monoclonal antibody specific for the $(His)_6$ epitope tag on the fusion proteins was used to control for coating of the plate (see FIG. 9). Based on the data, residues 413 and 420 were found to be critical for binding for human antibody 95-2; residues 413, 418 and 420 were found to be critical for binding for human antibody 83-128.

To determine the frequency of naturally occurring changes within the 412-423 epitope, this region of E2 was analyzed for sequences reported in the Los Alamos HCV sequence database that were condensed by manual optimization with only complete sequences and similar sequences reduced to one sequence. Based on the alignment (FIG. 10), 77.7% of the sequences in the condensed database are identical to the sequences in this region of the 1a and 1b expressed E2 proteins used in the present examples. Accordingly, human antibodies 95-2 and 83-128 should recognize these proteins.

Figure 11:
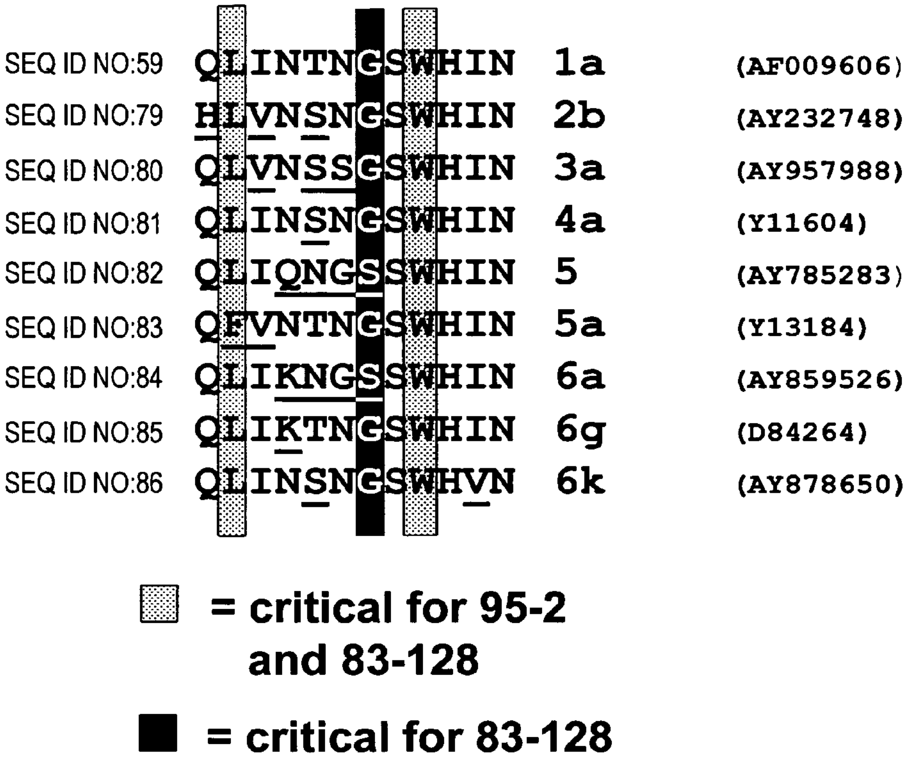
FIG. 11 is a table showing E2 amino acids 412-423 from other genotypes. The one-letter amino acid code for amino acids 412-423 is listed for isolates that contained changes (underlined) from the prototype genotype 1a sequence. The genotype name is listed to the right followed by the Genbank accession number in parenthesis.

To determine if some of the reported sequence differences in this region will affect human antibody 95-2 and 83-128 recognition, sequence changes were engineered into the E2-G bacterially expressed fusion protein containing the 412-423 epitope (FIG. 11). A sequence from a genotype 5 strain reported in Tarr et al. (2006) Hepatology (genbank accession number AY785283) was included that was not in the database. The purified proteins were coated on an ELISA plate that was probed with both antibodies (83-128 and 95-2). An anti-his monoclonal antibody specific for the his tag on the fusion proteins was used to control for coating of the plate (FIG. 12). Human antibody 95-2 recognized all constructs, with the exception of the genotype 6a, with a 10-fold reduction of this specific genotype 5 sequence. Human antibody 83-128 recognized all constructs, except the those derived from specific genotype 5 and 6a sequence, and had weak recognition of 5a.

Example 4

In Vitro Model

Human antibodies of the present invention are tested in in vitro models for antiviral activity and for the ability to inhibit HCV infection. Numerous in vitro models for HCV infection are known in the art and are used to test the human antibodies of the present invention, including, e.g., (i) infection of primary hepatocytes with HCV; (ii) stable transfection of hepatocyte cell lines; and (iii) transfection with full-length or subgenomic replicons, as described, e.g., in C. Guha et al. ("*Cell culture models and animal models of viral hepatitis. Part II: hepatitis C*" Lab Animal (NY) 2005, 34(2):39-47). Cultured cells in these in vitro models are exposed to human antibodies of the present invention, or to appropriate control antibodies, and the effect of the antibodies on HCV infection and viral activity are monitored by using standard techniques known in the art, e.g., by detecting HCV viral RNA, e.g., by using quantitative, real-time reverse transcription/polymerase chain reaction (RT/PCR).

Example 5

In Vivo Animal Model

Human antibodies of the present invention are tested in an in vivo animal model for the ability to inhibit hepatitis C viral infection. In particular, the human antibodies of the present invention are tested in a chimpanzee animal model as described in R. E. Lanford et al. (ILAR J. 2001; 42(2):117-26). As described in Lanford et al., the chimpanzee (Pan troglodytes) is the only experimental animal susceptible to infection with hepatitis C virus (HCV) and was instrumental in the initial studies on non-A, non-B hepatitis, including observations on the clinical course of infection, determination of the physical properties of the virus, and eventual cloning of the HCV nucleic acid. The chimpanzee model has been critical for the analysis of early events in HCV infection because it represents a population for which samples are available from the time of exposure and all exposed animals are examined. For this reason, the chimpanzee represents a truly nonselected population. In contrast, human cohorts are often selected for disease status or antibody reactivity and typically include individuals that have been infected for decades. The chimpanzee model is essential to an improved understanding of the factors involved in viral clearance, analysis of the immune response to infection, and the development of vaccines. The development of infectious cDNA clones of HCV was dependent on the use of chimpanzees, and they will continue to be needed in the use of reverse genetics to evaluate critical sequences for viral replication. In addition, chimpanzees have been used in conjunction with DNA microarray technology to probe the entire spectrum of changes in liver gene expression during the course of HCV infection. The chimpanzee will continue to provide a critical aspect to the understanding of HCV disease and the development of therapeutic modalities.

Accordingly, chimpanzees are inoculated with HCV and are additionally administered a human antibody of the present invention. Control animals are inoculated with HCV and are either not administered a human antibody of the present invention or are administered an appropriate control antibody. Human antibodies of the invention are administered to the chimpanzees either prior to HCV inoculation, at the time of HCV inoculation or subsequent to HCV inoculation. The effects of the human antibody on HCV infection, progression and clearance are then monitored by using assays standard in the art. For example, HCV infection and/or clearance can be monitored by: (i) measuring increases in serum alanine amino transferase (ALT) levels, indicating liver damage; (ii) detecting HCV viral RNA in serum by, e.g., quantitative, real-time reverse transcription/polymerase chain reaction (RT/PCR); and (iii) evaluation of anti-HCV antibody response, e.g., by enzyme-linked immunosorbent and recombinant immunoblot assays. These assays are known to those or ordinary skill in the art and are carried out, for example, as described in Lanford et al. Additionally, in experiments similar to those described above, the effects of the antibodies of the invention on the response to the HCV E1 and/or E2 proteins are evaluated, e.g., as described in Lanford et al. Downmodulation of HCV infection, a decrease in HCV progression or an increase in HCV clearance in the animals exposed to a human antibody of the invention, as compared to control animals, is indicative of the effectiveness of the antibody to prevent or treat HCV infection.

Additionally, DNA microarrays are used to monitor the effects of the human antibodies of the invention on the progressive changes in HCV infection in the chimpanzee by monitoring changes in gene expression in the liver of infected animals at multiple time points during the acute phase of infection and through viral clearance. DNA microarray analysis is conducted on liver tissue obtained before infection and at multiple time points throughout infection and clearance, e.g., up to week 16 after infection, in animals exposed to the antibody and in control animals not exposed to antibody. These studies may be conducted, for example, with the Affymetrix Human FL DNA microarray, which contains oligonucleotides representative of approximately 6800 genes, essentially as described in Lanford et al.

Example 6

Production of Anti-HCV Antibodies for Administration in Humans

Human antibodies of the present invention can be cloned and recombinantly expressed to facilitate or increase their production using known techniques.

Nucleic acid sequences encoding the variable heavy chain and light chains of an antibody clone of the invention can be cloned into a pIE-Ugamma1F vector using standard recombinant DNA methodology. The vector is amplified in *E. coli*, purified, and transfected into CHO cells. Transfected cells are plated at $4\times10^5$ cells per well in a 96-well dish and selected for vector transfection with G418. Resistant clones selected by G418 resistance, are then assayed along with other transfectomas for production of IgG. The expression of an antibody can be amplified by growth in the presence of increasing concentrations of methotrexate. A culture capable of growth in 175 nM methotrexate is chosen for cloning single cells for further development. Plating the culture in 96 well plates at low density allowed generation of cultures arising from a single cell or clones. The cultures are screened for production of human IgG, and the cell that produces the highest level of IgG is typically selected for further use. The methotrexate-amplified clone is expanded to produce a cell bank including multiple frozen vials of cells. Alternatively, glutamine synthetase (GS) vectors can be used with cell selection achieved using, e.g., methionine sulphoximine (see, e.g., U.S. Pat. Nos. 5,827,739; 5,122,464; 5,879,936; and 5,891,693).

To prepare antibodies from transfected cells, cells from a clone isolated in the previous steps are cultured and expanded as inoculum for a bioreactor. The bioreactor typically holds a 500 liter volume of culture medium. The cells are cultured in the bioreactor until cell viability drops, which indicates a maximal antibody concentration has been produced in the culture. The cells are removed by filtration. The filtrate is applied to a protein A column. Antibodies bind to the column, and are eluted with a low pH wash. Next, the antibodies are applied to a Q-Sepharose column to remove residual contaminants, such as CHO cell proteins, DNA, and other contaminants (e.g., viral contaminants, if present). Antibodies are eluted from the Q-Sepharose column, nano-filtered, concentrated, and washed in a buffer such as PBS. The preparation is then aseptically aliquoted into vials for administration.

EQUIVALENTS

Those skilled in the art will recognize, or be able to ascertain using no more than routine experimentation, many equivalents of the specific embodiments of the invention described herein. Such equivalents are intended to be encompassed by the following claims. Any combination of the embodiments disclosed in the dependent claims are contemplated to be within the scope of the invention.

INCORPORATION BY REFERENCE

All publications, patents, and pending patent applications referred to herein are hereby incorporated by reference in their entirety.

SUMMARY OF SEQUENCE LISTING

| SEQ ID NO. | Type | Description of Sequence |
|---|---|---|
| 1 | AA | VH of clone 83-128 |
| 2 | AA | VL of clone 83-128 |
| 3 | AA | VH of clone 95-2 |
| 4 | AA | VL of clone 95-2 |
| 5 | AA | VH of clone 073-1 |
| 6 | AA | VL of clone 073-1 |
| 7 | AA | CDR1 of VH of clone 83-128 |
| 8 | AA | CDR2 of VH of clone 83-128 |
| 9 | AA | CDR3 of VH of clone 83-128 |
| 10 | AA | CDR1 of VH of clone 95-2 |
| 11 | AA | CDR2 of VH of clone 95-2 |
| 12 | AA | CDR3 of VH of clone 95-2 |
| 13 | AA | CDR1 of VH of clone 073-1 |
| 14 | AA | CDR2 of VH of clone 073-1 |
| 15 | AA | CDR3 of VH of clone 073-1 |
| 16 | AA | CDR1 of VL of clone 83-128 |
| 17 | AA | CDR2 of VL of clone 83-128 |
| 18 | AA | CDR3 of VL of clone 83-128 |
| 19 | AA | CDR1 of VL of clone 95-2 |
| 20 | AA | CDR2 of VL of clone 95-2 |
| 21 | AA | CDR3 of VL of clone 95-2 |
| 22 | AA | CDR1 of VL of clone 073-1 |
| 23 | AA | CDR2 of VL of clone 073-1 |
| 24 | AA | CDR3 of VL of clone 073-1 |
| 25 | NA | VH of clone 83-128 |
| 26 | NA | VL of clone 83-128 |
| 27 | NA | VH of clone 95-2 |
| 28 | NA | VL of clone 95-2 |
| 29 | NA | VH of clone 073-1 |
| 30 | NA | VL of clone 073-1 |
| 31 | NA | E1/E2 1a H77 (FIG. 13) |
| 32 | AA | VH of clone 95-14 (FIG. 14) |
| 33 | AA | VH of clone 95-38 (FIG. 14) |
| 34 | AA | VH of clone 95-25 (FIG. 14) |
| 35 | AA | VH of clone 95-42 (FIG. 14) |
| 36 | AA | VH of clone 95-43 (FIG. 14) |
| 37 | AA | VH of clone 95-49 (FIG. 14) |
| 38 | AA | VH of clone 95-54 (FIG. 14) |
| 39 | AA | VH of clone 95-58 (FIG. 14) |
| 40 | AA | VH of clone 95-62 (FIG. 14) |
| 41 | AA | CDR1 of VH of clone 95-14 |
| 42 | AA | CDR2 of VH of clone 95-14 |
| 43 | AA | CDR3 of VH of clone 95-14 |
| 44 | AA | VL of clone 95-14 |
| 45 | AA | CDR1 of VL of clone 95-14 |
| 46 | AA | CDR2 of VL of clone 95-14 |
| 47 | AA | CDR3 of VL of clone 95-14 |
| 48 | NA | VH of clone 95-14 |
| 49 | NA | VL of clone 95-14 |
| 50 | AA | CDR1 of VH of clone 95-38 |
| 51 | AA | CDR2 of VH of clone 95-38 |
| 52 | AA | CDR3 of VH of clone 95-38 |
| 53 | AA | VL of clone 95-38 |
| 54 | AA | CDR1 of VL of clone 95-38 |
| 55 | AA | CDR2 of VL of clone 95-38 |
| 56 | AA | CDR3 of VL of clone 95-38 |
| 57 | NA | VH of clone 95-38 |
| 58 | NA | VL of clone 95-38 |
| 59 | AA | E2 412-423 (1a) QLINTNGSWHIN (FIG. 10) |
| 60 | AA | (1b) QLVNTNGSWHIN (FIG. 10) |
| 61 | AA | QLVNSNGSWHIN (FIG. 10) |
| 62 | AA | QLINSNGSWHIN (FIG. 10) |

-continued

| SEQ ID NO. | Type | Description of Sequence |
|---|---|---|
| 63 | AA | HLINTNGSWHIN (FIG. 10) |
| 64 | AA | QLIKTNGSWHIN (FIG. 10) |
| 65 | AA | QLVNTNGSWHVN (FIG. 10) |
| 66 | AA | QFVNTNGSWHIN (FIG. 10) |
| 67 | AA | QLIKNGSSWHIN (FIG. 10) |
| 68 | AA | QLVKTNGSWHIN (FIG. 10) |
| 69 | AA | HLVNTNGSWHIN (FIG. 10) |
| 70 | AA | HLVNSNGSWHIN (FIG. 10) |
| 71 | AA | QLIHTNGSWHIN (FIG. 10) |
| 72 | AA | QLVKTEGNWHIN (FIG. 10) |
| 73 | AA | NLIKTNGSWHIN (FIG. 10) |
| 74 | AA | QLIYTNGSWHIN (FIG. 10) |
| 75 | AA | QLINTNGSWHLN (FIG. 10) |
| 76 | AA | YLINTNGSWHIN (FIG. 10) |
| 77 | AA | SLINTNGSWHIN (FIG. 10) |
| 78 | AA | NLINTNGSWHIN (FIG. 10) |

-continued

| SEQ ID NO. | Type | Description of Sequence |
|---|---|---|
| 79 | AA | HLVNSNGSWHIN genotype 2b (FIG. 11) |
| 80 | AA | QLVNSSGSWHIN genotype 3a (FIG. 11) |
| 81 | AA | QLINSNGSWHIN genotype 4a (FIG. 11) |
| 82 | AA | QLIQNGSSWHIN genotype 5 (FIG. 11) |
| 83 | AA | QFVNTNGSWHIN genotype 5a (FIG. 11) |
| 84 | AA | QLIKNGSSWHIN genotype 6a (FIG. 11) |
| 85 | AA | QLIKTNGSWHIN genotype 6g (FIG. 11) |
| 86 | AA | QLINSNGSWHVN genotype 6k (FIG. 11) |
| 87 | AA | VH CDR1 consensus sequence |
| 88 | AA | VH CDR2 consensus sequence |
| 89 | AA | VH CDR3 consensus sequence |
| 90 | AA | VL CDR1 consensus sequence |
| 91 | AA | VL CDR2 consensus sequence |
| 92 | AA | VL CDR3 consensus sequence |

What is claimed is:

1. An isolated human monoclonal antibody, or antigen binding portion thereof, wherein the antibody, or antigen binding portion thereof comprises heavy and light chain variable regions comprising the sequences of SEQ ID NOs:1 and 2.

2. An isolated human monoclonal antibody, or antigen binding portion thereof, comprising a heavy chain variable region comprising the sequence of SEQ ID NO:1, wherein the antibody or antigen binding portion thereof binds to a non-conformational (linear) epitope on the HCV E2 protein.

3. An isolated human monoclonal antibody, or antigen binding portion thereof, comprising a light chain variable region comprising the sequence of SEQ ID NO:2, wherein the antibody or antigen binding portion thereof binds to a non-conformational (linear) epitope on the HCV E2 protein.

4. An isolated human monoclonal antibody, or antigen binding portion thereof, wherein the antibody, or antigen binding portion thereof comprises a heavy chain variable region CDR3 sequence comprising the sequence of SEQ ID NO:9, a light chain variable region CDR3 sequence comprising the sequence of SEQ ID NO:18, a heavy chain variable region CDR2 sequence comprising the sequence of SEQ ID NO:8, a light chain variable region CDR2 sequence comprising the sequence of SEQ ID NO:17, a heavy chain variable region CDR1 sequence comprising the sequence of SEQ ID NO:7, and a light chain variable region CDR1 sequence comprising the sequence of SEQ ID NO:16.

5. The isolated antibody o claim 4, wherein the antibody is a full-length antibody.

6. The isolated antibody, or antigen binding portion thereof of claim 4, wherein the antibody or antigen binding portion is selected from the group consisting of an antibody comprising an Fc domain, a single-chain antibody, and a Fab fragment.

7. The isolated antibody or antigen binding portion of claim 4, wherein the antibody or antigen binding portion inhibits binding of hepatitis C virus (HCV) to mammalian cells.

8. The isolated antibody or antigen binding portion of claim 4, wherein the antibody or antigen binding portion inhibits binding of an HCV E2 protein to mammalian cells.

9. The isolated antibody or antigen binding portion of claim 4, which binds to a non-conformational (linear) epitope on the HCV E2 protein and inhibits the ability of the virus to infect cells.

10. The isolated antibody or antigen binding portion of claim 4, wherein the antibody or antigen binding portion neutralizes HCV in an HCV pseudovirus neutralization assay.

11. The isolated antibody or antigen binding portion of claim 4, wherein the antibody inhibits HCV infection of a cell.

12. The isolated antibody or antigen binding portion of claim 4, wherein the antibody binds to two or more HCV genotypes of an HCV E2 protein or fragment thereof.

13. The isolated antibody or antigen binding portion of claim 4, wherein the antibody binds an HCV E2 protein from an HCV virus having a genotype selected from the group consisting of 1a, 1b, 2b, 3a, 4a, 5, 5a, 6a, 6g, 6k, and any combination thereof.

14. The isolated antibody or antigen binding portion of claim 4, wherein the antibody or antigen binding portion binds an epitope between amino acid residues 412-464, 412-423, or 413-420 of the E2 protein of SEQ ID NO:93.

15. The isolated antibody or antigen binding portion of claim 4, wherein the antibody or antigen binding portion thereof specifically binds to an HCV E2 protein, or fragment thereof, with a $K_D$ of at least about $1\times10^{-7}$ M, $1\times10^{-8}$ M, $1\times10^{-9}$ M, $1\times10^{-10}$ M, $1\times10^{-11}$ M, $1\times10^{-12}$ M or better.

16. The isolated antibody or antigen binding portion of claim 4, further comprising a label or a therapeutic agent.

17. A composition comprising the isolated antibody or antigen binding portion of claim 4 in a pharmaceutically acceptable carrier.

18. A kit comprising the isolated antibody or antigen binding portion of claim 4 and instruction for use of said antibody or antigen binding portion.

* * * * *

UNITED STATES PATENT AND TRADEMARK OFFICE

CERTIFICATE OF CORRECTION

PATENT NO. : 8,551,484 B2
APPLICATION NO. : 12/527663
DATED : October 8, 2013
INVENTOR(S) : Donna M. Ambrosino et al.

It is certified that error appears in the above-identified patent and that said Letters Patent is hereby corrected as shown below:

In the Claims:

Column 95, Claim 5, Line 36, replace "o claim 4" with --of claim 4--.

Signed and Sealed this
Third Day of December, 2013

Margaret A. Focarino

Margaret A. Focarino
*Commissioner for Patents of the United States Patent and Trademark Office*

SEQUENCE LISTING

```
<160> NUMBER OF SEQ ID NOS: 93

<210> SEQ ID NO 1
<211> LENGTH: 123
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Asn Asn Tyr
            20                  25                  30

Gly Met His Trp Val Arg Gln Thr Pro Gly Lys Gly Leu Glu Trp Leu
        35                  40                  45

Ala Val Ile Trp Phe Asp Glu Asn Asn Lys Tyr Tyr Ala Asp Ser Val
    50                  55                  60

Arg Gly Arg Phe Thr Ile Ser Arg Asp Asn Ser Lys Asn Thr Leu Phe
65                  70                  75                  80

Leu Gln Met Asn Ser Leu Lys Thr Glu Asp Thr Ala Met Tyr Tyr Cys
                85                  90                  95

Ala Arg Asp Ile Ser Leu Val Arg Asp Ala Phe Ile Tyr Phe Asp Phe
            100                 105                 110

Trp Gly Leu Gly Thr Leu Val Thr Val Ser Ser
        115                 120


<210> SEQ ID NO 2
<211> LENGTH: 106
<212> TYPE: PRT
<213> ORGANISM: Artificial Sequence
<220> FEATURE:
<223> OTHER INFORMATION: Synthetic Construct

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45
```

```
Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Ile Thr
                85                  90                  95

Phe Gly Gln Gly Thr Arg Leu Glu Ile Lys
            100                 105


<210> SEQ ID NO 3
<211> LENGTH: 124
<212> TYPE: PRT
<213> ORGANISM: Artificial Sequence
<220> FEATURE:
<223> OTHER INFORMATION: Synthetic Construct

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Asn Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Phe Thr Val Val Arg Gly Phe Phe Ile Tyr Phe Asp
            100                 105                 110

Tyr Trp Gly Gln Gly Thr Leu Val Thr Val Ser Ser
        115                 120


<210> SEQ ID NO 4
<211> LENGTH: 106
<212> TYPE: PRT
<213> ORGANISM: Artificial Sequence
<220> FEATURE:
<223> OTHER INFORMATION: Synthetic Construct

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Val Thr
                85                  90                  95

Phe Gly Gln Gly Thr Arg Leu Glu Ile Lys
            100                 105


<210> SEQ ID NO 5
```

<211> LENGTH: 126
<212> TYPE: PRT
<213> ORGANISM: Artificial Sequence
<220> FEATURE:
<223> OTHER INFORMATION: Synthetic Construct

<400> SEQUENCE: 5

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Met
        35                  40                  45

Ala Val Ile Trp Tyr Asp Glu Asn Asn Arg Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Thr Asn Tyr His Gly Ser Gly Ser Tyr Tyr Ile Tyr
            100                 105                 110

Phe Asp Tyr Trp Gly Gln Gly Thr Leu Val Thr Val Ser Ser
        115                 120                 125
```

<210> SEQ ID NO 6
<211> LENGTH: 106
<212> TYPE: PRT
<213> ORGANISM: Artificial Sequence
<220> FEATURE:
<223> OTHER INFORMATION: Synthetic Construct

<400> SEQUENCE: 6

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Thr Leu Glu Pro
65                  70                  75                  80

Glu Asp Phe Ala Val Tyr Tyr Cys Gln Gln Arg Ser Asn Trp Val Thr
                85                  90                  95

Phe Gly Gln Gly Thr Arg Leu Glu Ile Lys
            100                 105
```

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

```
Asn Tyr Gly Met His
1               5
```

<210> SEQ ID NO 8
<211> LENGTH: 17
<212> TYPE: PRT

<213> ORGANISM: Artificial Sequence
<220> FEATURE:
<223> OTHER INFORMATION: Synthetic peptide

<400> SEQUENCE: 8

Val Ile Trp Phe Asp Glu Asn Asn Lys Tyr Tyr Ala Asp Ser Val Arg
1               5                   10                  15

Gly

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide

<400> SEQUENCE: 9

Ala Arg Asp Ile Ser Leu Val Arg Asp Ala Phe Ile Tyr Phe Asp Phe
1               5                   10                  15

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10

Ser Tyr Gly Met His
1               5

<210> SEQ ID NO 11
<211> LENGTH: 17
<212> TYPE: PRT
<213> ORGANISM: Artificial Sequence
<220> FEATURE:
<223> OTHER INFORMATION: Synthetic peptide

<400> SEQUENCE: 11

Val Ile Trp Phe Asp Gly Asn Asn Gln Tyr Tyr Ala Asp Ser Val Lys
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Synthetic peptide

<400> SEQUENCE: 12

Ala Arg Asp Ile Phe Thr Val Val Arg Gly Phe Phe Ile Tyr Phe Asp
1               5                   10                  15

Tyr

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

Asn Tyr Gly Met His
1               5

<210> SEQ ID NO 14
<211> LENGTH: 17
<212> TYPE: PRT
<213> ORGANISM: Artificial Sequence
<220> FEATURE:
<223> OTHER INFORMATION: Synthetic peptide

<400> SEQUENCE: 14

Val Ile Trp Tyr Asp Glu Asn Asn Arg Tyr Ser Ala Asp Ser Val Lys
1 5 10 15

Gly

<210> SEQ ID NO 15
<211> LENGTH: 19
<212> TYPE: PRT
<213> ORGANISM: Artificial Sequence
<220> FEATURE:
<223> OTHER INFORMATION: Synthetic peptide

<400> SEQUENCE: 15

Ala Arg Asp Pro Thr Asn Tyr His Gly Ser Gly Ser Tyr Tyr Ile Tyr
1 5 10 15

Phe Asp Tyr

<210> SEQ ID NO 16
<211> LENGTH: 11
<212> TYPE: PRT
<213> ORGANISM: Artificial Sequence
<220> FEATURE:
<223> OTHER INFORMATION: Synthetic peptide

<400> SEQUENCE: 16

Arg Ala Ser Gln Ser Val Ser Ser Tyr Leu Ala
1 5 10

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Asp Ala Ser Asn Arg Ala Thr
1 5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Gln Gln Arg Ser Asn Trp Ile Thr
1 5

<210> SEQ ID NO 19
<211> LENGTH: 11
<212> TYPE: PRT
<213> ORGANISM: Artificial Sequence
<220> FEATURE:
<223> OTHER INFORMATION: Synthetic peptide

<400> SEQUENCE: 19

Arg Ala Ser Gln Ser Val Gly Ser Tyr Leu Ala

-continued 1 5 10

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Asp Ala Ser Asn Arg Ala Thr
1 5

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide

<400> SEQUENCE: 21

Gln Gln Arg Ser Asn Trp Val Thr
1 5

<210> SEQ ID NO 22
<211> LENGTH: 11
<212> TYPE: PRT
<213> ORGANISM: Artificial Sequence
<220> FEATURE:
<223> OTHER INFORMATION: Synthetic peptide

<400> SEQUENCE: 22

Arg Ala Ser Gln Ser Val Ser Ser Tyr Leu Ala
1 5 10

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Asp Ala Ser Asn Arg Ala Thr
1 5

<210> SEQ ID NO 24
<211> LENGTH: 8
<212> TYPE: PRT
<213> ORGANISM: Artificial Sequence
<220> FEATURE:
<223> OTHER INFORMATION: Synthetic peptide

<400> SEQUENCE: 24

Gln Gln Arg Ser Asn Trp Val Thr
1 5

<210> SEQ ID NO 25
<211> LENGTH: 369
<212> TYPE: DNA
<213> ORGANISM: Artificial Sequence
<220> FEATURE:
<223> OTHER INFORMATION: Synthetic Construct

<400> SEQUENCE: 25
caggtgcagc tggtggagtc tgggggaggc gtggtccagc ctgggagatc cctgagactc 60
tcctgtacag cgtctggatt caccttcaat aactatggca tgcactgggt ccgccagact 120

-continued

```
ccaggcaagg ggctggagtg gctggcagtt atatggtttg atgaaaataa taagtactat    180

gcagactccg tgaggggccg attcaccatc tccagagaca attccaagaa cacgctgttt    240

ctgcaaatga acagcctgaa aaccgaagac acggctatgt attattgtgc gagagatatt    300

tctctggttc gggatgcttt tatctacttt gacttctggg gcctgggaac cctggtcacc    360

gtctcctca                                                            369
```

```
<210> SEQ ID NO 26
<211> LENGTH: 318
<212> TYPE: DNA
<213> ORGANISM: Artificial Sequence
<220> FEATURE:
<223> OTHER INFORMATION: Synthetic Construct

<400> SEQUENCE: 26

gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag cgtagcaact ggatcacctt cggccaaggg    300

acacgactgg agatcaaa                                                  318
```

```
<210> SEQ ID NO 27
<211> LENGTH: 372
<212> TYPE: DNA
<213> ORGANISM: Artificial Sequence
<220> FEATURE:
<223> OTHER INFORMATION: Synthetic Construct

<400> SEQUENCE: 27

caggtgcagc tggtggagtc tgggggaggc gtggtccagc ctgggaggtc cctgagactc     60

tcctgtgcag cgtctggatt caccttcagt agctatggca tgcactgggt ccgccaggct    120

ccaggcaagg ggctggaatg ggtggcagtt atatggtttg atggaaataa tcaatactat    180

gcagactccg tgaagggccg attcaccatc tccagagaca attccaagaa cacgctgtat    240

ctgcaaatga acagcctgag agccgaggac acggctgtgt attactgtgc gagagacatc    300

tttactgtgg ttcggggatt ttttatctac tttgactact ggggccaggg aaccctggtc    360

accgtctcct ca                                                        372
```

```
<210> SEQ ID NO 28
<211> LENGTH: 318
<212> TYPE: DNA
<213> ORGANISM: Artificial Sequence
<220> FEATURE:
<223> OTHER INFORMATION: Synthetic Construct

<400> SEQUENCE: 28

gaaattgtgt tgacacagtc tccagccacc ctgtctttgt ctccagggga aagagccacc     60

ctctcctgca gggccagtca gagtgttggc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag cgtagcaact gggtcacctt cggccaaggg    300

acacgactgg agatcaaa                                                  318
```

-continued

<210> SEQ ID NO 29
<211> LENGTH: 378
<212> TYPE: DNA
<213> ORGANISM: Artificial Sequence
<220> FEATURE:
<223> OTHER INFORMATION: Synthetic Construct

<400> SEQUENCE: 29
caggtgcagc tggtggagtc tgggggaggc gtggtccagc ctgggaggtc cctgagactc 60
tcctgtgcag cgtctggatt caccttcagt aactatggca tgcactgggt ccgccaggct 120
ccaggcaagg ggctggagtg gatggcagtt atctggtatg atgaaaataa tagatactct 180
gcagactccg tgaagggccg attcaccatc tccagagaca attccaagaa cacgctgtat 240
ctgcaaatga acagcctgag agccgaggac acggctgtgt attactgtgc gagagatcct 300
acgaattacc atggttcggg gagttattat atctactttg actactgggg ccagggaacc 360
ctggtcaccg tctcctca 378

<210> SEQ ID NO 30
<211> LENGTH: 318
<212> TYPE: DNA
<213> ORGANISM: Artificial Sequence
<220> FEATURE:
<223> OTHER INFORMATION: Synthetic Construct

<400> SEQUENCE: 30
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcac cctagagcct 240
gaagattttg cagtttatta ctgtcagcag cgtagcaact gggtcacctt cggccaaggg 300
acacgactgg agatcaaa 318

<210> SEQ ID NO 31
<211> LENGTH: 1785
<212> TYPE: DNA
<213> ORGANISM: Artificial Sequence
<220> FEATURE:
<223> OTHER INFORMATION: Synthetic Construct

<400> SEQUENCE: 31
cgctatagaa gcttgccgcc accatggcca ccggcaacct gcccggctgc tccttctcca 60
tcttcctgct ggccctgctg tcctgcctga ccgtgcccgc ctccgcctac caggtgcgca 120
actcctccgg cctgtaccac gtgaccaacg actgccctaa ctcctccatc gtgtacgagg 180
ccgccgacgc catcctgcac actcctggct gcgtgccctg cgtgcgcgag ggcaacgcct 240
cccgctgctg ggtggccgtg actcctaccg tggccacccg cgacggcaag ctgcccacca 300
cccagctgcg ccgccacatc gacctgctgg tgggctccgc caccctgtgc tccgccctgt 360
acgtgggcga cctgtgcggc tccgtgttcc tggtgggcca gctgttcacc ttctctcctc 420
gccgccactg gaccacccag gactgcaact gctccatcta ccctggccac atcaccggcc 480
accgcatggc ctgggacatg atgatgaact ggtctcccac cgccgccctg gtggtggccc 540
agctgctgcg catccctcag gccatcatgg acatgatcgc cggcgcccac tggggcgtcc 600
tggccggcat cgcctacttc tccatggtgg gcaactgggc caaggtgctg gtggtgctgc 660
tgctgttcgc cggcgtggac gccgagaccc acgtgacggg cggctccgcc ggccgcacca 720
ccgccggcct ggtgggcctg ctgacacccg gcgccaagca gaacatccag ctgatcaaca 780
ccaacggctc ctggcacatc aactccaccg ccctgaactg caacgagtcc ctgaacaccg 840
gctggctggc cggcctgttc taccagcaca agttcaactc ctccggctgt cccgagcgcc 900
tggcctcctg ccgccgcctg accgacttcg cccagggctg gggccctatc tcctacgcca 960
acggctccgg cctggacgag cggccctact gctggcacta ccctcctcgc ccttgcggca 1020
tcgtgcccgc caagtccgtg tgcggccctg tgtactgctt cactccctct cccgtggtgg 1080
tgggcaccac cgaccgctcc ggcgctccca cctactcctg gggcgccaac gacaccgacg 1140
tgttcgtgct gaacaacacc cgccctcctc tgggcaactg gttcggctgc acctggatga 1200
actccaccgg cttcaccaag gtgtgcggcg cgcctccctg cgtgatcggc ggcgtgggca 1260
acaacaccct gctgtgccct accgactgct tccgcaagca tcccgaggcc acctactccc 1320
gctgcggctc cgggccctgg atcactcctc gctgcatggt ggactatccc taccgcctgt 1380
ggcactatcc ctgcaccatc aactacacca tcttcaaggt gcgcatgtac gtgggcggcg 1440
tggagcaccg cctggaggcg gcgtgcaact ggacccgcgg cgagcgctgc gacctggagg 1500
accgcgaccg ctccgagctg tctcctctgc tgctgtccac cacccagtgg caggtgctgc 1560
cctgctcctt caccaccctg cccgcgctgt ccaccggcct gatccacctg caccagaaca 1620
tcgtggacgt gcagtacctg tacggcgtgg gctcctccat cgcgtcctgg gcgatcaagt 1680
gggagtacgt ggtgctgctg ttcctgctgc tggcggacgc gcgcgtgtgc tcctgcctgt 1740
ggatgatgct gctgatctcc caggcggagg cgtctagagg agtca 1785

<210> SEQ ID NO 32
<211> LENGTH: 124
<212> TYPE: PRT
<213> ORGANISM: Artificial Sequence
<220> FEATURE:
<223> OTHER INFORMATION: Synthetic Construct

<400> SEQUENCE: 32

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Leu Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Phe Thr Met Val Arg Gly Val Phe Ile Tyr Phe Asp
            100                 105                 110

Tyr Trp Gly Gln Gly Thr Leu Val Thr Val Ser Ser
        115                 120
```

<210> SEQ ID NO 33
<211> LENGTH: 124
<212> TYPE: PRT
<213> ORGANISM: Artificial Sequence
<220> FEATURE:
<223> OTHER INFORMATION: Synthetic Construct

<400> SEQUENCE: 33

```
Gln Val Gln Leu Val Glu Ser Gly Gly Gly Val Val Gln Pro Gly Arg
```

-continued

```
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Leu Asp Gly Ser Asn Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Ile Phe Thr Val Ala Arg Gly Val Ile Ile Tyr Phe Asp
            100                 105                 110

Tyr Trp Gly Gln Gly Thr Leu Val Thr Val Ser Ser
        115                 120


<210> SEQ ID NO 34
<211> LENGTH: 124
<212> TYPE: PRT
<213> ORGANISM: Artificial Sequence
<220> FEATURE:
<223> OTHER INFORMATION: Synthetic Construct

<400> SEQUENCE: 34

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Phe Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Phe Thr Met Asp Arg Gly Val Phe Ile Tyr Phe Asp
            100                 105                 110

Tyr Trp Gly Gln Gly Thr Leu Val Thr Val Ser Ser
        115                 120


<210> SEQ ID NO 35
<211> LENGTH: 124
<212> TYPE: PRT
<213> ORGANISM: Artificial Sequence
<220> FEATURE:
<223> OTHER INFORMATION: Synthetic Construct

<400> SEQUENCE: 35

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Glu Ser Asn Lys Tyr Tyr Ala Asp Ser Val
    50                  55                  60

Lys Gly Arg Phe Thr Ile Ser Arg Asp Asn Ser Lys Asn Thr Leu Tyr
```

-continued

```
65                  70                  75                  80

Leu Gln Met Asn Ser Leu Arg Ala Glu Asp Thr Ala Val Tyr Tyr Cys
                85                  90                  95

Ala Arg Asp Ile Phe Thr Met Val Arg Gly Val Phe Ile Tyr Phe Asp
            100                 105                 110

Tyr Trp Gly Gln Gly Thr Leu Val Thr Val Ser Ser
        115                 120


<210> SEQ ID NO 36
<211> LENGTH: 124
<212> TYPE: PRT
<213> ORGANISM: Artificial Sequence
<220> FEATURE:
<223> OTHER INFORMATION: Synthetic Construct

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Asn Asn Lys Tyr Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Phe Thr Met Val Arg Gly Val Phe Ile Tyr Phe Asp
            100                 105                 110

Tyr Trp Gly Gln Gly Thr Leu Val Thr Val Ser Ser
        115                 120


<210> SEQ ID NO 37
<211> LENGTH: 124
<212> TYPE: PRT
<213> ORGANISM: Artificial Sequence
<220> FEATURE:
<223> OTHER INFORMATION: Synthetic Construct

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Asp Ile Phe Thr Met Val Arg Gly Val Phe Ile Tyr Phe Asp
            100                 105                 110

Tyr Trp Gly Gln Gly Thr Leu Val Thr Val Ser Ser
        115                 120
```

<210> SEQ ID NO 38
<211> LENGTH: 124
<212> TYPE: PRT
<213> ORGANISM: Artificial Sequence
<220> FEATURE:
<223> OTHER INFORMATION: Synthetic Construct

<400> SEQUENCE: 38

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Phe Thr Met Val Arg Gly Val Phe Ile Tyr Phe Asp
            100                 105                 110

Tyr Trp Gly Gln Gly Thr Leu Val Thr Val Ser Ser
        115                 120
```

<210> SEQ ID NO 39
<211> LENGTH: 124
<212> TYPE: PRT
<213> ORGANISM: Artificial Sequence
<220> FEATURE:
<223> OTHER INFORMATION: Synthetic Construct

<400> SEQUENCE: 39

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Glu Asn Asn Lys Tyr Tyr Ala Asp Ser Val
    50                  55                  60

Lys Gly Arg Phe Thr Ile Ser Arg Asp Asn Ser Asn Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Phe Thr Met Val Arg Gly Val Phe Ile Tyr Phe Asp
            100                 105                 110

Tyr Trp Gly Gln Gly Thr Leu Val Thr Val Ser Ser
        115                 120
```

<210> SEQ ID NO 40
<211> LENGTH: 124
<212> TYPE: PRT
<213> ORGANISM: Artificial Sequence
<220> FEATURE:
<223> OTHER INFORMATION: Synthetic Construct

<400> SEQUENCE: 40

```
Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Leu Ser Ser Tyr
            20                  25                  30

Gly Met His Trp Val Arg Gln Ala Pro Gly Lys Gly Leu Glu Trp Met
        35                  40                  45

Ala Val Ile Trp Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Phe Thr Met Val Arg Gly Val Phe Ile Tyr Phe Asp
            100                 105                 110

Tyr Trp Gly Gln Gly Thr Leu Val Thr Val Ser Ser
        115                 120


<210> SEQ ID NO 41
<211> LENGTH: 5
<212> TYPE: PRT
<213> ORGANISM: Artificial Sequence
<220> FEATURE:
<223> OTHER INFORMATION: Synthetic peptide

<400> SEQUENCE: 41

Ser Tyr Gly Met His
1               5


<210> SEQ ID NO 42
<211> LENGTH: 17
<212> TYPE: PRT
<213> ORGANISM: Artificial Sequence
<220> FEATURE:
<223> OTHER INFORMATION: Synthetic peptide

<400> SEQUENCE: 42

Val Ile Trp Tyr Asp Gly Asn Asn Lys Tyr Tyr Ala Asp Ser Val Lys
1               5                   10                  15

Gly


<210> SEQ ID NO 43
<211> LENGTH: 17
<212> TYPE: PRT
<213> ORGANISM: Artificial Sequence
<220> FEATURE:
<223> OTHER INFORMATION: Synthetic peptide

<400> SEQUENCE: 43

Ala Arg Asp Ile Phe Thr Met Val Arg Gly Val Phe Ile Tyr Phe Asp
1               5                   10                  15

Tyr


<210> SEQ ID NO 44
<211> LENGTH: 106
<212> TYPE: PRT
<213> ORGANISM: Artificial Sequence
<220> FEATURE:
<223> OTHER INFORMATION: Synthetic Construct

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30
```

-continued

```
Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Val Thr
                85                  90                  95

Phe Gly Gln Gly Thr Arg Leu Glu Ile Lys
            100                 105


<210> SEQ ID NO 45
<211> LENGTH: 11
<212> TYPE: PRT
<213> ORGANISM: Artificial Sequence
<220> FEATURE:
<223> OTHER INFORMATION: Synthetic peptide

<400> SEQUENCE: 45

Arg Ala Ser Gln Ser Val Gly Ser Tyr Leu Ala
1               5                   10


<210> SEQ ID NO 46
<211> LENGTH: 7
<212> TYPE: PRT
<213> ORGANISM: Artificial Sequence
<220> FEATURE:
<223> OTHER INFORMATION: Synthetic peptide

<400> SEQUENCE: 46

Asp Ala Ser Asn Arg Ala Thr
1               5


<210> SEQ ID NO 47
<211> LENGTH: 8
<212> TYPE: PRT
<213> ORGANISM: Artificial Sequence
<220> FEATURE:
<223> OTHER INFORMATION: Synthetic peptide

<400> SEQUENCE: 47

Gln Gln Arg Ser Asn Trp Val Thr
1               5


<210> SEQ ID NO 48
<211> LENGTH: 372
<212> TYPE: DNA
<213> ORGANISM: Artificial Sequence
<220> FEATURE:
<223> OTHER INFORMATION: Synthetic Construct

<400> SEQUENCE: 48

caggtgcagc tggtggagtc tgggggaggc gtggtccagc ctgggaggtc cctgagactc      60

tcctgtgcag cgtctggatt catcctcagt agctatggca tgcactgggt ccgccaggct     120

ccaggcaagg ggctggagtg ggtggcagtt atatggtatg atggaaataa taaatactat     180

gcagactccg tgaagggccg attcaccatc tccagagaca attccaagaa cacgctgtat     240

ctgcaaatga acagcctgag agccgaggac acggctgtgt attactgtgc gagagacatc     300

tttactatgg ttcggggagt ttttatctac tttgactact ggggccaggg aaccctggtc     360

accgtctcct ca                                                         372


<210> SEQ ID NO 49
```

<211> LENGTH: 318
<212> TYPE: DNA
<213> ORGANISM: Artificial Sequence
<220> FEATURE:
<223> OTHER INFORMATION: Synthetic Construct

<400> SEQUENCE: 49
gaaattgtgt tgacacagtc tccagccacc ctgtctttgt ctccagggga aagagccacc 60
ctctcctgca gggccagtca gagtgttggc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag cgtagcaact gggtcacctt cggccaaggg 300
acacgactgg agatcaaa 318

<210> SEQ ID NO 50
<211> LENGTH: 5
<212> TYPE: PRT
<213> ORGANISM: Artificial Sequence
<220> FEATURE:
<223> OTHER INFORMATION: Synthetic peptide

<400> SEQUENCE: 50

Ser Tyr Gly Met His
1 5

<210> SEQ ID NO 51
<211> LENGTH: 17
<212> TYPE: PRT
<213> ORGANISM: Artificial Sequence
<220> FEATURE:
<223> OTHER INFORMATION: Synthetic peptide

<400> SEQUENCE: 51

Val Ile Trp Leu Asp Gly Ser Asn Thr Tyr Tyr Ala Asp Ser Val Lys
1 5 10 15

Gly

<210> SEQ ID NO 52
<211> LENGTH: 17
<212> TYPE: PRT
<213> ORGANISM: Artificial Sequence
<220> FEATURE:
<223> OTHER INFORMATION: Synthetic peptide

<400> SEQUENCE: 52

Ala Arg Asp Ile Phe Thr Val Ala Arg Gly Val Ile Ile Tyr Phe Asp
1 5 10 15

Tyr

<210> SEQ ID NO 53
<211> LENGTH: 106
<212> TYPE: PRT
<213> ORGANISM: Artificial Sequence
<220> FEATURE:
<223> OTHER INFORMATION: Synthetic Construct

<400> SEQUENCE: 53

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile

-continued 35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Val Thr
85 90 95

Phe Gly Gln Gly Thr Arg Leu Glu Ile Lys
100 105

<210> SEQ ID NO 54
<211> LENGTH: 11
<212> TYPE: PRT
<213> ORGANISM: Artificial Sequence
<220> FEATURE:
<223> OTHER INFORMATION: Synthetic peptide

<400> SEQUENCE: 54

Arg Ala Ser Gln Ser Val Ser Ser Tyr Leu Ala
1 5 10

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Asp Ala Ser Asn Arg Ala Thr
1 5

<210> SEQ ID NO 56
<211> LENGTH: 8
<212> TYPE: PRT
<213> ORGANISM: Artificial Sequence
<220> FEATURE:
<223> OTHER INFORMATION: Synthetic peptide

<400> SEQUENCE: 56

Gln Gln Arg Ser Asn Trp Val Thr
1 5

<210> SEQ ID NO 57
<211> LENGTH: 372
<212> TYPE: DNA
<213> ORGANISM: Artificial Sequence
<220> FEATURE:
<223> OTHER INFORMATION: Synthetic Construct

<400> SEQUENCE: 57
caggtgcaac tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggcttg atggaagtaa cacatactat 180
gcagactccg tgaagggccg attcaccatt tctagagaca attccaagaa cacgctgttt 240
ctgcaaatga acagcctgag agccgaggac acggctgtgt attactgtgc gagagacatc 300
tttactgtgg ctcggggagt tattatctac tttgactact ggggccaggg aaccctggtc 360
accgtctcct ca 372

<210> SEQ ID NO 58
<211> LENGTH: 318

<212> TYPE: DNA
<213> ORGANISM: Artificial Sequence
<220> FEATURE:
<223> OTHER INFORMATION: Synthetic Construct

<400> SEQUENCE: 58
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag cgtagcaact gggtcacctt cggccaaggg 300
acacgactgg agatcaaa 318

<210> SEQ ID NO 59
<211> LENGTH: 12
<212> TYPE: PRT
<213> ORGANISM: Hepatitis C virus

<400> SEQUENCE: 59

Gln Leu Ile Asn Thr Asn Gly Ser Trp His Ile Asn
1 5 10

<210> SEQ ID NO 60
<211> LENGTH: 12
<212> TYPE: PRT
<213> ORGANISM: Hepatitis C virus

<400> SEQUENCE: 60

Gln Leu Val Asn Thr Asn Gly Ser Trp His Ile Asn
1 5 10

<210> SEQ ID NO 61
<211> LENGTH: 12
<212> TYPE: PRT
<213> ORGANISM: Hepatitis C virus

<400> SEQUENCE: 61

Gln Leu Val Asn Ser Asn Gly Ser Trp His Ile Asn
1 5 10

<210> SEQ ID NO 62
<211> LENGTH: 12
<212> TYPE: PRT
<213> ORGANISM: Hepatitis C virus

<400> SEQUENCE: 62

Gln Leu Ile Asn Ser Asn Gly Ser Trp His Ile Asn
1 5 10

<210> SEQ ID NO 63
<211> LENGTH: 12
<212> TYPE: PRT
<213> ORGANISM: Hepatitis C virus

<400> SEQUENCE: 63

His Leu Ile Asn Thr Asn Gly Ser Trp His Ile Asn
1 5 10

<210> SEQ ID NO 64
<211> LENGTH: 12
<212> TYPE: PRT
<213> ORGANISM: Hepatitis C virus

<400> SEQUENCE: 64

Gln Leu Ile Lys Thr Asn Gly Ser Trp His Ile Asn
1 5 10

<210> SEQ ID NO 65
<211> LENGTH: 12
<212> TYPE: PRT
<213> ORGANISM: Hepatitis C virus

<400> SEQUENCE: 65

Gln Leu Val Asn Thr Asn Gly Ser Trp His Val Asn
1 5 10

<210> SEQ ID NO 66
<211> LENGTH: 12
<212> TYPE: PRT
<213> ORGANISM: Hepatitis C virus

<400> SEQUENCE: 66

Gln Phe Val Asn Thr Asn Gly Ser Trp His Ile Asn
1 5 10

<210> SEQ ID NO 67
<211> LENGTH: 12
<212> TYPE: PRT
<213> ORGANISM: Hepatitis C virus

<400> SEQUENCE: 67

Gln Leu Ile Lys Asn Gly Ser Ser Trp His Ile Asn
1 5 10

<210> SEQ ID NO 68
<211> LENGTH: 12
<212> TYPE: PRT
<213> ORGANISM: Hepatitis C virus

<400> SEQUENCE: 68

Gln Leu Val Lys Thr Asn Gly Ser Trp His Ile Asn
1 5 10

<210> SEQ ID NO 69
<211> LENGTH: 12
<212> TYPE: PRT
<213> ORGANISM: Hepatitis C virus

<400> SEQUENCE: 69

His Leu Val Asn Thr Asn Gly Ser Trp His Ile Asn
1 5 10

<210> SEQ ID NO 70
<211> LENGTH: 12
<212> TYPE: PRT
<213> ORGANISM: Hepatitis C virus

<400> SEQUENCE: 70

His Leu Val Asn Ser Asn Gly Ser Trp His Ile Asn
1 5 10

<210> SEQ ID NO 71
<211> LENGTH: 12
<212> TYPE: PRT
<213> ORGANISM: Hepatitis C virus

<400> SEQUENCE: 71

Gln Leu Ile His Thr Asn Gly Ser Trp His Ile Asn 1 5 10

<210> SEQ ID NO 72
<211> LENGTH: 12
<212> TYPE: PRT
<213> ORGANISM: Hepatitis C virus

<400> SEQUENCE: 72

Gln Leu Val Lys Thr Glu Gly Asn Trp His Ile Asn
1 5 10

<210> SEQ ID NO 73
<211> LENGTH: 12
<212> TYPE: PRT
<213> ORGANISM: Hepatitis C virus

<400> SEQUENCE: 73

Asn Leu Ile Lys Thr Asn Gly Ser Trp His Ile Asn
1 5 10

<210> SEQ ID NO 74
<211> LENGTH: 12
<212> TYPE: PRT
<213> ORGANISM: Hepatitis C virus

<400> SEQUENCE: 74

Gln Leu Ile Tyr Thr Asn Gly Ser Trp His Leu Asn
1 5 10

<210> SEQ ID NO 75
<211> LENGTH: 12
<212> TYPE: PRT
<213> ORGANISM: Hepatitis C virus

<400> SEQUENCE: 75

Gln Leu Ile Asn Thr Asn Gly Ser Trp His Leu Asn
1 5 10

<210> SEQ ID NO 76
<211> LENGTH: 12
<212> TYPE: PRT
<213> ORGANISM: Hepatitis C virus

<400> SEQUENCE: 76

Tyr Leu Ile Asn Thr Asn Gly Ser Trp His Ile Asn
1 5 10

<210> SEQ ID NO 77
<211> LENGTH: 12
<212> TYPE: PRT
<213> ORGANISM: Hepatitis C virus

<400> SEQUENCE: 77

Ser Leu Ile Asn Thr Asn Gly Ser Trp His Ile Asn
1 5 10

<210> SEQ ID NO 78
<211> LENGTH: 12
<212> TYPE: PRT
<213> ORGANISM: Hepatitis C virus

<400> SEQUENCE: 78

Asn Leu Ile Asn Thr Asn Gly Ser Trp His Ile Asn
1 5 10

<210> SEQ ID NO 79
<211> LENGTH: 12
<212> TYPE: PRT
<213> ORGANISM: Hepatitis C virus

<400> SEQUENCE: 79

His Leu Val Asn Ser Asn Gly Ser Trp His Ile Asn
1 5 10

<210> SEQ ID NO 80
<211> LENGTH: 12
<212> TYPE: PRT
<213> ORGANISM: Hepatitis C virus

<400> SEQUENCE: 80

Gln Leu Val Asn Ser Ser Gly Ser Trp His Ile Asn
1 5 10

<210> SEQ ID NO 81
<211> LENGTH: 12
<212> TYPE: PRT
<213> ORGANISM: Hepatitis C virus

<400> SEQUENCE: 81

Gln Leu Ile Asn Ser Asn Gly Ser Trp His Ile Asn
1 5 10

<210> SEQ ID NO 82
<211> LENGTH: 12
<212> TYPE: PRT
<213> ORGANISM: Hepatitis C virus

<400> SEQUENCE: 82

Gln Leu Ile Gln Asn Gly Ser Ser Trp His Ile Asn
1 5 10

<210> SEQ ID NO 83
<211> LENGTH: 12
<212> TYPE: PRT
<213> ORGANISM: Hepatitis C virus

<400> SEQUENCE: 83

Gln Phe Val Asn Thr Asn Gly Ser Trp His Ile Asn
1 5 10

<210> SEQ ID NO 84
<211> LENGTH: 12
<212> TYPE: PRT
<213> ORGANISM: Hepatitis C virus

<400> SEQUENCE: 84

Gln Leu Ile Lys Asn Gly Ser Ser Trp His Ile Asn
1 5 10

<210> SEQ ID NO 85
<211> LENGTH: 12
<212> TYPE: PRT
<213> ORGANISM: Hepatitis C virus

<400> SEQUENCE: 85

Gln Leu Ile Lys Thr Asn Gly Ser Trp His Ile Asn
1 5 10

<210> SEQ ID NO 86
<211> LENGTH: 12
<212> TYPE: PRT

<213> ORGANISM: Hepatitis C virus

<400> SEQUENCE: 86

Gln Leu Ile Asn Ser Asn Gly Ser Trp His Val Asn
1               5                   10

<210> SEQ ID NO 87
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: variable small, polar amino acid

<400> SEQUENCE: 87

Xaa Tyr Gly Met His
1               5

<210> SEQ ID NO 88
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: variable amino acid
<220> FEATURE:
<221> NAME/KEY: MOD_RES
<222> LOCATION: (6)..(6)
<223> OTHER INFORMATION: variable amino acid
<220> FEATURE:
<221> NAME/KEY: MOD_RES
<222> LOCATION: (7)..(7)
<223> OTHER INFORMATION: variable small, polar amino acid
<220> FEATURE:
<221> NAME/KEY: MOD_RES
<222> LOCATION: (9)..(9)
<223> OTHER INFORMATION: variable amino acid
<220> FEATURE:
<221> NAME/KEY: MOD_RES
<222> LOCATION: (15)..(15)
<223> OTHER INFORMATION: variable hydrophobic amino acid
<220> FEATURE:
<221> NAME/KEY: MOD_RES
<222> LOCATION: (16)..(16)
<223> OTHER INFORMATION: variable positively charged polar amino acid

<400> SEQUENCE: 88

Val Ile Trp Xaa Asp Xaa Xaa Asn Xaa Tyr Tyr Ala Asp Ser Xaa Xaa
1               5                   10                  15

Gly

<210> SEQ ID NO 89
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: Phe or not present
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (7)..(7)
<223> OTHER INFORMATION: variable hydrophobic amino acid
<220> FEATURE:
<221> NAME/KEY: MOD_RES
<222> LOCATION: (8)..(8)
<223> OTHER INFORMATION: variable amino acid
<220> FEATURE:
<221> NAME/KEY: MOD_RES
<222> LOCATION: (10)..(10)
<223> OTHER INFORMATION: variable small amino acid
<220> FEATURE:
<221> NAME/KEY: MOD_RES
<222> LOCATION: (11)..(11)
<223> OTHER INFORMATION: variable amino acid
<220> FEATURE:
<221> NAME/KEY: MOD_RES
<222> LOCATION: (12)..(12)
<223> OTHER INFORMATION: variable hydrophobic amino acid
<220> FEATURE:
<221> NAME/KEY: MOD_RES
<222> LOCATION: (17)..(17)
<223> OTHER INFORMATION: variable aromatic amino acid

<400> SEQUENCE: 89

Ala Arg Asp Ile Xaa Xaa Xaa Xaa Arg Xaa Xaa Xaa Ile Tyr Phe Asp
1 5 10 15

Xaa

<210> SEQ ID NO 90
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: variable amino acid

<400> SEQUENCE: 90

Arg Ala Ser Gln Ser Val Xaa Ser Tyr Leu Ala
1 5 10

<210> SEQ ID NO 91
<211> LENGTH: 7
<212> TYPE: PRT
<213> ORGANISM: Artificial Sequence
<220> FEATURE:
<223> OTHER INFORMATION: Synthetic peptide

<400> SEQUENCE: 91

Asp Ala Ser Asn Arg Ala Thr
1 5

<210> SEQ ID NO 92
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: variable small, hydrophobic amino acid

<400> SEQUENCE: 92

Gln Gln Arg Ser Asn Trp Xaa Thr
1 5

<210> SEQ ID NO 93
<211> LENGTH: 383

<212> TYPE: PRT
<213> ORGANISM: Hepatitis C virus
<220> FEATURE:
<221> NAME/KEY: MISC_FEATURE
<222> LOCATION: (1)..(383)
<223> OTHER INFORMATION: Amino Acid 1 is amino acid 364 of the HCV E2 protein

<400> SEQUENCE: 93

```
Met Val Gly Asn Trp Ala Lys Val Leu Val Val Leu Leu Leu Phe Ala
1               5                   10                  15

Gly Val Asp Ala Glu Thr His Val Thr Gly Gly Ser Ala Gly Arg Thr
            20                  25                  30

Thr Ala Gly Leu Val Gly Leu Leu Thr Pro Gly Ala Lys Gln Asn Ile
        35                  40                  45

Gln Leu Ile Asn Thr Asn Gly Ser Trp His Ile Asn Ser Thr Ala Leu
    50                  55                  60

Asn Cys Asn Glu Ser Leu Asn Thr Gly Trp Leu Ala Gly Leu Phe Tyr
65                  70                  75                  80

Gln His Lys Phe Asn Ser Ser Gly Cys Pro Glu Arg Leu Ala Ser Cys
                85                  90                  95

Arg Arg Leu Thr Asp Phe Ala Gln Gly Trp Gly Pro Ile Ser Tyr Ala
            100                 105                 110

Asn Gly Ser Gly Leu Asp Glu Arg Pro Tyr Cys Trp His Tyr Pro Pro
        115                 120                 125

Arg Pro Cys Gly Ile Val Pro Ala Lys Ser Val Cys Gly Pro Val Tyr
    130                 135                 140

Cys Phe Thr Pro Ser Pro Val Val Val Gly Thr Thr Asp Arg Ser Gly
145                 150                 155                 160

Ala Pro Thr Tyr Ser Trp Gly Ala Asn Asp Thr Asp Val Phe Val Leu
                165                 170                 175

Asn Asn Thr Arg Pro Pro Leu Gly Asn Trp Phe Gly Cys Thr Trp Met
            180                 185                 190

Asn Ser Thr Gly Phe Thr Lys Val Cys Gly Ala Pro Pro Cys Val Ile
        195                 200                 205

Gly Gly Val Gly Asn Asn Thr Leu Leu Cys Pro Thr Asp Cys Phe Arg
    210                 215                 220

Lys His Pro Glu Ala Thr Tyr Ser Arg Cys Gly Ser Gly Pro Trp Ile
225                 230                 235                 240

Thr Pro Arg Cys Met Val Asp Tyr Pro Tyr Arg Leu Trp His Tyr Pro
                245                 250                 255

Cys Thr Ile Asn Tyr Thr Ile Phe Lys Val Arg Met Tyr Val Gly Gly
            260                 265                 270

Val Glu His Arg Leu Glu Ala Ala Cys Asn Trp Thr Arg Gly Glu Arg
        275                 280                 285

Cys Asp Leu Glu Asp Arg Asp Arg Ser Glu Leu Ser Pro Leu Leu Leu
    290                 295                 300

Ser Thr Thr Gln Trp Gln Val Leu Pro Cys Ser Phe Thr Thr Leu Pro
305                 310                 315                 320

Ala Leu Ser Thr Gly Leu Ile His Leu His Gln Asn Ile Val Asp Val
                325                 330                 335

Gln Tyr Leu Tyr Gly Val Gly Ser Ser Ile Ala Ser Trp Ala Ile Lys
            340                 345                 350

Trp Glu Tyr Val Val Leu Leu Phe Leu Leu Leu Ala Asp Ala Arg Val
        355                 360                 365
```

-continued

```
Cys Ser Cys Leu Trp Met Met Leu Leu Ile Ser Gln Ala Glu Ala
    370                 375                 380
```